US012698334B2

(12) United States Patent
Fischer et al.

(10) Patent No.: US 12,698,334 B2
(45) Date of Patent: **\*Aug. 4, 2026**

(54) ANTI-IL-1R3 ANTIBODIES FOR USE IN INFLAMMATORY CONDITIONS

(71) Applicant: SANOFI BIOTECHNOLOGY, Paris (FR)

(72) Inventors: Stephan Fischer, Weilheim (DE); Karsten Beckmann, Vaterstetten (DE)

(73) Assignee: SANOFI BIOTECHNOLOGY, Gentilly (FR)

( * ) Notice: Subject to any disclaimer, the term of this patent is extended or adjusted under 35 U.S.C. 154(b) by 407 days.

This patent is subject to a terminal disclaimer.

(21) Appl. No.: 18/184,759

(22) Filed: Mar. 16, 2023

(65) Prior Publication Data

US 2023/0383000 A1     Nov. 30, 2023

Related U.S. Application Data

(63) Continuation of application No. 16/612,052, filed as application No. PCT/EP2018/061846 on May 8, 2018, now Pat. No. 11,639,392.

(30) Foreign Application Priority Data

May 8, 2017     (EP) .................................... 17169953

(51) Int. Cl.
*C07K 16/28* (2006.01)
*A61P 29/00* (2006.01)

(52) U.S. Cl.
CPC .......... *C07K 16/2866* (2013.01); *A61P 29/00* (2018.01); *C07K 2317/565* (2013.01); *C07K 2317/71* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,202,238 A | 4/1993 | Fell, Jr. et al. | |
| 5,204,244 A | 4/1993 | Fell et al. | |
| 5,283,179 A | 2/1994 | Wood | |
| 5,641,641 A | 6/1997 | Wood | |
| 5,650,289 A | 7/1997 | Wood | |
| 6,280,955 B1 | 8/2001 | Cao | |
| 6,586,207 B2 | 7/2003 | Tirrell et al. | |
| 6,602,684 B1 | 8/2003 | Umana et al. | |
| 7,390,880 B2 | 6/2008 | Bednarik et al. | |
| 10,906,971 B2 | 2/2021 | Fischer et al. | |
| 11,198,728 B2 | 12/2021 | Fischer et al. | |
| 11,203,642 B2 | 12/2021 | Fischer et al. | |
| 11,639,392 B2 | 5/2023 | Fischer et al. | |
| 12,024,564 B2 | 7/2024 | Fischer et al. | |
| 12,054,552 B2 | 8/2024 | Lange et al. | |
| 12,240,898 B2 | 3/2025 | Fischer et al. | |
| 2003/0026806 A1 | 2/2003 | Witte et al. | |

| | | | |
|---|---|---|---|
| 2004/0214988 A1 | 10/2004 | Tirrell et al. | |
| 2012/0251531 A1 | 10/2012 | Baehner et al. | |
| 2014/0017167 A1 | 1/2014 | Fioretos et al. | |
| 2015/0315279 A1 | 11/2015 | Jiang et al. | |
| 2019/0106487 A1 | 4/2019 | Fischer et al. | |
| 2019/0194336 A1 | 6/2019 | Fischer et al. | |
| 2020/0140559 A1 | 5/2020 | Fischer et al. | |
| 2020/0407438 A1 | 12/2020 | Fischer et al. | |
| 2022/0089751 A1 | 3/2022 | Fischer et al. | |
| 2022/0169718 A1 | 6/2022 | Fischer et al. | |
| 2024/0101691 A1 | 3/2024 | Coolbaugh et al. | |
| 2024/0409644 A1 | 12/2024 | Fischer et al. | |
| 2025/0019452 A1 | 1/2025 | Lange et al. | |

FOREIGN PATENT DOCUMENTS

| | | |
|---|---|---|
| CN | 1934072 A | 3/2007 |
| CN | 102939304 A | 2/2013 |
| EP | 0120694 A2 | 10/1984 |
| EP | 0125023 A1 | 11/1984 |
| EP | 0239400 A2 | 9/1987 |
| EP | 0488470 A1 | 6/1992 |
| EP | 0519596 A1 | 12/1992 |
| EP | 0194276 B2 | 1/2002 |

(Continued)

OTHER PUBLICATIONS

U.S. Appl. No. 15/739,410 2019/0106487 U.S. Pat. No. 10,906,971, filed Dec. 22, 2017 Apr. 11, 2019 Feb. 2, 2021, Stephen Fischer, Monoclonal Anti-IL-1RACP Antibodies.
U.S. Appl. No. 16/898,074 2020/0407438 U.S. Pat. No. 11,198,728, filed Jun. 10, 2020 Dec. 31, 2020 Dec. 14, 2021, Stephan Fischer, Monoclonal Anti-IL-1RACP Antibodies.
U.S. Appl. No. 17/522,600 2022/0169718 U.S. Pat. No. 12,240,898, filed Nov. 9, 2021 Jun. 2, 2022 Mar. 4, 2025, Stephan Fischer, Monoclonal Anti-IL-1RACP Antibodies.
U.S. Appl. No. 19/025,463, filed Jan. 16, 2025, Stephan Fischer, Monoclonal Anti-IL-1RACP Antibodies.

(Continued)

*Primary Examiner* — Ruixiang Li
(74) *Attorney, Agent, or Firm* — LATHROP GPM LLP; James H. Velema, Esq.; Michael J. Spellberg, Esq.

(57) ABSTRACT

The present invention relates to methods for treating medical conditions and/or disorders characterized by uncontrolled or abnormal expression of members of the IL1R3 signaling pathway such as IL-1α, IL-1ß, IL-33, IL-36, IL1RA and/or IL1R3, as well as variants thereof.

Figure 14:
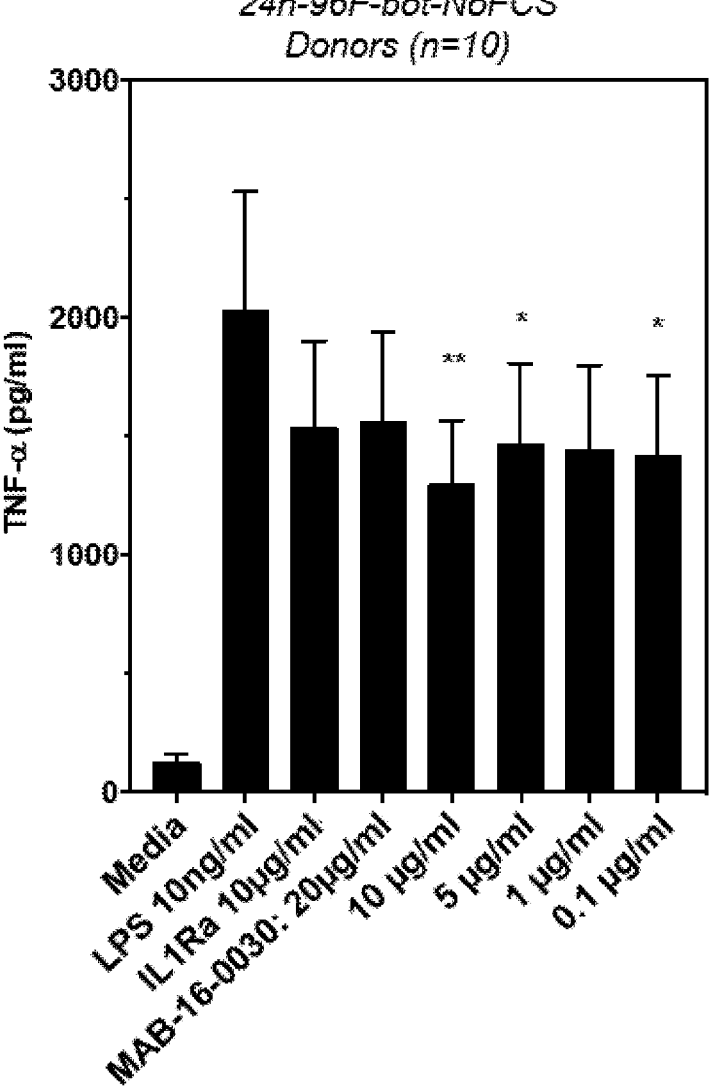
Figure 14:
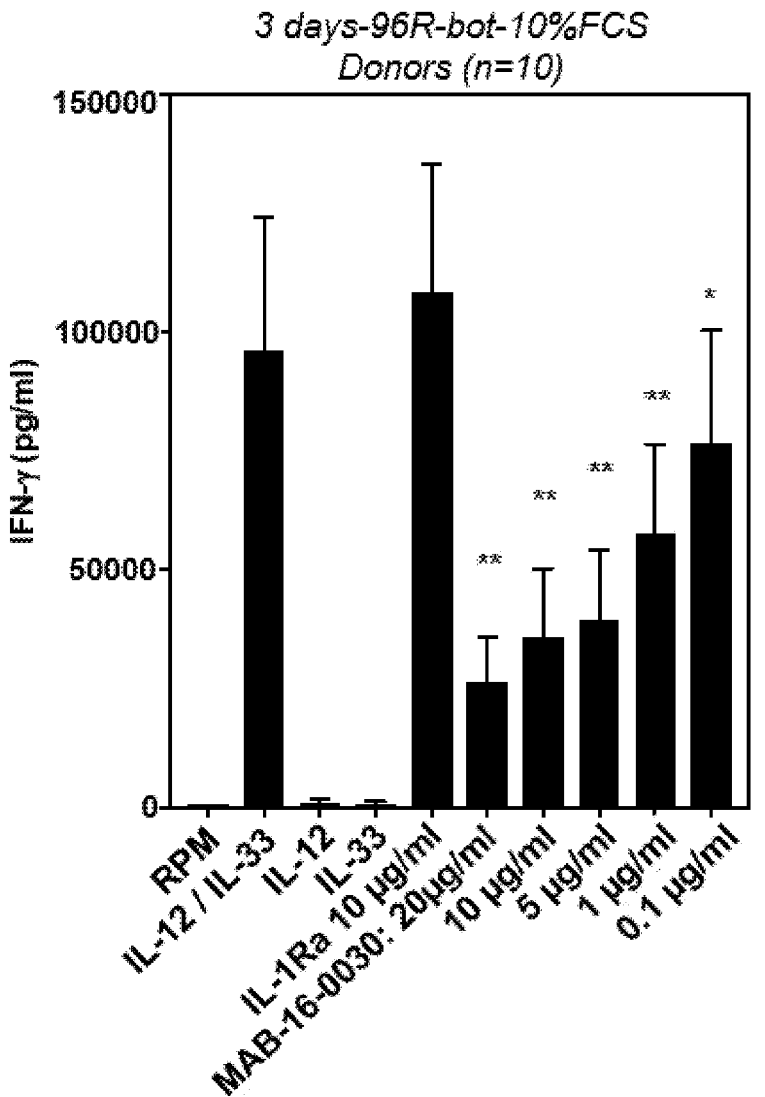
Figure 14:
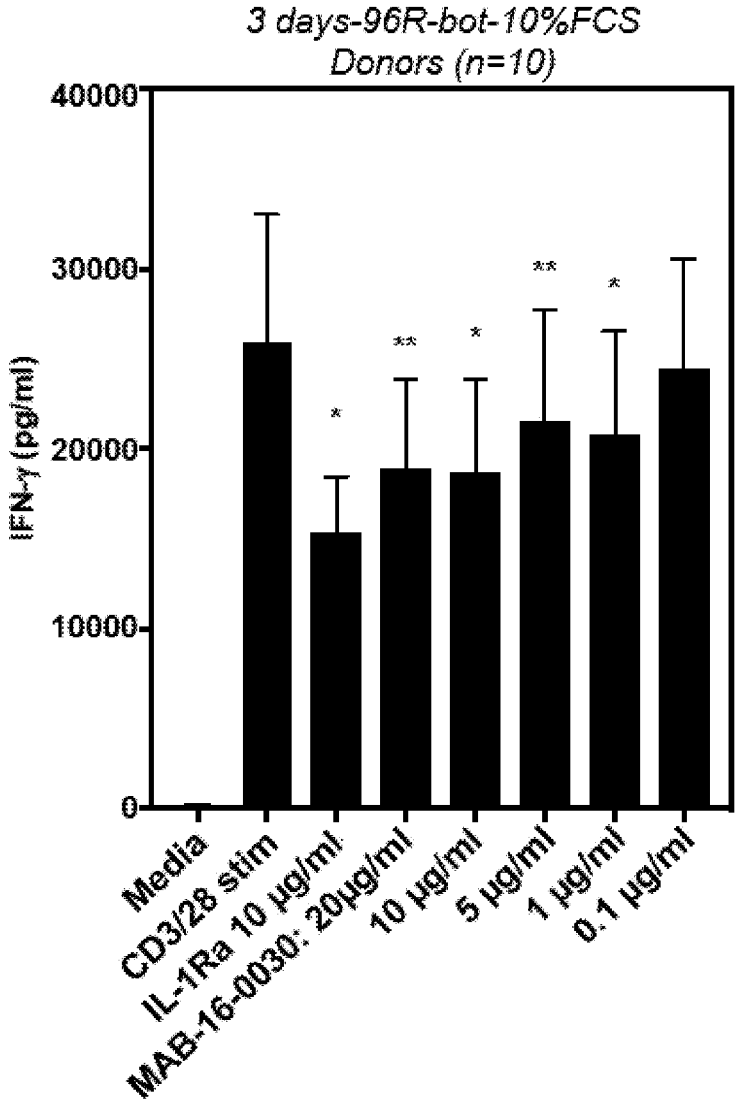
Figure 14:
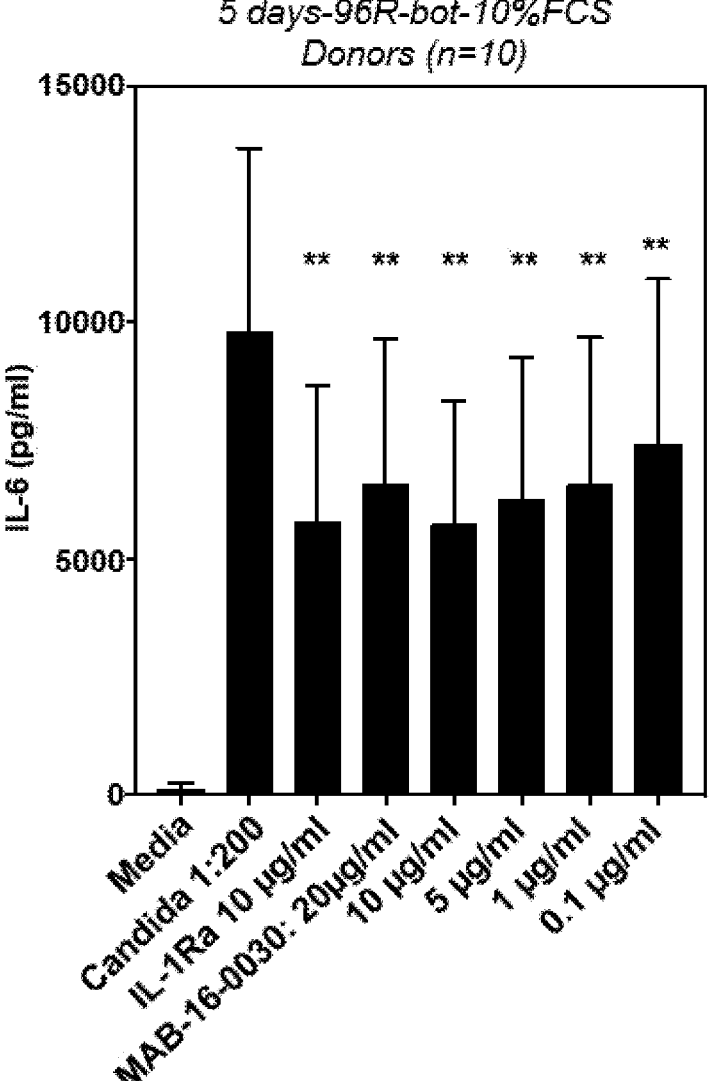
Figure 14:
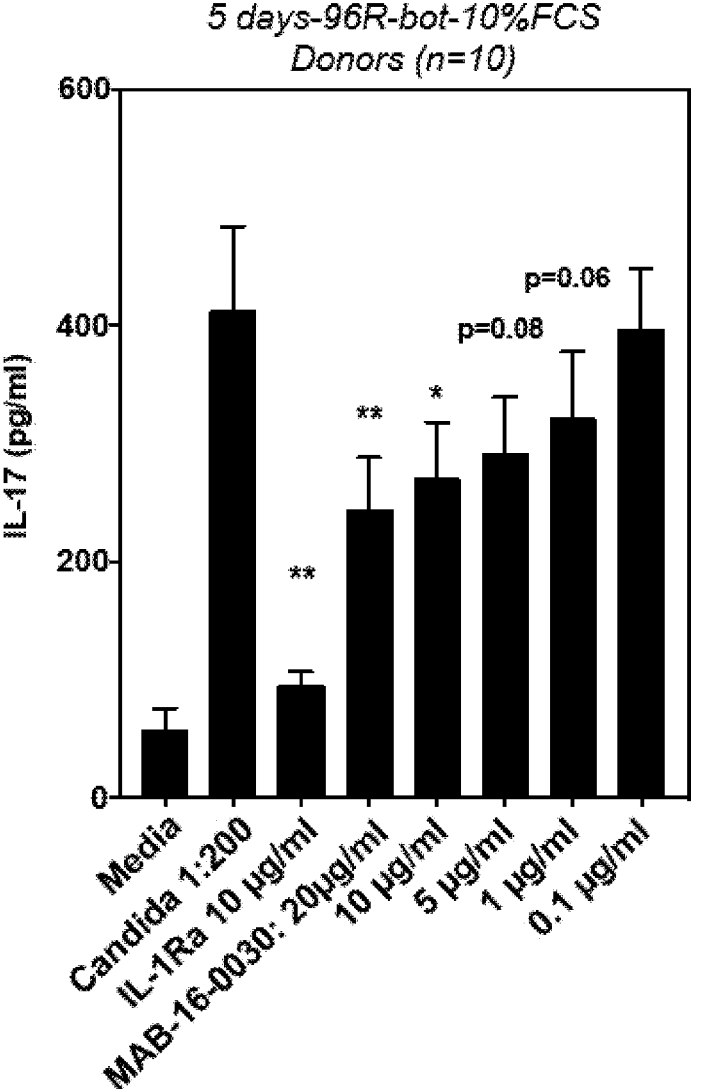

More specifically, the present invention relates to anti-IL1R3 antibodies for use in the treatment of an IL1R3-mediated inflammatory condition and/or disorder in a subject.

Such conditions and disorders include but are not limited to inflammatory diseases, immune disorders, fibrotic disorders, eosinophilic disorders, infection, pain, a central nervous system disorder, an ophthalmologic disorder, Hereditary Systemic Inflammatory Diseases, and Systemic and Local Inflammatory Diseases and cancer associated chronic inflammation.

12 Claims, 46 Drawing Sheets

Specification includes a Sequence Listing.

(56) References Cited

FOREIGN PATENT DOCUMENTS

| EP | 1255780 A1 | 11/2002 |
| EP | 1633787 A1 | 3/2006 |
| JP | 2014-511348 A | 5/2014 |
| WO | WO 1986/001533 A1 | 3/1986 |
| WO | WO 1988/007089 A1 | 9/1988 |
| WO | WO 1996/014339 A1 | 5/1996 |
| WO | WO 1996/023067 A1 | 8/1996 |
| WO | WO 1997/037016 A1 | 10/1997 |
| WO | WO 1998/005787 A1 | 2/1998 |
| WO | WO 1998/023289 A1 | 6/1998 |
| WO | WO 1998/048032 A2 | 10/1998 |
| WO | WO 1999/051642 A1 | 10/1999 |
| WO | WO 1999/058572 A1 | 11/1999 |
| WO | WO 2000/009560 A2 | 2/2000 |
| WO | WO 2000/032767 A1 | 6/2000 |
| WO | WO 2000/042072 A2 | 7/2000 |
| WO | WO 2001/055216 A1 | 8/2001 |
| WO | WO 2002/044215 A2 | 6/2002 |
| WO | WO 2002/060919 A2 | 8/2002 |
| WO | WO 2002/064630 A2 | 8/2002 |
| WO | WO 2003/014309 A2 | 2/2003 |
| WO | WO 2002/064630 A3 | 8/2003 |
| WO | WO 2003/073238 A2 | 9/2003 |
| WO | WO 2003/074569 A2 | 9/2003 |
| WO | WO 2004/009823 A1 | 1/2004 |
| WO | WO 2004/016750 A2 | 2/2004 |
| WO | WO 2004/022718 A2 | 3/2004 |
| WO | WO 2004/029207 A2 | 4/2004 |
| WO | WO 2004/035752 A2 | 4/2004 |
| WO | WO 2004/063351 A2 | 7/2004 |
| WO | WO 2004/065540 A2 | 8/2004 |
| WO | WO 2004/074455 A2 | 9/2004 |
| WO | WO 2004/099249 A2 | 11/2004 |
| WO | WO 2004/100987 A2 | 11/2004 |
| WO | WO 2004/106377 A1 | 12/2004 |
| WO | WO 2005/035727 A2 | 4/2005 |
| WO | WO 2005/040217 A2 | 5/2005 |
| WO | WO 2005/044859 A2 | 5/2005 |
| WO | WO 2005/070963 A1 | 8/2005 |
| WO | WO 2005/073164 A1 | 8/2005 |
| WO | WO 2005/074524 A2 | 8/2005 |
| WO | WO 2005/077981 A2 | 8/2005 |
| WO | WO 2005/092925 A2 | 10/2005 |
| WO | WO 2005/123780 A2 | 12/2005 |
| WO | WO 2006/019447 A1 | 2/2006 |
| WO | WO 2006/047350 A2 | 5/2006 |
| WO | WO 2006/085967 A2 | 8/2006 |
| WO | WO 2007/003041 A1 | 1/2007 |
| WO | WO 2007/031875 A2 | 3/2007 |
| WO | WO 2008/045140 A1 | 4/2008 |
| WO | WO 2009/120903 A2 | 10/2009 |
| WO | WO 2010/108127 A1 | 9/2010 |
| WO | WO 2011/021014 A2 | 2/2011 |
| WO | WO 2011/124718 A1 | 10/2011 |
| WO | WO 2011/147903 A1 | 12/2011 |
| WO | WO 2012/098407 A1 | 7/2012 |
| WO | WO 2012/142391 A1 | 10/2012 |
| WO | WO 2012/177595 A1 | 12/2012 |
| WO | WO 2013/023015 A2 | 2/2013 |
| WO | WO 2013/165894 A2 | 11/2013 |
| WO | WO 2013/165894 A3 | 11/2013 |
| WO | WO 2014/100772 A1 | 6/2014 |
| WO | WO 2014/113433 A1 | 7/2014 |
| WO | WO 2015/132602 A1 | 9/2015 |
| WO | WO 2016/020502 A1 | 2/2016 |
| WO | WO 2016/207304 A2 | 12/2016 |

OTHER PUBLICATIONS

U.S. Appl. No. 16/099,059 2019/0194336 U.S. Pat. No. 11,203,642, filed Nov. 5, 2018 Jun. 27, 2019 Dec. 21, 2021, Stephan Fischer, Humanized Anti-IL-1R3 Antibodies.

U.S. Appl. No. 17/410,153 2022/0089751 U.S. Pat. No. 12,024,564, filed Aug. 24, 2021 Mar. 24, 2022, Jul. 2, 2024, Stephan Fischer, Humanized Anti-IL-1R3 Antibodies.

U.S. Appl. No. 18/668,446 2024/0409644, filed May 20, 2024 Dec. 12, 2024, Stephan Fischer, Humanized Anti-IL1R3 Antibodies.

U.S. Appl. No. 16/612,052 2020/0140559 U.S. Pat. No. 11,639,392, filed Nov. 8, 2019 May 7, 2020 May 2, 2023, Stephan Fischer, Anti-IL-1R3 Antibodies for Use in Inflammatory Conditions.

U.S. Appl. No. 18/184,759 2023/0383000, filed Mar. 16, 2023 Nov. 30, 2023, Stephan Fischer, Anti-IL-1R3 Antibodies for Use in Inflammatory Conditions.

U.S. Appl. No. 18/471,388 2024/0101691 U.S. Pat. No. 12,054,552, filed Sep. 21, 1023 Mar. 28, 2024 Aug. 6, 2024, Humanized Anit-IL-1R3 Antibody and Methods of Use.

U.S. Appl. No. 18/754,385 2025/0019452, filed Jun. 26, 2024 Jan. 16, 2025, Christian Lange, Humanized Anti-IL-1R3 Antibody and Methods of Use.

Alam, J. and Cook, J.L., Reporter Genes: Application to the Study of Mammalian Gene Transcription. Anal Biochem. 1990; 188(2):245-54.

Ali, S. et al., IL-1 receptor Accessory Protein is Essential for IL-33-induced Activation of T Lymphocytes and Mast Cells. Proc Natl Acad Sci USA, 2007; 104(47):18660-5.

Balagurunathan, Y. et al., Gene Expression Profiling-Based Identification of Cell-Surface Targets for Developing Multimeric Ligands in Pancreatic Cancer. Mol Cancer Ther. 2008: 7(9):3071-80.

Barbas, C.F., III et al., In vitro Evolution of a Neutralizing Human Antibody to Human Immunodeficiency Virus Type 1 to Enhance Affinity and Broaden Strain Cross- Reactivity. Proc Natl Acad Sci USA. 1994; 91(9):3809-13.

Bardin, "Canakinumab for the Patient With Difficult-to-Treat Gouty Arthritis: Review of the Clinical Evidence", Joint Bone Spine, 2015, 82: eS9-eS16.

Barnes, L.M. et al., Advances in Animal Cell Recombinant Protein Production: GS-NSO Expression System. Cytotechnology. 2000; 32(2):109-23.

Barnes, L.M. et al., Characterization of the Stability of Recombinant Protein Production in the GS-NSO Expression System. Biotech Bioeng. 2001; 73(4):261-70.

Brueggemann, M. et al., Comparison of the Effector Functions of Human Immunoglobulins Using a Matched Set of Chimeric Antibodies. J Exp Med. 1987; 166(5):1351-61.

Capel, P.J.A. et al., Heterogeneity of Human IgG Fc Receptors. Immunomethods. 1994; 4(1):2534.

Carter, P. et al., Humanization of an Anti-p185HER2 Antibody for Human Cancer Therapy. Proc Natl Acad Sci USA. 1992; 89(10):4285-9.

Chin, J.W. and Schultz, P.G., In Vivo Photocrosslinking with Unnatural Amino Acid Mutagenesis. ChemBioChem. 2002; 3(11):1135-7.

Chin, J.W. et al., Addition of a Photocrosslinking Amino Acid to the Genetic Code of *Escherichia coli*. Proc Natl Acad Sci U.S.A. 2002; 99(17):11020-4.

Chin, J.W. et al., Addition of p-Azido-L-phenylalanine to the Genetic Code of *Escherichia coli*. J Amer Chem Soc. 2002; 124:9026-7.

Cullinan et al., The IL-1 Receptor Accessory Protein Is an Essential Component of the IL-1 Receptor, J. Immunology, Nov. 15, 1998, 161(10): 5614-5620.

Daeron, M., Fc Receptor Biology. Annu Rev Immunol. 1997; 15:203-34.

Davis, R.S. et al., Fc Receptor Homologs: Newest Members of a Remarkably Diverse Fc Receptor Gene Family. Immunol Rev. 2002; 190:123-36.

de Haas et al., Fcγ Receptors of Phagocytes. J Lab Clin Med. 1995; 126(4):330-41.

de Wet, J.R. et al., Firefly Luciferase Gene: Structure and Expression in Mammalian Cells. Mol Cell Biol. 1987; 7:725-37.

de Wildt, R.M. and Hoet, R.M., The Recovery of Immunoglobulin Sequences from Single Human B Cells by Clonal Expansion. Methods Mol Biol. 2002; 178:121-31.

Dinarello, C.A., Immunological and Inflammatory Functions of the Interleukin-1 Family, Annual Review of Immunology, 2009, 27: 519-550.

(56)　　　　　　References Cited

OTHER PUBLICATIONS

Dinarello, C.A., Interleukin-1 in the Pathogenesis and Treatment of Inflammatory Diseases. Blood. 2011; 117(14):3720-32.

Diu et al., Activation of resting human B cells by helper T-cell clone supernatant: characterization of a human B-cell-activating factor, PNAS USA, 1987, 84(24): 9140-9144.

Durocher, Y. et al., High-level and High-throughput Recombinant Protein Production by Transient Transfection of Suspension-growing Human 293-EBNA1 Cells. Nucleic Acids Res. 2002; 30(2):E9 (9 pages).

Edelman, et al., "The Covalent Structure of an Entire γG Immuno-globulin Molecule", PNAS USA, May 1, 1969, 63(1): 78-85.

Extended European Search Report for European Patent Application No. 21191122.7, mailed Nov. 24, 2021.

Geisse, S. et al., Eukaryotic Expression Systems: A Comparison. Protein Expr Purif. 1996; 8(3):271-82.

Guyer, R.L. et al., Immunoglobulin Binding by Mouse Intestinal Epithelial Cell Receptors. J Immunol. 1976; 117(2):587-93.

Hawkins, R.E. et al., Selection of Phage Antibodies by Binding Affinity: Mimicking Affinity Maturation. J Mol Biol. 1992; 226(3):889-96.

Hoffmann, P. et al., Murine Bone Marrow-derived Macrophages Constitute Feeder Cells for Human B Cell Hybridomas. J Immunol Methods. 1996; 196(1):85-91.

Huang, J. et al., Recruitment of IRAK to the Interleukin 1 Receptor Complex Requires Interleukin 1 Receptor Accessory Protein. Proc Natl Acad Sci USA. 1997; 94(24):12829-32.

Huston, J.S., Protein Engineering of Single-Chain Fv Analogs and Fusion Proteins. Methods Enzymol. 1991; 203:46-88.

International Preliminary Report on Patentability for PCT International Patent Application No. PCT/EP2016/064588, mailed Dec. 26, 2017.

International Search Report and Written Opinion for PCT International Patent Application No. PCT/EP2016/064588, mailed Jan. 11, 2017.

International Search Report and Written Opinion for PCT International Patent Application No. PCT/EP2017/060925, mailed Jul. 7, 2017.

International Search Report and Written Opinion for PCT International Patent Application No. PCT/EP2018/061846, mailed Jul. 6, 2018, 12 pages.

Jackson, J.R. et al., In vitro Antibody Maturation. Improvement of a High Affinity, Neutralizing Antibody Against IL-1 R. J Immunol. 1995; 154(7):3310-9.

Jaras, M. et al., Isolation and Killing of Candidate Chronic Myeloid Leukemia Stem Cells by Antibody Targeting of IL-1 Receptor Accessory Protein. Proc Natl Acad Sci USA. 2010; 107(37):16280-5.

Jefferis, R. et al., Interaction Sites on Human IgG-Fc for FOR: Current Models. Immunol Lett. 2002; 82(1-2):57-65.

Johnson, G. and Wu, T.T., Kabat Database and Its Applications: 30 Years After the First Variability Plot. Nucleic Acids Res. 2000; 28(1):214-8.

Kaufman, R.J., Overview of Vector Design for Mammalian Gene Expression. Mol Biotechnol. 2000; 16(2):151-60.

Kim, J.-K. et al., Localization of the Site of Murine IgG1 Molecule that is Involved in Binding to the Murine Intestinal Fc Receptor. Eur J Immunol. 1994; 24(10):2429-34.

Kodituwakko, A.P. et al., Isolation of Antigen-Specific B Cells. Immunol Cell Biol. 2003; 81(3):163-70.

Krupke, D.M. et al., The Mouse Tumor Biology Database. Nat Rev Cancer. 2008; 8(6):459-65.

Lefranc, M.-P., Nomenclature of the Human Immunoglobulin Genes. Curr Protoc Immunol. 2000; Appendix 1P (37 pages).

Li, X et al., Mutant Cells That Do Not Respond to Interleukin-1 (IL-1) Reveal a Novel Role for IL-1 Receptor-Associated Kinase. Mol Cel Biol. 1999; 19(7):4643-52.

Love, T.W. et al., Recombinant Antibodies Possessing Novel Effector Functions. Methods Enzymol. 1989; 178:515-27.

Makrides, S.C., Components of Vectors for Gene Transfer and Expression in Mammalian Cells. Protein Expr Purif. 1999; 17(2):183-202.

Mansur et al., Engagement of IL-1 receptor accessory protein (IL-1RAcP) with the monoclonal antibody AY19 provides co-activating signals and prolongs the CD2-induced proliferation of peripheral blood lymphocytes, Immunol Lett., 2011, 139(1):52-57.

Marks, J.D. et al., Bypassing Immunization: Building High Affinity Human Antibodies by Chain Shuffling. BioTechnology. 1992; 10(7):779-83.

Morrison, S.L. et al., Chimeric Human Antibody Molecules: Mouse Antigen-Binding Domains with Human Constant Region Domains. Proc Natl Acad Sci USA. 1984; 81(21):6851-5.

Neuberger, M.C. et al., A Hapten-Specific Chimaeric IgE with Human Physiological Effector Function. Nature. 1985; 314(6008):268-70.

Norderhaug, L. et al., Versatile Vectors for Transient and Stable Expression of Recombinant Antibody Molecules in Mammalian Cells. J Immunol Methods. 1997; 204(1):77-87.

Orencole, S.F. and Dinarello, C.A., Characterization of a Subclone (D10S) of the D10.G4.1 Helper T-cell Line which Proliferates to Attomolar Concentrations of Interleukin-1 in the Absence of Mitogens. Cytokine. 1989; 1(1):14-22.

Orlandi, R. et al., Cloning Immunoglobulin Variable Domains for Expression by the Polymerase Chain Reaction. Proc Natl Acad Sci USA. 1989; 86(10):3833-7.

Ow, D.W. et al., Transient and Stable Expression of the Firefly Luciferase Gene in Plant Cells and Transgenic Plants. Science. 1986; 234(4778):856-9.

Paul, Fundamental Immunology, 3rd Edition, Raven Press, New York, 1993, Chapter 9, pp. 292-295.

Raju, T.S., Glycosylation Variations with Expression Systems and Their Impact on Biological Activity of Therapeutic Immunoglobulins. BioProcess Intl. 2003; 1(4):44-53.

Ravetch, J.V. and Kinet, J.P., Fc Receptors. Annu Rev Immunol. 1991; 9:457-492.

Riechmann, L. et al., Reshaping Human Antibodies for Therapy. Nature. 1988; 332:323-7.

Routier, F.H., The Glycosylation Pattern of a Humanized IgGI Antibody (D1.3) Expressed in CHO Cells. Glycoconj J. 1997; 14(2):201-7.

Roy, A. et al., Increased Efficiency of 7-Irradiated versus Mitomycin C-Treated Feeder Cells for the Expansion of Normal Human Cells in Long-Term Cultures. J Hematother Stem Cell Res. 2001; 10(6):873-80.

Rudikoff et al., Single amino acid substitution altering antigen-binding specificity, PNAS USA, Mar. 1982, 79: 1979-1983.

Schier, R. et al., Identification of Functional and Structural Amino-Acid Residues by Parsimonious Mutagenesis. Gene. 1995; 169(2):147-55.

Schlaeger, E.-J. and Christensen, K., Transient Gene Expression in Mammalian Cells Grown in Serum-Free Suspension Culture. Cytotechnology. 1999; 30(1-3):71-83.

Schlaeger, E.-J., The Protein Hydrolysate, Primatone RL, is a Cost-Effective Multiple Growth Promoter of Mammalian Cell Culture in Serum-Containing and Serum-Free Media and Displays Anti-Apoptosis Properties. J Immunol Methods. 1996; 194(2):191-9.

Sonderman, P. et al., The 3.2-A Crystal Structure of the Human IgG1 Fc Fragment-FcγRIII Complex. Nature. 2000; 406(6793):267-73.

Towne, J.E. et al., Interleukin (IL)-1 F6, IL-1F8, and IL-F9 Signal Through IL-1 Rrp2 and IL-1RAcP to Activate the Pathway Leading to NF-KB and MAPKs. J Biol Chem. 2004; 279(14):13677-13688.

Umaña et al., Engineered Glycoforms of an Antineuro-Blastoma IgG1 with Optimized Antibody-Dependent Cellular Cytotoxic Activity. Nature Biotechnol. 1999; 17(2):176-80.

Vajdos et al., Comprehensive Functional Maps of the Antigen-Binding Site of an Anti-ErbB2 Antibody Obtained with Shotgun Scanning Mutagenesis, Journal of Molecular Biology, 2002, 320: 415-428.

Wang, L. and Schultz, P.G., Expanding the Genetic Code. Chem Commun. 2002; 0(1):1-11.

(56) References Cited

OTHER PUBLICATIONS

Wedemayer, G.J. et al., Structural Insights into the Evolution of an Antibody Combining Site. Science. 1997; 276(5319):1665-9.

Wen, L. et al., Limiting Dilution Assay for Human B Cells Based on Their Activation by Mutant EL4 Thymoma Cells: Total and Anti-Malaria Responder B Cell Frequencies. Eur J Immunol. 1987; 17(6):887-92.

Werner, R.G., Appropriate Mammalian Expression Systems for Biopharmaceuticals. Arzneimittelforschung. 1998; 48(8):870-80.

Windheim, M. et al., Interleukin-1 (IL-1) Induces the Lys63-linked Polyubiquitination of IL-1 Receptor-Associated Kinase 1 to Facilitate NEMO Binding and the Activation of 1-K13a Kinase. Mol Cell Biol. 2008; 28(5):1783-91.

Wood, K.V., Firefly Luciferase: A New Tool for Molecular Biologists. Promega Notes. 1990; 28:1-3.

Yamane-Ohnuki, N. and Satoh, M., Production of Therapeutic Antibodies with Controlled Fucosylation. MAbs. 2009; 1(3):230-6.

Yelton, D.E. et al., Affinity Maturation of the BR96 Anti-Carcinoma Antibody by Codon-Based Mutagenesis. J Immunol. 1995; 155(4):1994-2004.

Yoon, D.-Y. and Dinarello, C.A., Antibodies to Domains II and III of the IL-1 Receptor Accessory Protein Inhibit IL-1R Activity But Not Binding: Regulation of IL-1 Responses Is Via Type I Receptor, Not the Accessory Protein. J Immunol. 1998; 160:3170-9.

Yoon, D.-Y. and Dinarello, C.A., Differential Effects of Anti-IL-1 R Accessory Protein Antibodies on IL-1a or IL-1 R-induced Production of PGE(2) and IL-6 from 3T3-L1 Cells. J Biochem Mol Biol. 2007; 40(4): 562-70.

Zhao et al., Construction of hydridoma calls with ILIRAP as a new marker for leukemia stem cells and detection of its monoclonal antibody, Journal of Exp Hematology, 2013, 21(6): 1390-1393.

Zubler, Polyclonal B Cell Responses in the Presence of Defined Filler Cells: Complementary Effects of Lipopolysaccharide and Anti-Immunoglobulin Antibodies, Eur J Immunol., 1984, 14(4): 357-363.

Fig. 1: Sequences (amino acids in one letter code)

| | |
|---|---|
| VH complete: | SEQ ID NO: 1-34 and SEQ ID NO: 173 and 176 |
| VL complete: | SEQ ID NO: 35-68 and SEQ ID NO: 174 and 177 |
| | |
| CDR-H1: | SEQ ID NO: 69-85 and 178 |
| CDR-H2: | SEQ ID NO: 86-102 and 179 |
| CDR-H3: | SEQ ID NO: 103-119 and 180 |
| | |
| CDR-L1: | SEQ ID NO: 120-136 and 181 |
| CDR-L2: | SEQ ID NO: 137-153 and 182 |
| CDR-L3: | SEQ ID NO: 154-170 and 175 and 183 |
| | |
| CR-L: | SEQ ID NO: 171 |
| CR-H: | SEQ ID NO: 172 |

| mAB name | SEQ ID NO. | Complete Heavy-chain VR sequence |
|---|---|---|
| MAB-15-0139 | 1 | EVQLEESGGGLVQPGGSLRLSCAASGFSFSSSYWICWVRQAPGKGLEWVSCIYTGSGGTYYASWEKGRFTISRDNSKNTLYLQMNSLRAEDTAVYFCARDPGYSSWLWGQGTLVTVSS |
| MAB-15-0106 | 2 | EVQLEESGGDLVQPGGSLRLSCAASGFSFSSSHYMCWVRQAPGKGLEWVSCIYAGSSGNTYYANWAKGRFTISRDNSKNTLYLQMNSLRAEDTAVYFCARVDASSSGSWDLWGQGTLVTVSS |
| MAB-15-0108 | 3 | EVQLEESGGRLVQPGGSLRLSCAVSGIDLSSYAMGWVRQAPGKGLEYVSVITSSATTYYASWAKGRFTISRDNSKNTLYLQMNSLRAEDTAVYFCARGGPGYSTNTHYAFDPWGQGTLVTVSS |
| MAB-15-0110 | 4 | EVQLEESGGRVVQPGRSLRLSCAVSGIDLDNYAMGWVRQAPGKGLEYVAVISSDGFFYDASWAKGRFTISRDNSKNTLYLQMNSLRAEDTAVYFCARDRGTSTGSLDLWGQGTLVTVSS |
| MAB-15-0117 | 5 | EVQLEESGGRLVQPGGSLRLSCAASGFSLSSYYMSWVRQAPGKGLEWVSIISGSASTYYATWAKGRFTISRDNSKNTLYLQMNSLRAEDTAVYFCARTHYAAVAGYGYASRLDLWGQGTLVTVSS |
| MAB-15-0121 | 6 | EVQLEESGGDLVQPGGSLRLSCAASGFSFSSNYWICWVRQAPGKGLELVSCIYTSTGNTWYASWAKGRFTISRDNSKNTLYLQMNSLRAEDTAVYFCARDLLVVTSFNLWGQGTLVTVSS |
| MAB-15-0140 | 7 | EVQLEESGGDLVQPGGSLRLSCAASGFSFSSSYYMCWVRQAPGKGLEWVSCIYAGSSGVTYYASWAKGRFTISRDNSKNTLYLQMNSLRAEDTAVYFCASETDGNYFNLWGQGTLVTVSS |
| MAB-15-0115 | 8 | EVQLEQSGGGLVQPGGSLRLSCAASGFSLSTSYWRCWVRQAPGKGLEWVSCIYAGSGDVTYYANWVNGRFTISRDNSKNTLYLQMNSLRAEDTAVYYCASGVGFGYFNLWGQGTLVTVSS |

| | | |
|---|---|---|
| MAB-15-0125 | 9 | EVQLEESGGGLVQPGGSLRLSCAASGIDFSSYYYMCWVRQAPGKGLEWVSCIFIGYGDVTWYASWAKGRFTISRDNSKNTLYLQMNSLRAEDTAVYFCARALGSSGYRVNLWGQGTLVTVSS |
| MAB-15-0119 | 10 | EVQLEESGGRLVQPGGSLRLSCAASGFSLSSYWMSWVRQAPGKGLEWVSMIYGSGYTYYASWAKGRFTISRDNSKNTLYLQMNSLRAEDTAVYFCARDPQYFILWGQGTLVTVSS |
| MAB-15-0109 | 11 | EVQLEESGGRLVQPGGSLRLSCAVSGFSLSSYDMSWVRQAPGKGLEWVSTIYIGGTTAYASWPKGRFTISRDNSKNTLYLQMNSLRAEDTAVYFCARLQGANYYNSLALWGQGTLVTVSS |
| MAB-15-0097 | 12 | EVQLVESGGGLVQPGGSLRLSCAASGFDFSSNYYMCWVRQAPGKGLELVSCIYTNSGNTWSASWAKGRFTISRDNSKNTLYLQMNSLRAEDTAVYFCARDLNYPDTSNLWGQGTLVTVSS |
| MAB-15-0135 | 13 | EVQLEESGGDLVQPGGSLRLSCAASGFSFSFGYYMCWVRQAPGKGLEWVSCIYGDSSDTLYANWAKGRFTISRDNSKNTLYLQMNSLRAEDTAVYFCARYPGGSYYNLWGQGTLVTVSS |
| MAB-15-0133 | 14 | EVQLEESGGDLVQPGGSLRLSCAASGFSFSSTYYMCWVRQAPGKGLEWVSCIYAGSSGSTYYASWAKGRFTISRDNSKNTLYLQMNSLRAEDTAVYFCARVDGSSSGSWDLWGQGTLVTVSS |
| MAB-15-0107 | 15 | EVQLEESGGDLVQPGGSLRLSCAASGISFSSSDFMCWVRQAPGKGLEWVSCIYAGSSVSIYYATWAKGRFTISRDNSKNTLYLQMNSLRAEDTAVYFCARSTGSVGRGFNLWGQGTLVTVSS |
| MAB-15-0128 | 16 | EVQLVESGGGLVQPGGSLRLSCAASGFSFSSIYYMCWVRQAPGKGLEWVSCIYTGNSDFTYYANWAKGRFTISRDNSKNTLYLQMNSLRAEDTAVYFCARFRDDYASLKLWGQGTLVTVSS |
| MAB-15-0116 | 17 | EVQLEESGGGLVQPGGSLRLSCAASGFSFSSGYDMCWVRQAPGKGLEWVSCIYTGSGSTYYANWAKGRFTISRDNSKNTLYLQMNSLRAEDTAVYFCARNSNDWMYFNLWGQGTLVTVSS |
| MAB-16-0004 | 18 | EVQLEQSGGGLVQPGGSLRLSCAASGFSFSSSYWICWVRQAPGKGLEWVACIYTGSGGTYYASWEKGRFTISKTSSTTLYLQMNSLRAEDTAVYFCARDPGYSSWLWGQGTLVTVSS |
| MAB-16-0009 | 19 | EVQLEESGGDLVQPGASLRLSCAASGFSFSSSHYMCWVRQAPGKGLEWVACIYAGSSGNTYYANWAKGRFTISKTNSKNTLYLQMNSLRAEDTAVYFCARVDASSSGSWDLWGQGTLVTVSS |
| MAB-16-0028 | 20 | EVQLLESGGRLVQPGTSLRLSCAVSGIDLSSYAMGWVRQAPGKGLEYVGVITSSATTYYASWAKGRFTISKTSSTTLYLQMNSLRAEDTAVYFCARGGPGYSTNTHYAFDPWGQGTLVTVSS |
| MAB-16-0031 | 21 | EVQLEESGGRVVQPGTSLRLSCAVSGIDLDNYAMGWVRQAPGKGLEYVAVISSDGFFYDASWAKGRFTISKANSKNTLYLQMNSLRAEDTAVYFCARDRGTSTGSLDLWGQGTLVTVSS |

Fig. 1 (cont.)

| | | |
|---|---|---|
| MAB-16-0043 | 22 | QVQLEESGGRLVQPGTSLRLSCAASGFSLSSYYMSWVRQAPGKGLEWVAIISGSASTYYA TWAKGRFTISKTSTTLYLQMNSLRAEDTAVYFCARTHYAAVAGYGYASRLDLWGQGTLV TVSS |
| MAB-16-0049 | 23 | QVQLQESGGDLVQPGGSLRLSCAASGFSFSSNYWICWVRQAPGKGLELVACIYTSTGNT WYASWAKGRFTISRDNSKNTLYLQMNSLRAEDTAVYFCARDLLVVTSFNLWGQGTLVTV SS |
| MAB-16-0045 | 24 | EVQLVESGGDLVQPGASLRLSCAASGFSFSSSYYMCWVRQAPGKGLEWVACIYAGSSGV TYYASWAKGRFTISDTSSTTLYLQMNSLRAEDTAVYFCASETDGNYFNLWGQGTLVTVSS |
| MAB-16-0040 | 25 | EVQLEQSGGGLVQPGGSLRLSCAASGFSLSTSYWRCWVRQAPGKGLEWVACIYAGSGD VTYYANWVNGRFTISRDNSKSTLYLQMNSLRAEDTAVYYCASGVGFGYFNLWGQGTLVT VSS |
| MAB-16-0036 | 26 | EVQLEESGGGLVQPGGSLRLSCAASGIDFSSYYYMCWVRQAPGKGLEWVACIFIGYGDVT WYASWAKGRFTISKANSKNTLYLQMNSLRAEDTAVYFCARALGSSGYRVNLWGQGTLV TVSS |
| MAB-16-0046 | 27 | QVQLEESGGRLVQPGASLRLSCAASGFSLSSYWMSWVRQAPGKGLEWVAMIYGSGYTY YASWAKGRFTISTTSTTLYLQMNSLRAEDTAVYFCARDPQYFILWGQGTLVTVSS |
| MAB-16-0030 | 28 | EVQLEESGGRLVQPGTSLRLSCAVSGFSLSSYDMSWVRQAPGKGLEWVSTIYIGGTTAYA SWPKGRFTISKTNSKNTLYLQMNSLRAEDTAVYFCARLQGANYYNSLALWGQGTLVTVS S |
| MAB-16-0021 | 29 | QVQLVESGGGLVQPGGSLRLSCAASGFDFSSNYYMCWVRQAPGKGLELVACIYTNSGNT WSASWAKGRFTISKTNSTTLYLQMNSLRAEDTAVYFCARDLNYPDTSNLWGQGTLVTVS S |
| MAB-16-0019 | 30 | EVQLEESGGDLVQPGGSLRLSCAASGFSFSFGYYMCWVRQAPGKGLEWVACIYGDSSDT LYANWAKGRFTISKTNSKNTLYLQMNSLRAEDTAVYFCARYPGGSYYNLWGQGTLVTVS S |
| MAB-16-0015 | 31 | QVQLQESGGDLVQPGASLRLSCAASGFSFSSTYYMCWVRQAPGKGLEWVACIYAGSSGS TYYASWAKGRFTISKNSSTLYLQMNSLRAEDTAVYFCARVDGSSSGSWDLWGQGTLVTV SS |
| MAB-16-0027 | 32 | EVQLEESGGDLVQPGASLRLSCAASGISFSSSDFMCWVRQAPGKGLEWVACIYAGSSVSI YYATWAKGRFTISKASSTTLYLQMNSLRAEDTAVYFCARSTGSVGRGFNLWGQGTLVTVS S |
| MAB-16-0048 | 33 | EVQLVESGGGLVQPGGSLRLSCAASGFSFSSIYYMCWVRQAPGKGLEWVGCIYTGNSDF TYYANWAKGRFTISRDNSKSTLYLQMNSLRAEDTAVYFCARFRDDYASLKLWGQGTLVT VSS |
| MAB-16-0041 | 34 | QVQLQESGGGLVQPGGSLRLSCTASGFSFSSGYDMCWVRQAPGKGLEWVGCIYTGSGS TYYANWAKGRFTISKDNSKTTLYLQMNSLRAEDTAVYFCARNSNDWMYFNLWGQGTLV TVSS |

Fig. 1 (cont.)

| mAb Name | SEQ ID NO. | Complete k-Light chain VR sequence |
|---|---|---|
| MAB-15-0139 | 35 | DIVMTQSPSSLSASVGDRVTITCQASESISNYLSWYQQKPGQAPKLLIYLASTLASGVPSRFSGSGSGTDFTLTISSLQPEDFATYYCQNWWVIEHNGAAFGGGTKVVIK |
| MAB-15-0106 | 36 | DIQMTQSPSSLSASVGDRVTITCQASESIYSNLAWYQQKPGQAPKLLIYAASLLASGVPSRFSGSGSGTDFTLTISSLQPEDFATYYCQSASYSTGPDWTFGQGTKVVIK |
| MAB-15-0108 | 37 | DIQMTQSPSSLSASVGDRVTITCQASQSIYIYLSWYQQKPGQAPKLLIYDASKLASGVPSRFSGSGSGTDFTLTISSLQPEDFATYYCQQGATTYNVDNVFGQGTKVVIK |
| MAB-15-0110 | 38 | DIVMTQSPSSLSASVGDRVTITCQASENIGNGLAWYQQKPGQAPKLLIYGASTLASGVPSRFSGSGSGTDFTLTISSLQPEDFATYYCQCTYWNPDYIGGAFGGGTKVVIK |
| MAB-15-0117 | 39 | DIQMTQSPSSLSASVGDRVTITCLASEDIYSGISWYQQKPGKAPKLLIYAASNLESGVPSRFSGSGSGTDFTLTISSLQPEDFATYYCLGGYSYSNTGPTFGQGTKVEIK |
| MAB-15-0121 | 40 | DIVMTQSPSSLSASVGDRVTITCQASEDIYSNLAWFQQKPGQAPKLLIYGASTLASGVPSRFSGSGSGTEFTLTISSLQPEDFATYYCLGVCTDISTDDLYNAFGQGTKVVIK |
| MAB-15-0140 | 41 | DIVMTQSPSSLSASVGDRVTITCQASEDIYSNLAWFQQKPGQAPKLLIYRASTLASGVPSRFSGSGSGTEFTLTISSLQPEDFATYYCLGVYTYSTDIHAFGGGTKVVIK |
| MAB-15-0115 | 42 | DIVMTQSPSSLSASVGDRVTITCQASEDIYSNLAWFQQKPGQAPKLLIYDASTLASGVPSRFSGSGSGTEFTLTISSLQPEDFATYYCLGVYTHISADNAFGGGTKVVIK |
| MAB-15-0125 | 43 | DIQMTQSPSSLSASVGDRVTITCQASENIYSSLAWYQQKPGQAPKLLIYDASDLASGVPSRFSGSGSGTDFTLTISSLQPEDFATYYCQQGYYSGGTDNDVFGGGTKVVIK |
| MAB-15-0119 | 44 | DIVMTQSPSSLSASVGDRVTITCQSSQSVDGNNLLSWYQQKPGQAPKLLIYDASNLASGVPSRFSGSGSGTDFTLTISSLQPEDFATYYCQGSYYSSSWYNVFGQGTKVVIK |
| MAB-15-0109 | 45 | DIQMTQSPSSLSASVGDRVTITCQASQSIYSFLSWYQQKPGQAPKLLIYAASDLESGVPSRFSGSGSGTDFTLTISSLQPEDFATYYCQCNYIIDYGAFGQGTKVVIK |
| MAB-15-0097 | 46 | DIQMTQSPSSLSASVGDRVTITCQASQSIGYYLAWYQQKPGQAPKLLIYRASTLASGVPSRFSGSGSGTDFTLTISSLQPEDFATYYCQSYYNSDSDAFGQGTKVVIK |
| MAB-15-0135 | 47 | DIVMTQSPSSLSASVGDRVTITCQASQTISINLAWYQQKPGQAPKLLIYYASTLASGVPSRFSGSGSGTDFTLTISSLQPEDFATYYCQQGYTEDNIDNTFGQGTKVVIK |
| MAB-15-0133 | 48 | DIQMTQSPSSLSASVGDRVTITCQASQNIYSNLAWYQQKPGQAPKLLIYAASLLASGVPSRFSGSGSGTDFTLTISSLQPEDFATYYCQGAVYSGNTEWAFGQGTKVVIK |
| MAB-15-0107 | 49 | DIVMTQSPSSLSASVGDRVTITCQASQSVYNSNHLSWYQQKPGQAPKLLIYSASTLASGVPSRFSGSGSGTDFTLTISSLQPEDFATYYCQGEFSCVSADCIAFGGGTKVVIK |

Fig. 1 (cont.)

| MAB-15-0128 | 50 | DIQMTQSPSSLSASVGDRVTITCQASQSISSYLSWYQQKPGQAPKLLIYGASNLASGVPSR FSGSGSGTDFTLTISSLQPEDFATYYCQCTYYDNNYGGAFGGGTKVVIK |
|---|---|---|
| MAB-15-0116 | 51 | DIVMTQSPSSLSASVGDRVTITCQASESISANYWSWYQQKPGQAPKLLIYGASTLASGVPS RFSGSGSGTDFTLTISSLQPEDFATYFCQSWYYSGSGSYHSWAFGQGTKVVIK |
| MAB-16-0004 | 52 | DIVMTQSPSSLSASVGDRVTITCQASESISNYLSWYQQKPGQAPKLLIYLASTLASGVPSRF SGSGSGTDFTLTISSLQPEDFATYYCQNWWVIEHNGAAFGGGTKVVIK |
| MAB-16-0009 | 53 | AIQMTQSPSSLSASVGDRVTITCQASESIYSNLAWYQQKPGQAPKLLIYAASLLASGVPSRF SGSGSGTDYTLTISSLQPEDFATYYCQSASYSTGPDWTFGQGTKVVIK |
| MAB-16-0028 | 54 | AIRMTQSPSSLSASVGDRVTITCQASQSIYIYLSWYQQKPGQAPKLLIYDASKLASGVPSRF SGSGSGTDFTLTISSLQPEDFATYYCQQGATTYNVDNVFGQGTKVVIK |
| MAB-16-0031 | 55 | ELVMTQSPSSLSASVGDRVTITCQASENIGNGLAWYQQKPGQAPKLLIYGASTLASGVPS RFSGSGSGTDFTLTISSLQPEDFATYYCQCTYWNPDYIGGAFGGGTKVVIK |
| MAB-16-0043 | 56 | AIQMTQSPSSLSASVGDRVTITCLASEDIYSGISWYQQKPGKAPKLLIYAASNLESGVPSRFS GSGSGTDYTLTISSLQPEDFATYYCLGGYSYSNTGPTFGQGTKVEIK |
| MAB-16-0049 | 57 | DIVMTQSPSSLSASVGDRVTITCQASEDIYSNLAWFQQKPGQAPKLLIYGASTLASGVPSR FSGSGSGTEFTLTISSLQPEDFATYYCLGVCTDISTDDLYNAFGQGTKVVIK |
| MAB-16-0045 | 58 | DIVMTQSPSSLSASVGDRVTITCQASEDIYSNLAWFQQKPGQAPKLLIYRASTLASGVPSR FSGSGSGTEFTLTISSLQPEDFATYYCLGVYTYSTDIHAFGGGTKVVIK |
| MAB-16-0040 | 59 | ELVMTQSPSSLSASVGDRVTITCQASEDIYSNLAWFQQKPGQAPKLLIYDASTLASGVPSR FSGSGSGTEFTLTISSLQPEDFATYYCLGVYTHISADNAFGGGTKVEIK |
| MAB-16-0036 | 60 | ALQMTQSPSSLSASVGDRVTITCQASENIYSSLAWYQQKPGQAPKLLIYDASDLASGVPSR FSGSGSGTDFTLTISSLQPEDFATYYCQQGYYSGGTDNDVFGGGTKVVIK |
| MAB-16-0046 | 61 | NIVMTQSPSSLSASVGDRVTITCQSSQSVDGNNLLSWYQQKPGQAPKLLIYDASNLASGV PSRFSGSGSGTDFTLTISSLQPEDFATYYCQGSYYSSSWYNVFGQGTKVVIK |
| MAB-16-0030 | 62 | DVQMTQSPSSLSASVGDRVTITCQASQSIYSFLSWYQQKPGQAPKLLIYAASDLESGVPSR FSGSGSGTDFTLTISSLQPEDFATYYCQCNYIIDYGAFGQGTKVVIK |
| MAB-16-0021 | 63 | DIQMTQSPSSLSASVGDRVTITCQASQSIGYYLAWYQQKPGQAPKLLIYRASTLASGVPSR FSGSGSGTDFTLTISSLQPEDFATYYCQSYYNSDSDAFGQGTKVVIK |
| MAB-16-0019 | 64 | AIVMTQSPSSLSASVGDRVTITCQASQTISINLAWYQQKPGQAPKLLIYYASTLASGVPSRF SGSGSGTDFTLTISSLQPEDFATYYCQQGYTEDNIDNTFGQGTKVVIK |
| MAB-16-0015 | 65 | AIQMTQSPSSLSASVGDRVTITCQASQNIYSNLAWYQQKPGQAPKLLIYAASLLASGVPSR FSGSGSGTDYTLTISSLQPEDFATYYCQGAVYSGNTEWAFGQGTKVVIK |
| MAB-16-0027 | 66 | DIVMTQSPSSLSASVGDRVTITCQASQSVYNSNHLSWYQQKPGQAPKLLIYSASTLASGVP SRFSGSGSGTDFTLTISSLQPEDFATYYCQGEFSCVSADCIAFGGGTKVVIK |

Fig. 1 (cont.)

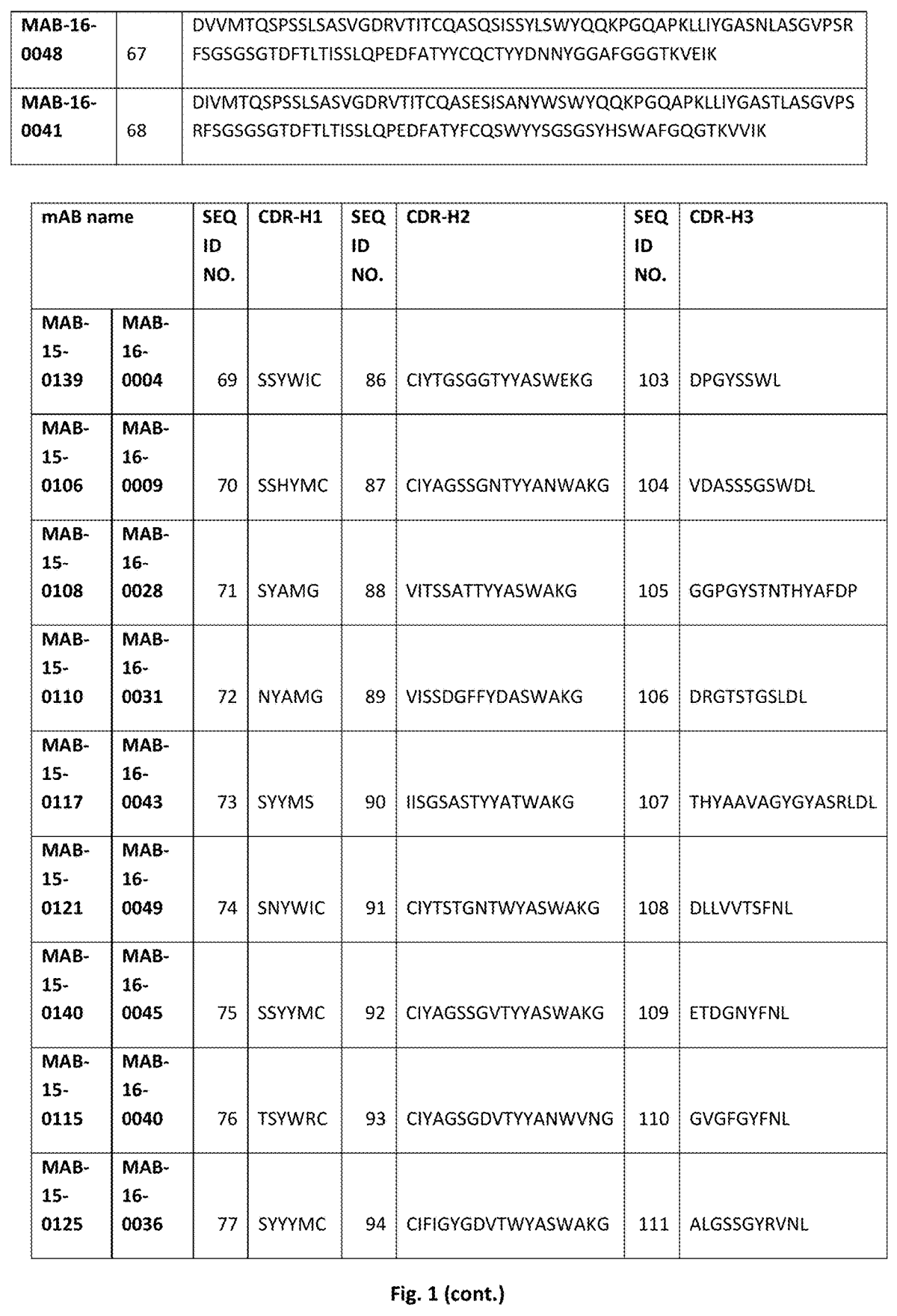

| MAB-16-0048 | 67 | DVVMTQSPSSLSASVGDRVTITCQASQSISSYLSWYQQKPGQAPKLLIYGASNLASGVPSR FSGSGSGTDFTLTISSLQPEDFATYYCQCTYYDNNYGGAFGGGTKVEIK |
| MAB-16-0041 | 68 | DIVMTQSPSSLSASVGDRVTITCQASESISANYWSWYQQKPGQAPKLLIYGASTLASGVPS RFSGSGSGTDFTLTISSLQPEDFATYFCQSWYYSGSGSYHSWAFGQGTKVVIK |

| mAB name | | SEQ ID NO. | CDR-H1 | SEQ ID NO. | CDR-H2 | SEQ ID NO. | CDR-H3 |
|---|---|---|---|---|---|---|---|
| MAB-15-0139 | MAB-16-0004 | 69 | SSYWIC | 86 | CIYTGSGGTYYASWEKG | 103 | DPGYSSWL |
| MAB-15-0106 | MAB-16-0009 | 70 | SSHYMC | 87 | CIYAGSSGNTYYANWAKG | 104 | VDASSSGSWDL |
| MAB-15-0108 | MAB-16-0028 | 71 | SYAMG | 88 | VITSSATTYYASWAKG | 105 | GGPGYSTNTHYAFDP |
| MAB-15-0110 | MAB-16-0031 | 72 | NYAMG | 89 | VISSDGFFYDASWAKG | 106 | DRGTSTGSLDL |
| MAB-15-0117 | MAB-16-0043 | 73 | SYYMS | 90 | IISGSASTYYATWAKG | 107 | THYAAVAGYGYASRLDL |
| MAB-15-0121 | MAB-16-0049 | 74 | SNYWIC | 91 | CIYTSTGNTWYASWAKG | 108 | DLLVVTSFNL |
| MAB-15-0140 | MAB-16-0045 | 75 | SSYYMC | 92 | CIYAGSSGVTYYASWAKG | 109 | ETDGNYFNL |
| MAB-15-0115 | MAB-16-0040 | 76 | TSYWRC | 93 | CIYAGSGDVTYYANWVNG | 110 | GVGFGYFNL |
| MAB-15-0125 | MAB-16-0036 | 77 | SYYYMC | 94 | CIFIGYGDVTWYASWAKG | 111 | ALGSSGYRVNL |

Fig. 1 (cont.)

| mAB name | | | CDR-H1 | | CDR-H2 | | CDR-H3 |
|---|---|---|---|---|---|---|---|
| MAB-15-0119 | MAB-16-0046 | 78 | SYWMS | 95 | MIYGSGYTYYASWAKG | 112 | DPQYFIL |
| MAB-15-0109 | MAB-16-0030 | 79 | SYDMS | 96 | TIYIGGTTAYASWPKG | 113 | LQGANYYNSLAL |
| MAB-15-0097 | MAB-16-0021 | 80 | SNYYMC | 97 | CIYTNSGNTWSASWAKG | 114 | DLNYPDTSNL |
| MAB-15-0135 | MAB-16-0019 | 81 | FGYYMC | 98 | CIYGDSSDTLYANWAKG | 115 | YPGGSYYNL |
| MAB-15-0133 | MAB-16-0015 | 82 | STYYMC | 99 | CIYAGSSGSTYYASWAKG | 116 | VDGSSSGSWDL |
| MAB-15-0107 | MAB-16-0027 | 83 | SSDFMC | 100 | CIYAGSSVSIYYATWAKG | 117 | STGSVGRGFNL |
| | | | | | | | |
| MAB-15-0128 | MAB-16-0048 | 84 | SIYYMC | 101 | CIYTGNSDFTYYANWAKG | 118 | FRDDYASLKL |
| MAB-15-0116 | MAB-16-0041 | 85 | SGYDMC | 102 | CIYTGSGSTYYANWAKG | 119 | NSNDWMYFNL |

| mAB name | | SEQ ID NO. | CDR-L1 | SEQ ID NO. | CDR-L2 | SEQ ID NO. | CDR-L3 |
|---|---|---|---|---|---|---|---|
| MAB-15-0139 | MAB-16-0004 | 120 | QASESISNYLS | 137 | LASTLAS | 154 | QNWWVIEHNGAA |
| MAB-15-0106 | MAB-16-0009 | 121 | QASESIYSNLA | 138 | AASLLAS | 155 | QSASYSTGPDWT |

Fig. 1 (cont.)

| | | | | | | | |
|---|---|---|---|---|---|---|---|
| MAB-15-0108 | MAB-16-0028 | 122 | QASQSIYIYLS | 139 | DASKLAS | 156 | QQGATTYNVDNV |
| MAB-15-0110 | MAB-16-0031 | 123 | QASENIGNGLA | 140 | GASTLAS | 157 | QCTYWNPDYIGGA |
| MAB-15-0117 | MAB-16-0043 | 124 | LASEDIYSGIS | 141 | AASNLES | 158 | LGGYSYSNTGPT |
| MAB-15-0121 | MAB-16-0049 | 125 | QASEDIYSNLA | 142 | GASTLAS | 159 | LGVCTDISTDDLYNA |
| MAB-15-0140 | MAB-16-0045 | 126 | QASEDIYSNLA | 143 | RASTLAS | 160 | LGVYTYSTDIHA |
| MAB-15-0115 | MAB-16-0040 | 127 | QASEDIYSNLA | 144 | DASTLAS | 161 | LGVYTHISADNA |
| MAB-15-0125 | MAB-16-0036 | 128 | QASENIYSSLA | 145 | DASDLAS | 162 | QQGYYSGGTDNDV |
| MAB-15-0119 | MAB-16-0046 | 129 | QSSQSVDGNNLLS | 146 | DASNLAS | 163 | QGSYYSSSWYNV |
| MAB-15-0109 | MAB-16-0030 | 130 | QASQSIYSFLS | 147 | AASDLES | 164 | QCNYIIDYGA |
| MAB-15-0097 | MAB-16-0021 | 131 | QASQSIGYYLA | 148 | RASTLAS | 165 | QSYYNSDSDA |
| MAB-15-0135 | MAB-16-0019 | 132 | QASQTISINLA | 149 | YASTLAS | 166 | QQGYTEDNIDNT |
| MAB-15-0133 | MAB-16-0015 | 133 | QASQNIYSNLA | 150 | AASLLAS | 167 | QGAVYSGNTEWA |

Fig. 1 (cont.)

| MAB-15-0107 | MAB-16-0027 | 134 | QASQSVYNSNHLS | 151 | SASTLAS | 168 | QGEFSCVSADCIA |
|---|---|---|---|---|---|---|---|
| MAB-15-0128 | MAB-16-0048 | 135 | QASQSISSYLS | 152 | GASNLAS | 169 | QCTYYDNNYGGA |
| MAB-15-0116 | MAB-16-0041 | 136 | QASESISANYWS | 153 | GASTLAS | 170 | QSWYYSGSGSYHSWA |

| SEQ ID NO. | Constant region sequences (CR) |
|---|---|
| 171 | RTVAAPSVFIFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC |
| 172 | ASTKGPSVFPLAPSSKSTSGGTAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPEAAGGPSVFLFPPKPKDTLMISRTP EVTCVVVDVSHEDPEVKFNWYVDGVEVHNAKTKPREEQYNSTYRVVSVLTVLHQDWLNGKEYKCKVS NKALPAPIEKTISKAKGQPREPQVYTLPPSREEMTKNQVSLTCLVKGFYPSDIAVEWESNGQPENNYKT TPPVLDSDGSFFLYSKLTVDKSRWQQGNVFSCSVMHEALHNHYTQKSLSLSPG |

| mAB name | SEQ ID NO. | Complete Heavy-chain VR seq |
|---|---|---|
| MAB-16-0150 | 173 | EVQLLESGGRLVQPGTSLRLSCAVSGIDLSSYAMGWVRQAPGKGLEYVGVITSSATTYYAS WAKGRFTISKTSSKNTLYLQMNSLRAEDTAVYFCARGGPGYSTNTHYAFDPWGQGTLVT VSS |

| mAB name | SEQ ID NO. | Complete light-chain VR seq |
|---|---|---|
| | | |

Fig. 1 (cont.)

| MAB-16-0149 | 174 | DVQMTQSPSSLSASVGDRVTITCQASQSIYSFLSWYQQKPGQAPKLLIYAASDLESGVPSR FSGSGSGTDFTLTISSLQPEDFATYYCQSNYIIDYGAFGQGTKVVIK |
| --- | --- | --- |
| | | CDR-L3 |
| MAB-16-0149 | 175 | QSNYIIDYGA |

| mAB name | CDR-H1 SEQ ID NO. | CDR-H2 SEQ ID NO. | CDR-H3 SEQ ID NO. | CDR-L1 SEQ ID NO. | CDR-L2 SEQ ID NO. | CDR-L3 SEQ ID NO. | VH SEQ ID NO. | VL SEQ ID NO. |
| --- | --- | --- | --- | --- | --- | --- | --- | --- |
| MAB-16-0150 | 71 | 88 | 105 | 122 | 139 | 156 | 173 | 54 |
| MAB-16-0149 | 79 | 96 | 113 | 130 | 147 | 175 | 28 | 174 |

Fig. 1 (cont.)

| mAB name | SEQ ID NO. | Complete heavy-chain VR seq |
|---|---|---|
| MAB-16-0531 | 176 | QSLEESGGGLVKPEGSLTLTCKASGIDFSQDYYMCWVRQAPGKGLEWIACIYTGNDITYY ASWAKGRFTVSKTSSTTVTLQMTSLTAADTATYFCARDGGANYYFKFWGQGTLVTVSS |
| | | Complete light-chain VR seq |
| MAB-16-0531 | 177 | DIVMTQTPASVEAAVGGTVTIKCQASQSISNLLAWYQQKPGQPPKLLIYGASTLESGVPSR FKGSGSGTEFTLTISDLGSADAATYYCQNYAYSSGSWYSFGGGTEVVVK |

| MAB-16-0531 | CDR-H1 | CDR-H2 | CDR-H3 | CDR-L1 | CDR-L2 | CDR-L3 |
|---|---|---|---|---|---|---|
| SEQ ID NO. | 178 | 179 | 180 | 181 | 182 | 183 |
| | QDYYMC | CIYTGNDITYY ASWAKG | DGGANYYFKF | QASQSISNLLA | GASTLES | QNYAYSSG SWYS |

Fig. 1 (cont.)

Fig.2:    Human IL-1R3 ELISA

| Antibody ID | huIL1RaP ELISA EC50 [ng/ml] |
|---|---|
| MAB-16-0015 | 1,6 |
| MAB-16-0019 | 28,1 |
| MAB-16-0021 | 20,8 |
| MAB-16-0004 | 8,0 |
| MAB-16-0009 | 4,9 |
| MAB-16-0027 | 5,3 |
| MAB-16-0030 | 4,5 |
| MAB-16-0040 | 6,6 |
| MAB-16-0043 | 13,2 |
| MAB-16-0046 | 7,4 |
| MAB-16-0049 | 20,6 |
| MAB-16-0028 | 6,0 |
| MAB-16-0031 | 8,2 |
| MAB-16-0041 | 15,2 |
| MAB-16-0036 | 5,9 |
| MAB-16-0045 | 28,4 |
| MAB-16-0048 | 7,4 |
| Reference AF676 | 79,6 |

Fig.3: HEK293 reporter assay

| Antibody ID | HEK reporter assay (IL1b) EC50 [ng/ml] |
|---|---|
| MAB-16-0015 | 27,3 |
| MAB-16-0019 | 2,5 |
| MAB-16-0021 | 33,0 |
| MAB-16-0004 | 67,1 |
| MAB-16-0009 | 18,2 |
| MAB-16-0027 | 37,3 |
| MAB-16-0030 | 8,7 |
| MAB-16-0040 | 9,4 |
| MAB-16-0043 | 27,0 |
| MAB-16-0046 | 6,1 |
| MAB-16-0049 | 42,6 |
| MAB-16-0028 | 5,1 |
| MAB-16-0031 | 23,3 |
| MAB-16-0041 | 0,1 |
| MAB-16-0036 | 9,5 |
| MAB-16-0045 | 90,2 |
| MAB-16-0048 | 16,3 |
| Reference AF676 | 234 |

Fig. 4: NFkB luciferase reporter assay using an A549 stable cell line

| Antibody ID | Signosis NFkB A549 (IL-1b) EC50 [ng/ml] |
|---|---|
| MAB-16-0015 | + |
| MAB-16-0019 | ++ |
| MAB-16-0021 | + |
| MAB-16-0004 | ++ |
| MAB-16-0009 | +++ |
| MAB-16-0027 | ++ |
| MAB-16-0030 | +++ |
| MAB-16-0040 | + |
| MAB-16-0043 | + |
| MAB-16-0046 | +++ |
| MAB-16-0049 | + |
| MAB-16-0028 | +++ |
| MAB-16-0031 | + |
| MAB-16-0041 | + |
| MAB-16-0036 | +++ |
| MAB-16-0045 | + |
| MAB-16-0048 | + |
| Reference AF676 | + |

Fig. 5:    Cell binding analysis: Binding to IL-1R3 expressing cells

| | NIH-3T3 | A549 | HEK-293 | SK-MEL-30 |
|---|---|---|---|---|
| Antibody | MFI – fold over isotype control | | | |
| MAB-16-0019 | 1,2 | 2,7 | 3,6 | 79,0 |
| MAB-16-0030 | 0,9 | 2,4 | 2,8 | 69,7 |
| MAB-16-0040 | 1,0 | 2,6 | 3,0 | 73,7 |
| MAB-16-0036 | 1,1 | 2,0 | 3,0 | 70,6 |
| MAB-16-0149 | 1,1 | 2,4 | 3,4 | 77,7 |
| MAB-16-0150 | 1,1 | 3,2 | 4,8 | 87,1 |

Fig. 6:   Cell binding analysis: Cell binding on human-IL-1R3 high expressing cell line SK-MEL-30

| Antibody | EC50 (ng/mL) |
|---|---|
| MAB-16-0030 | 307 |
| MAB-16-0149 | 306 |

Fig. 7:   Human-IL-1R3 biochemical ELISA

| Antibody | EC50 (ng/mL) |
|---|---|
| MAB-16-0149 | 16,3 |
| MAB-16-0150 | 29,1 |

Fig. 8:   Inhibition of human IL-1a and IL-1b mediated NfKB signaling in A549-NFkB-RE-Luc cells

| | Stimulated with hIL-1a | Stimulated with hIL-1b |
|---|---|---|
| Antibody | EC50 (ng/mL) | EC50 (ng/mL) |
| MAB-16-0019 | 56 | 140 |
| MAB-16-0030 | 156 | 149 |
| MAB-16-0040 | 969 | 636 |
| MAB-16-0036 | 199 | 25 |
| MAB-16-0149 | 167 | 109 |
| MAB-16-0150 | 211 | 11 |
| AF676 | 3134 | 919 |

Fig. 9: IL-1α and IL-1β functional neutralization assay - Inhibition of human IL-1a and IL-1b mediated IL-6 release by A-549 cells

| | Stimulated with hIL-1a | Stimulated with hIL-1b |
|---|---|---|
| Antibody | EC50 (ng/mL) | EC50 (ng/mL) |
| MAB-16-0019 | 546 | 180 |
| MAB-16-0030 | 361 | 346 |
| MAB-16-0040 | 2246 | 234 |
| MAB-16-0036 | 378 | 253 |
| MAB-16-0149 | 266 | 108 |
| MAB-16-0150 | 1464 | 313 |
| AF676 | >10000 | >10000 |

Fig. 10: IL-33 functional neutralization assay - Inhibition of human IL-33 mediated NfkB-signaling in HEK-Blue-IL33™ cells

| | Stimulated with hIL33 |
|---|---|
| Antibody | EC50 (ng/mL) |
| MAB-16-0019 | 376 |
| MAB-16-0030 | 909 |
| MAB-16-0040 | 17195 |
| MAB-16-0036 | 426 |
| MAB-16-0149 | 432 |
| MAB-16-0150 | 2115 |
| AF676 | 26114 |

Fig. 11: IL-36 functional neutralization assay - Inhibition of human IL-36 mediated NfkB-signaling in HEK-293/17-IF cells

| | Stimulated with hIL36 |
|---|---|
| Antibody | EC50 (ng/mL) |
| MAB-16-0019 | 11 |
| MAB-16-0030 | 13 |
| MAB-16-0040 | 42 |
| MAB-16-0036 | 14 |
| MAB-16-0149 | 18 |
| MAB-16-0150 | 13 |
| AF676 | 502 |

Fig. 12: Neutralization of IL-1a, IL-33 and IL-36a - Neutralization of IL-1a, IL-33 and IL-36a mediated cellular cytokine release by IL-1Ra and MAB-16-0030
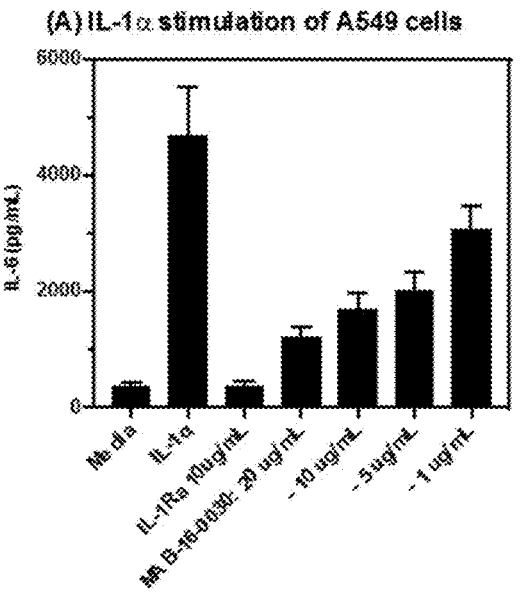
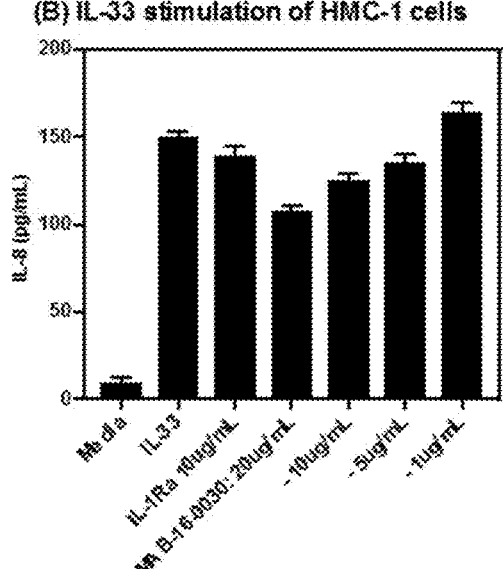
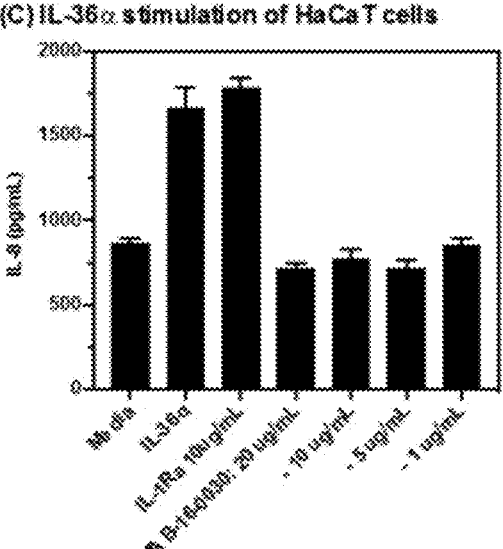

Fig. 13: Viability and IL-6 release of unstimulated PBMC treated with humanized anti-IL-1R3 IgG1-
LALA antibody MAB-16-0030
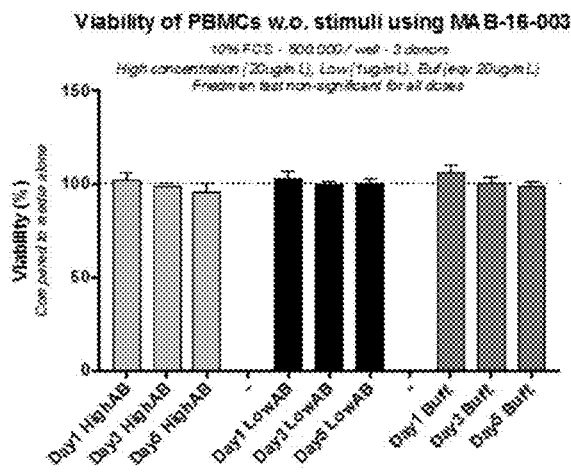
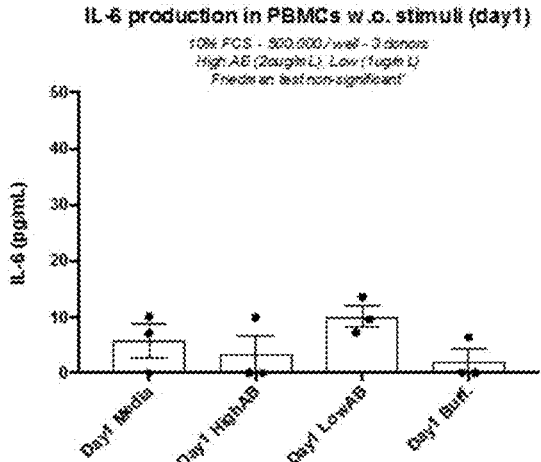
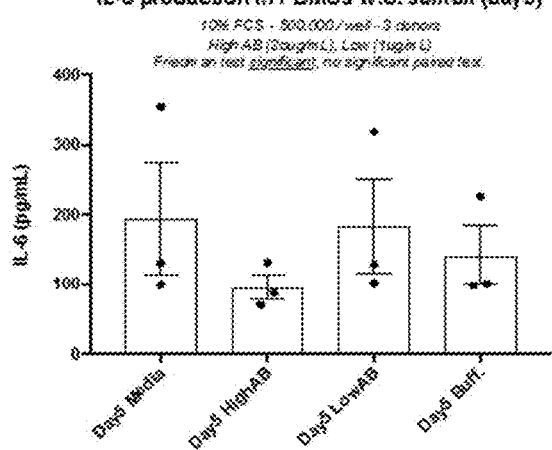

Figure 14: Functional blockage of PBMCs with different stimuli
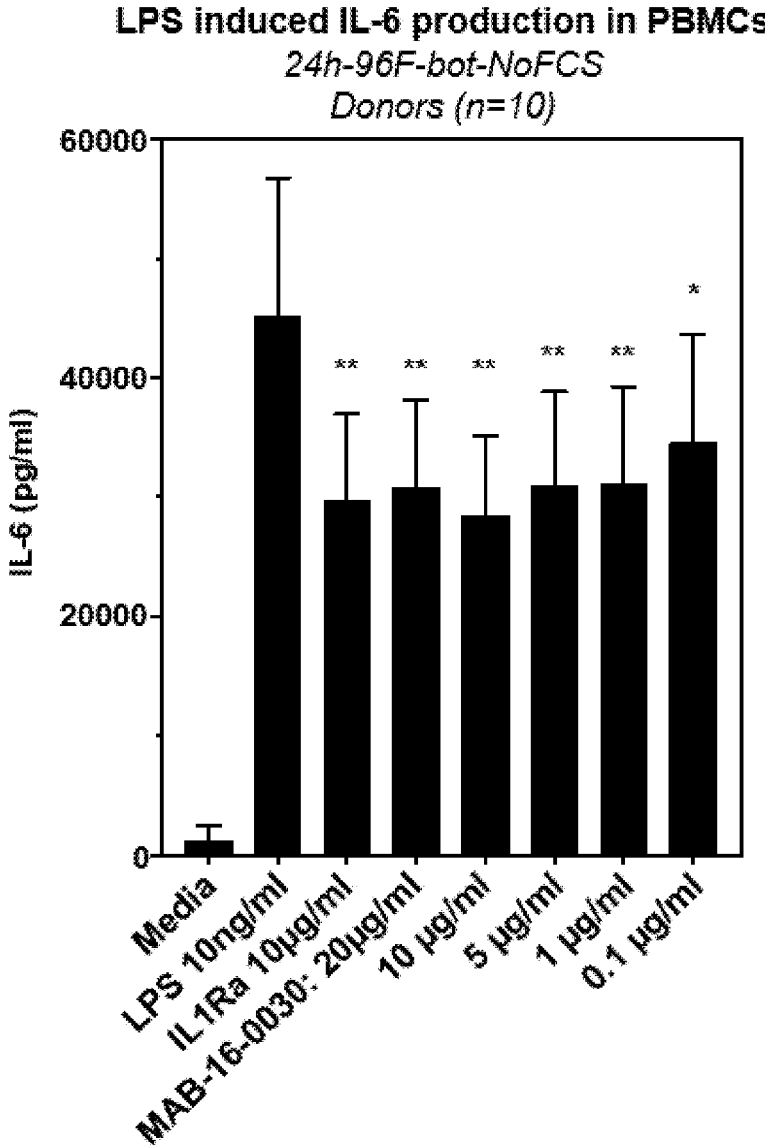

IL-12/33 induced IFN-γ production in PBMCs

CD3/28 induced IFN-γ production in PBMCs

Candida induced IL-17 production in PBMCs
*5 days-96R-bot-10%FCS*
*Donors (n=10)*

Figure 15: Functional blockage of immune cells in whole blood activated with *Candida albicans*
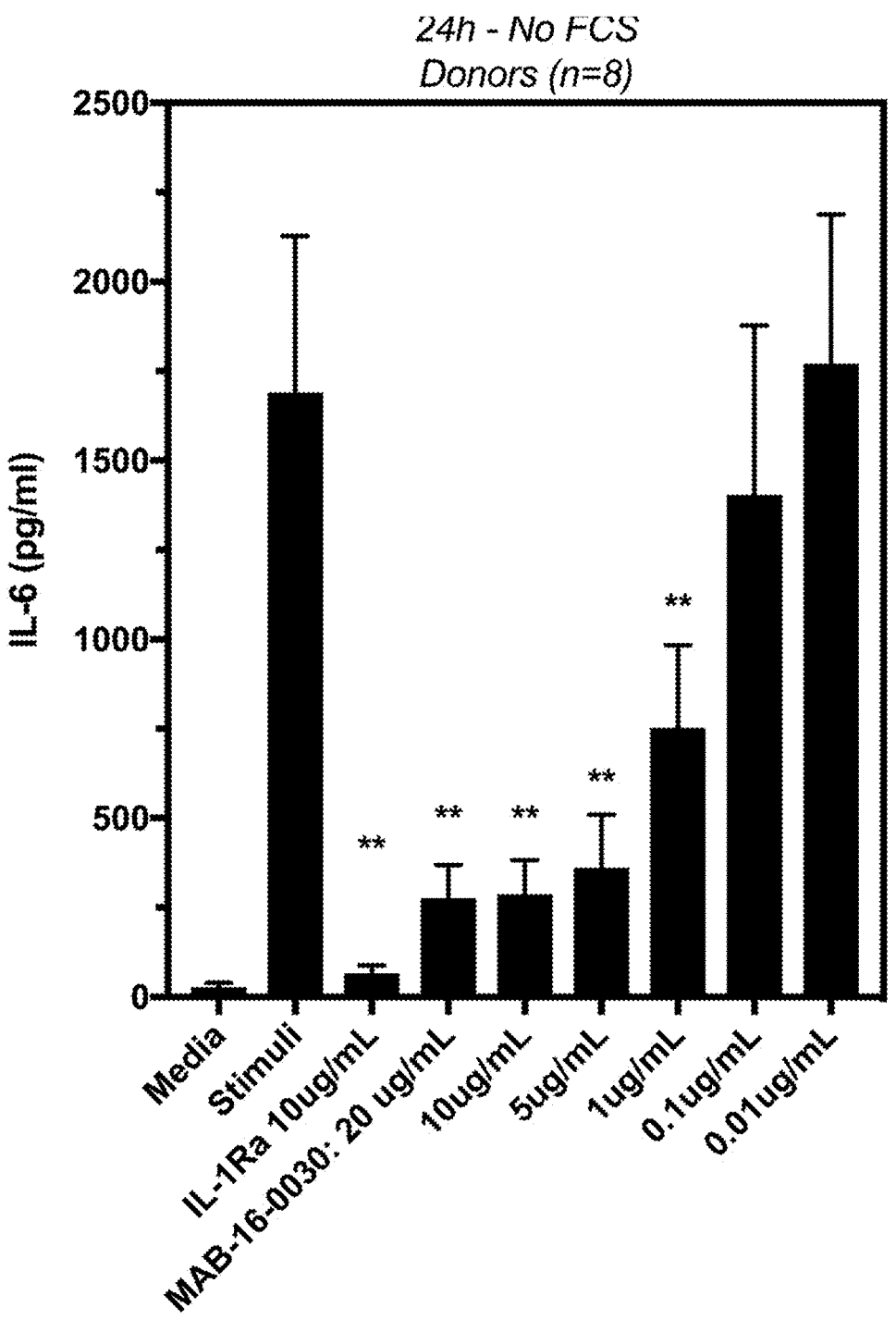

Figure 16:
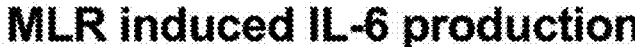
Figure 16:
Figure 16:
Figure 16:
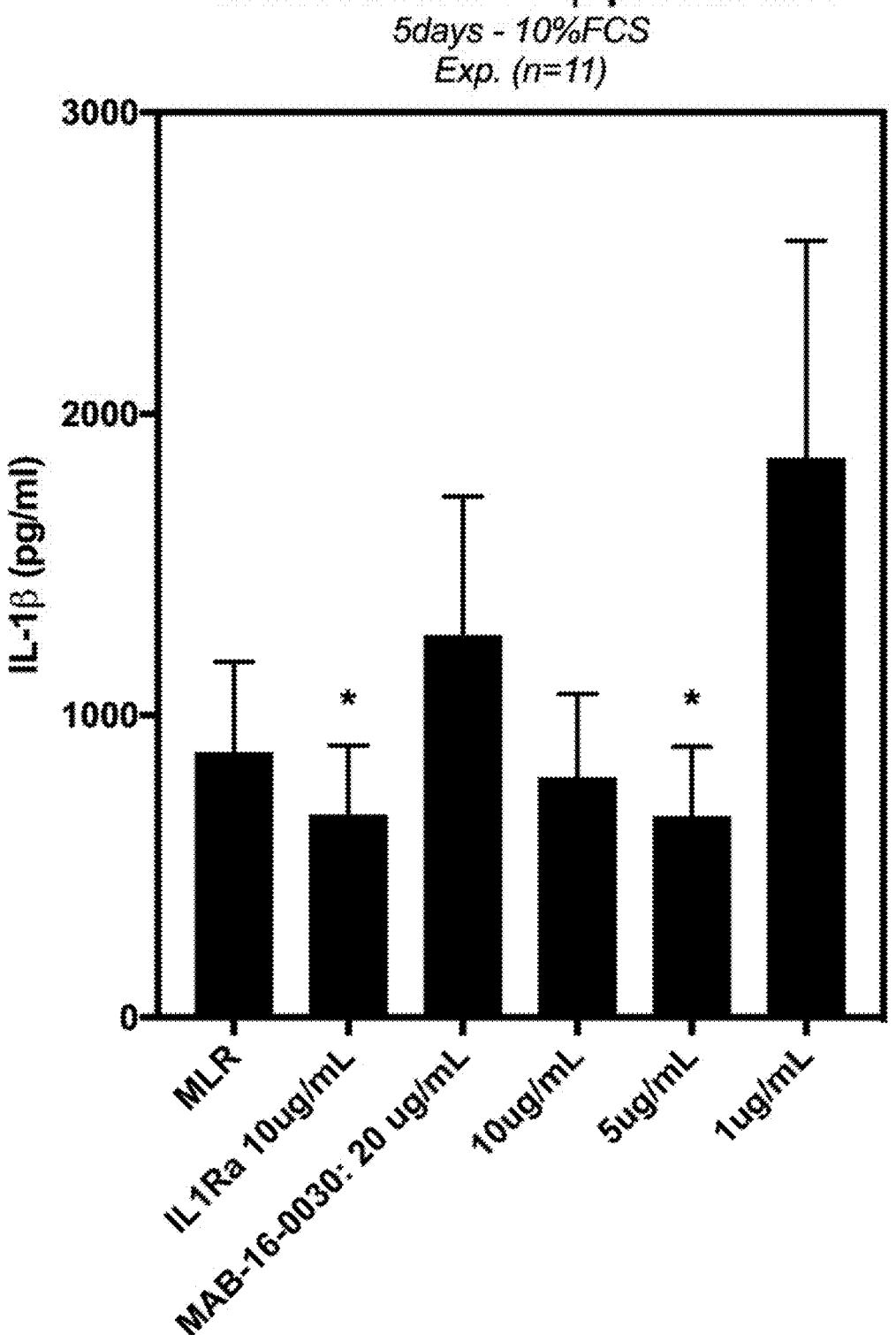
Figure 16:
Figure 16:
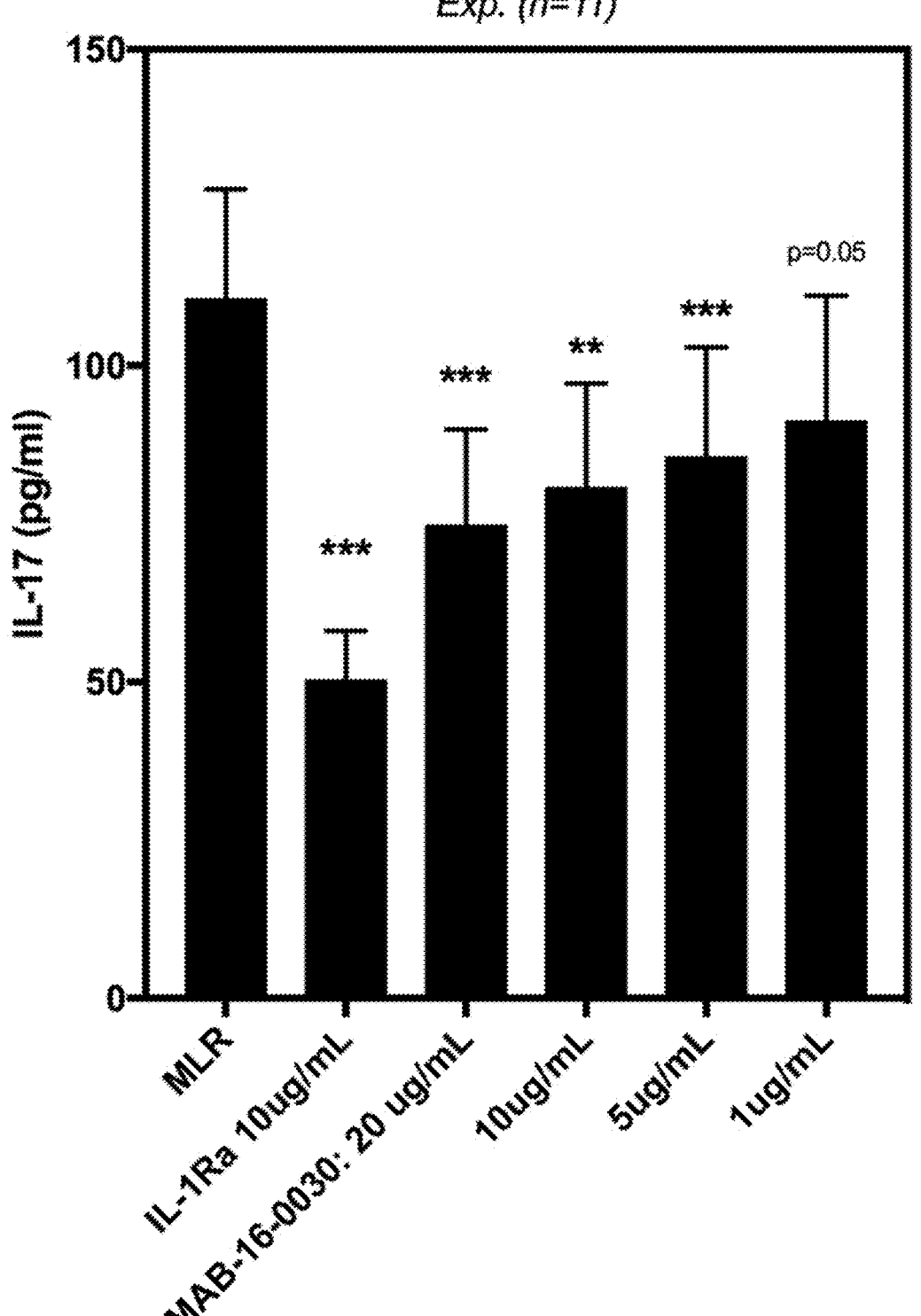
Figure 16:

Figure 16: Blockage of cytokine release in Mixed Lymphocyte Reactions (MLR)

MLR induced IL-6 production
*5days - 10%FCS*
*Exp. (n=11)*

MLR induced IL-13 production
*5days - 10%FCS*
*Exp. (n=11)*

MLR induced IL-10 production
*5days - 10%FCS*
*Exp. (n=11)*

Figure 17: Neutralization of IL-1b mediated signaling in murine cells
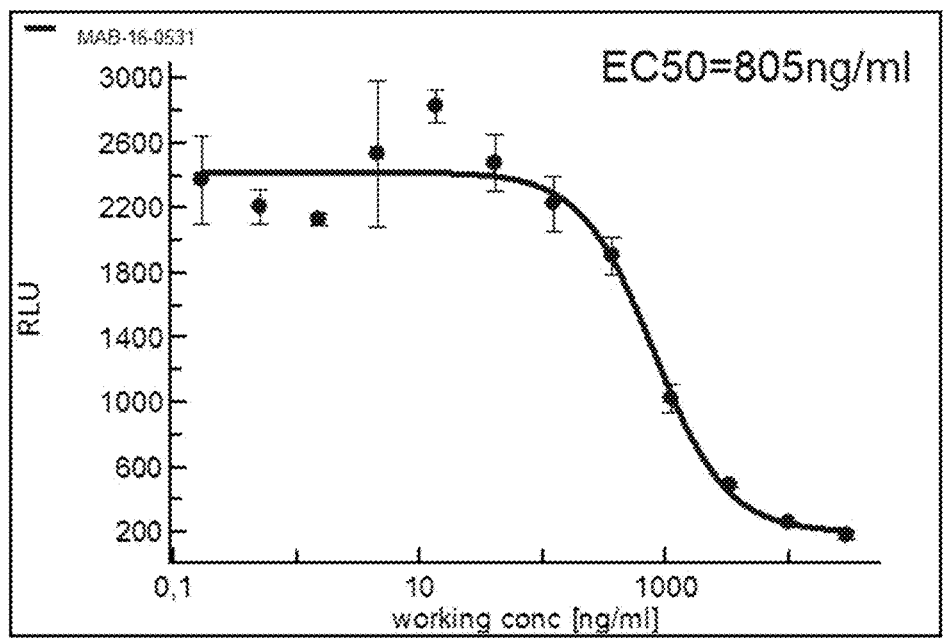
Figure 18: Neutralization of IL-1b mediated IL-6 release from murine cells
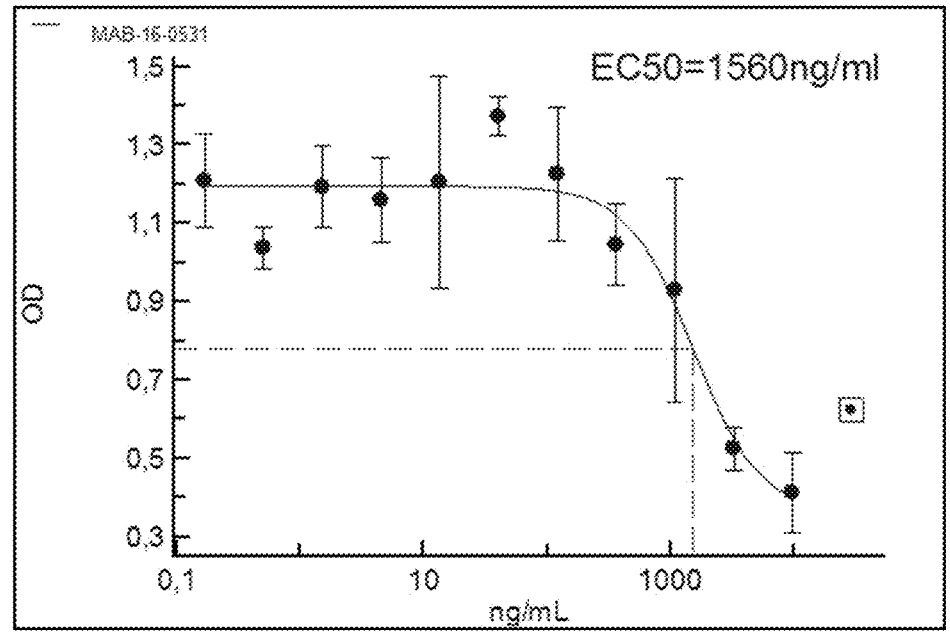

Figure 19:
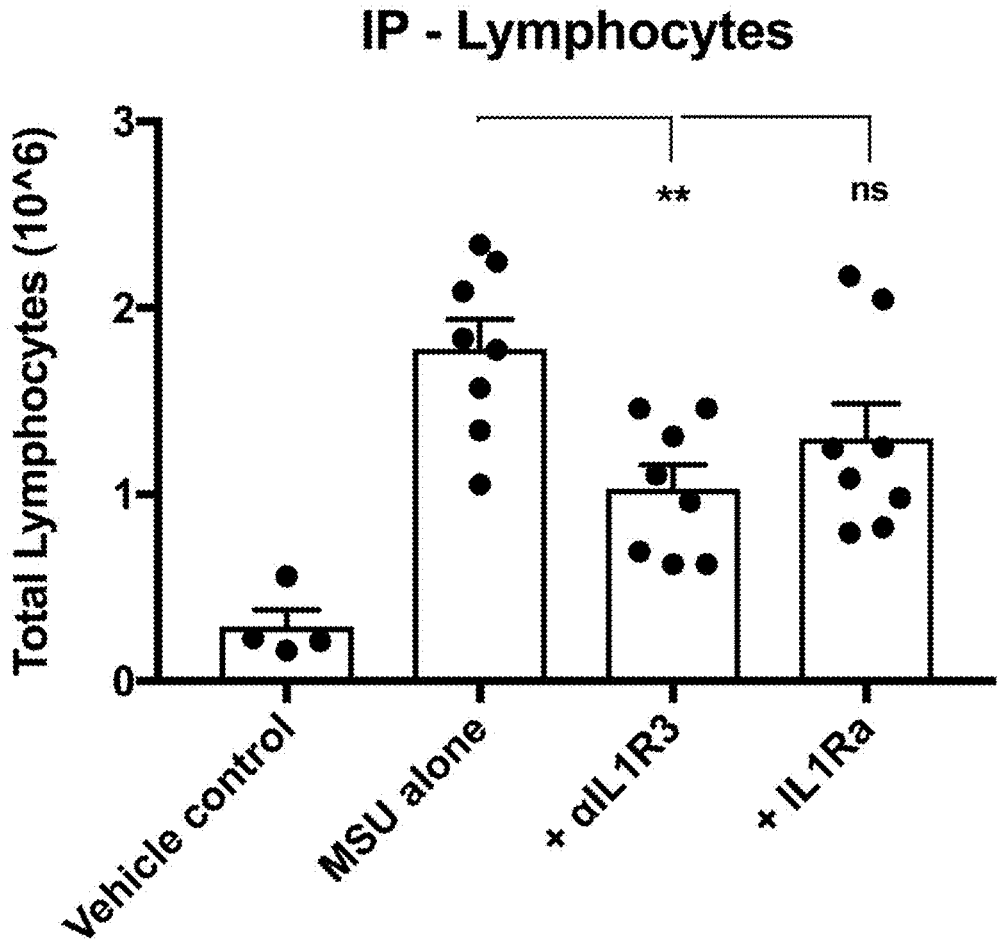
Figure 19:
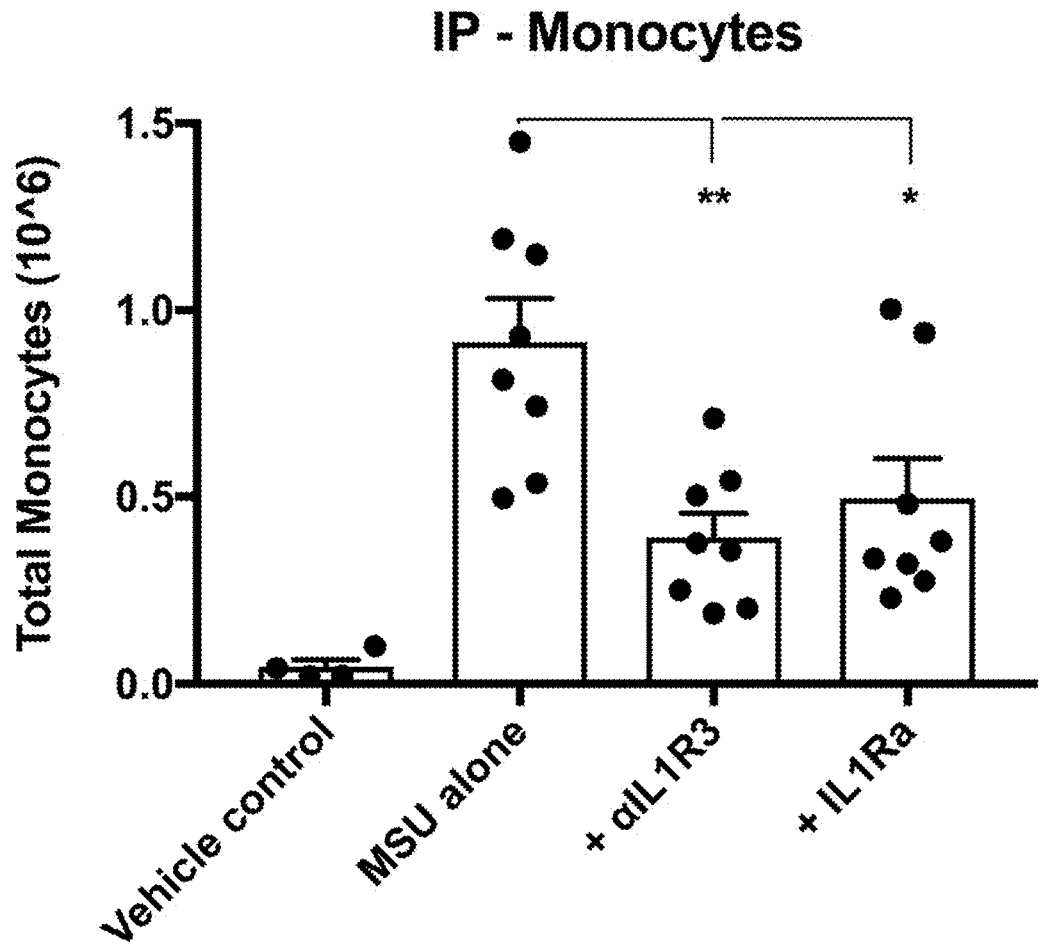
Figure 19:
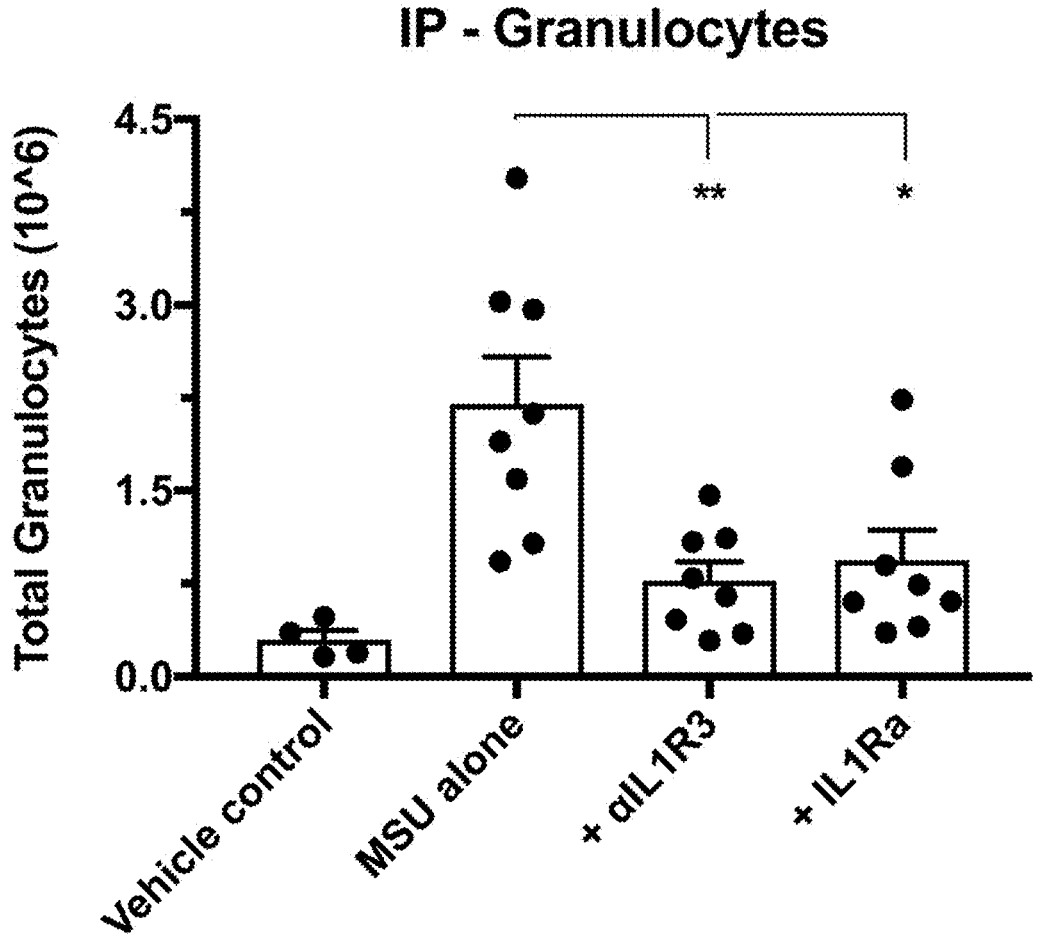
Figure 19:
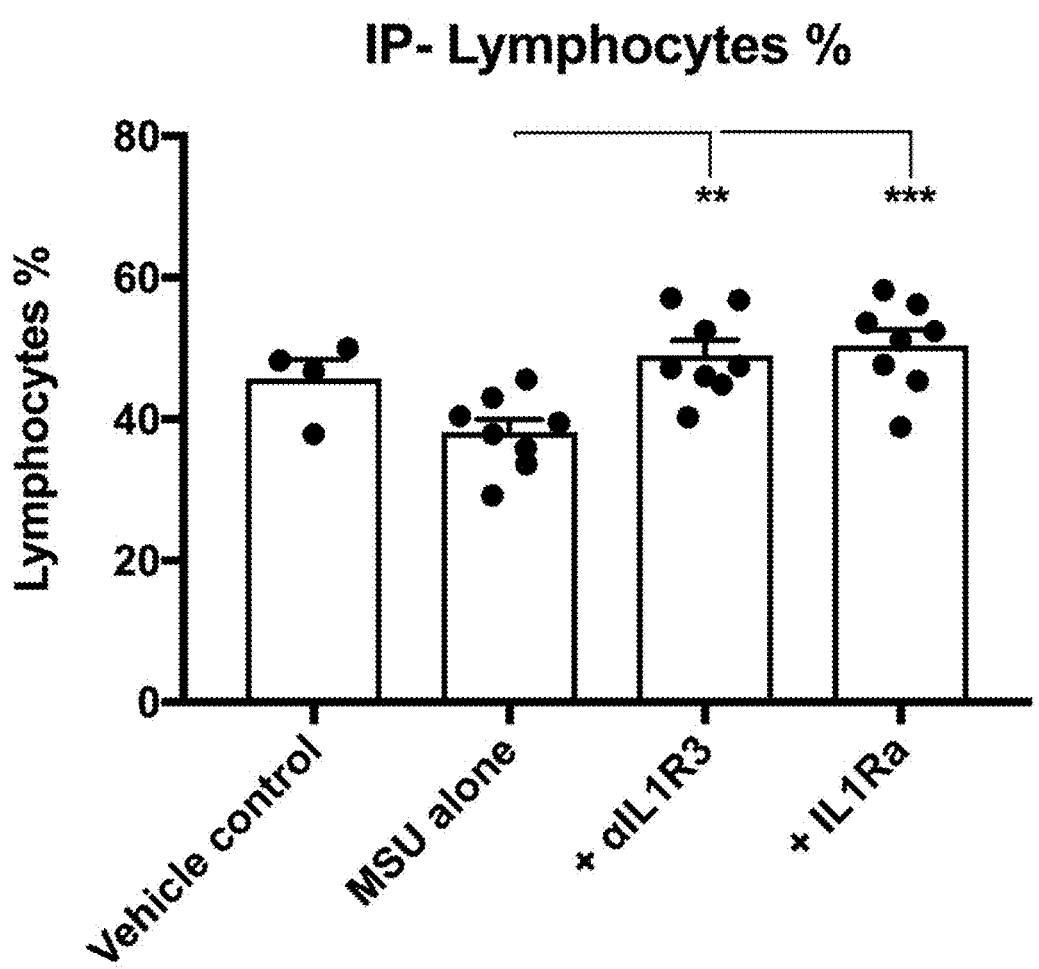
Figure 19:
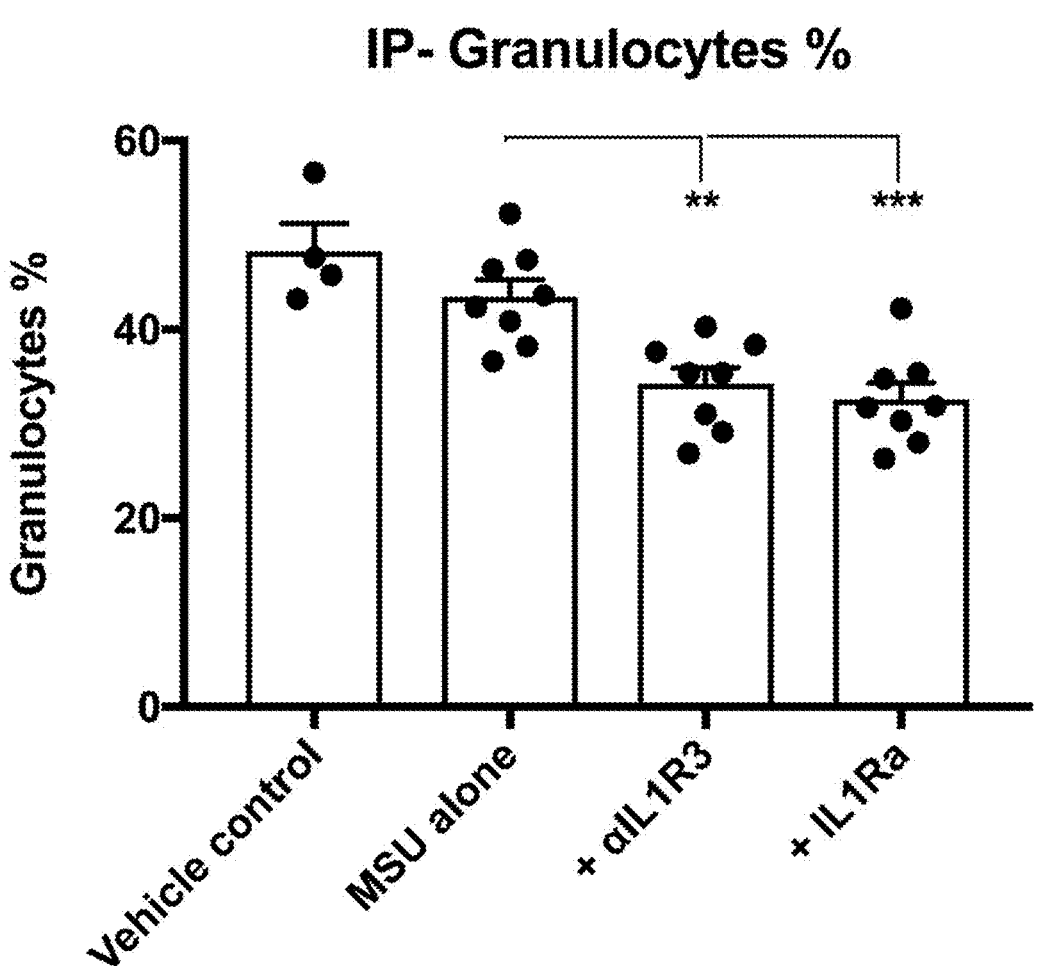
Figure 19:
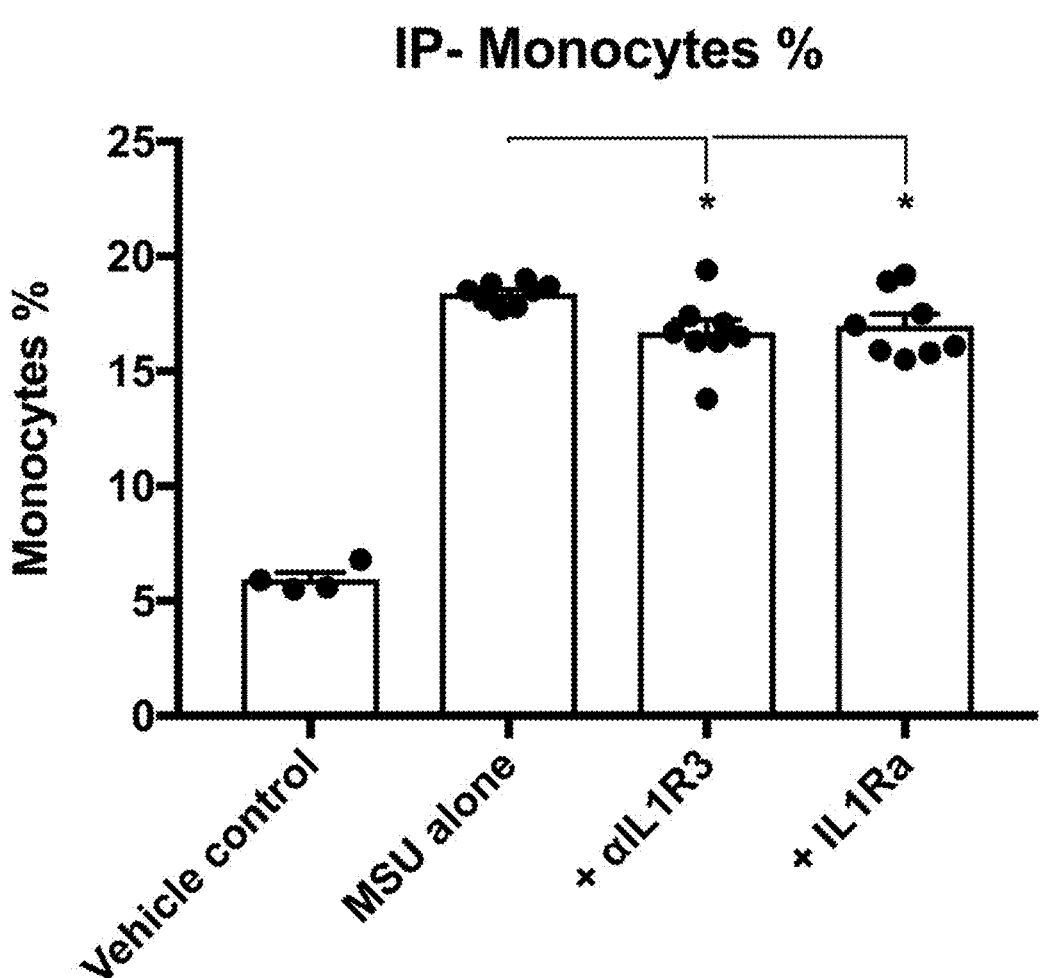

Fig. 19: Monosodium urate crystal (MSU)-induced mouse peritonitis model
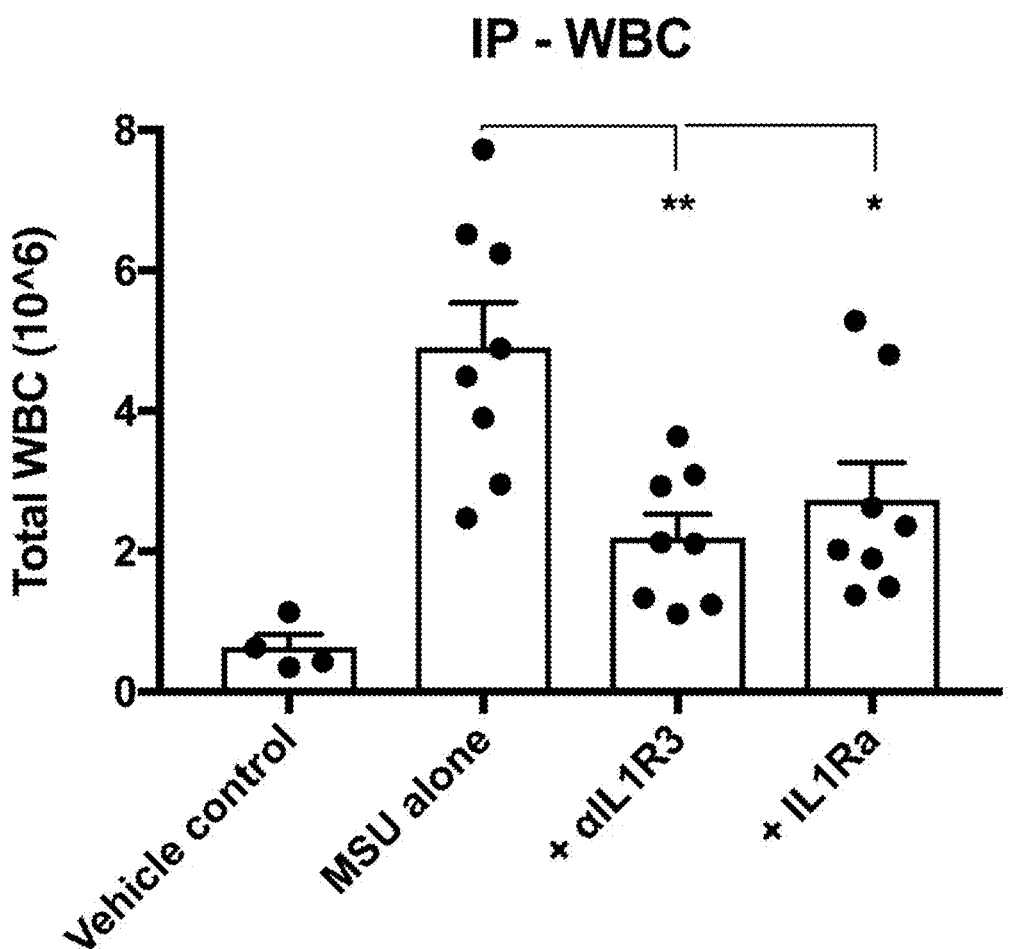

Fig. 20: Neutrophil activation and cytokine production in MSU peritonitis

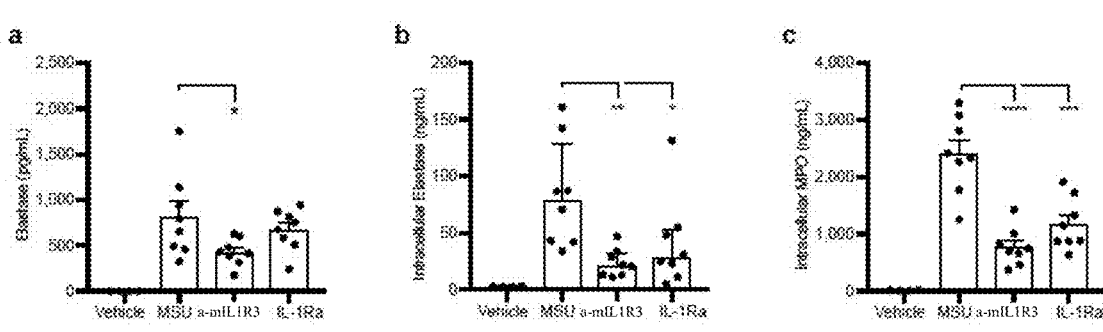

| IP fluid | Vehicle (n=4) | MSU-stimulated (n=8) | a-mIL1R3 (n=8) | IL-1Ra (n=8) |
|---|---|---|---|---|
| IL-6 (pg/mL) | Below detection | 65.0 ±14.9 | 19.8 ±5.8 (p=0.814) | 36.9 ±14.4 (p=0.164) |
| G-CSF (pg/mL) | 5.0 (2.8-5.5) | 77.7 (53.6-97.3) | 6.6 (4.9-33.0) (p=0.015) | 8.6 (7.5-17.8) (p=0.005) |
| KC (pg/mL) | 2.3 ±0.5 | 82.7 ±15.9 | 38.4 ±11.6 (p=0.841) | 84.3 ±31.9 (p=0.965) |
| CCL-2 (pg/mL) | Below detection | 62.5 ±11.9 | 28.2 ±3.6 (p=0.011) | 74.2 ±14.5 (p=0.545) |
| CCL-3 (pg/mL) | 1.2 ±0.1 | 4.9 ±0.8 | 3.8 ±0.5 (p=0.161) | 5.7 ±0.9 (p=0.545) |
| Systemic | | | | |
| IL-6 (pg/mL), plasma | 5.0 ±3.4 | 89.8 ±19.4 | 22.7 ±5.7 (p=0.011) | 29.5 ±8.5 (p=0.078) |
| G-CSF (pg/mL), plasma | 294 ±28.4 | 6245 ±1055 | 3544 ±2743 (p=0.010) | 1157 ±639 (p=0.003) |
| KC (pg/mL), WB | 272 (243-719) | 2525 (2178-2730) | 1366 (811-1889) (p=0.065) | 2269 (1511-3213) (p=0.959) |
| MPO (ng norm.), spleen | 42.5 ±7.6 | 145 ±9.7 | 89.3 ±11.4 (p=0.002) | 106 ±9.7 (p=0.013) |
| KC (pg norm.), spleen | 16.2 (13.3-38.3) | 189 (161-205) | 72.5 (49.6-140) (p=0.010) | 157 (95.3-238) (p=0.645) |

Fig 21: OVA allergic asthma in vivo model
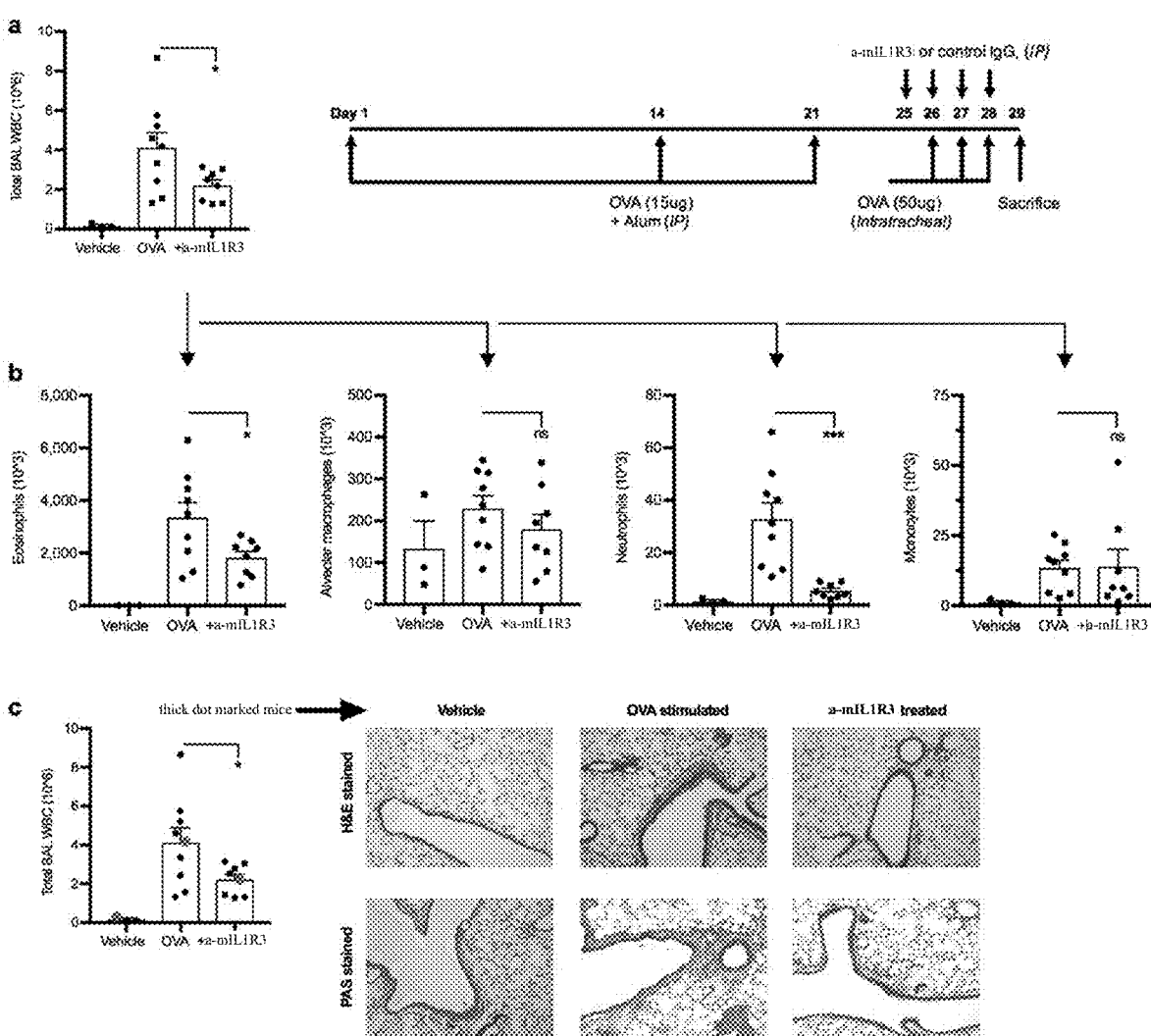

Fig. 22: Imiquimod psoriasis in vivo model
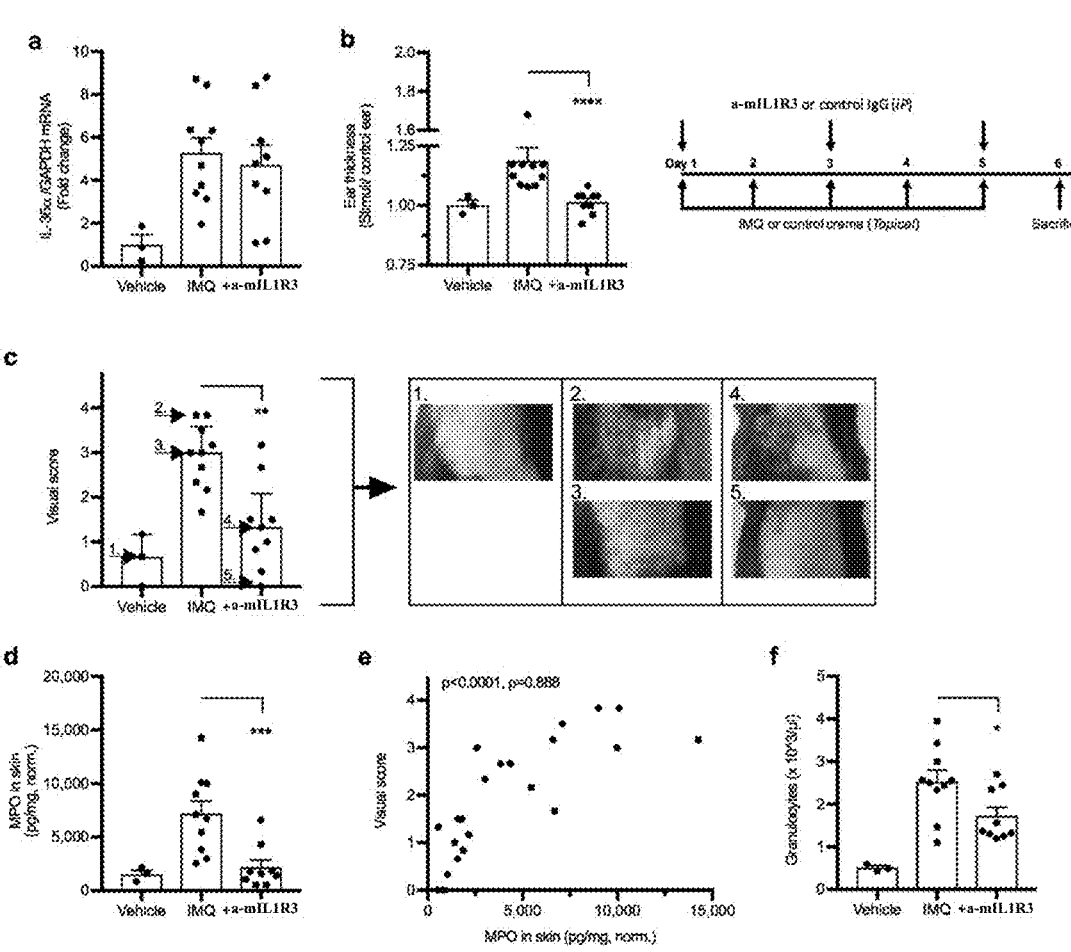

Fig. 23: Imiquimod psoriasis in vivo model
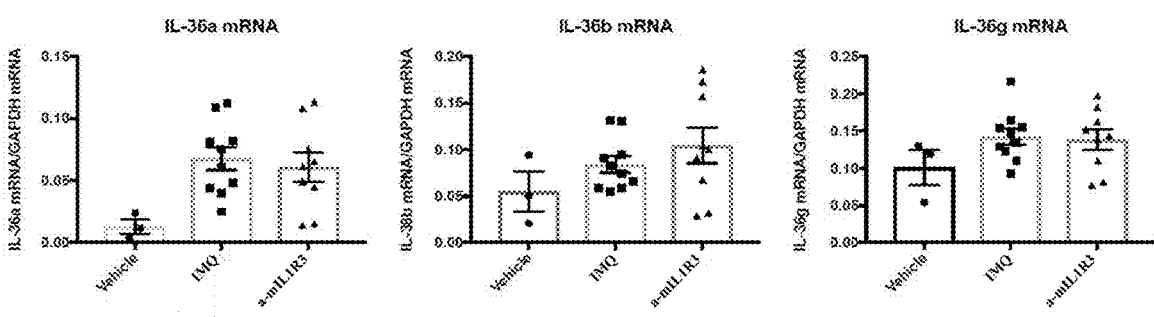
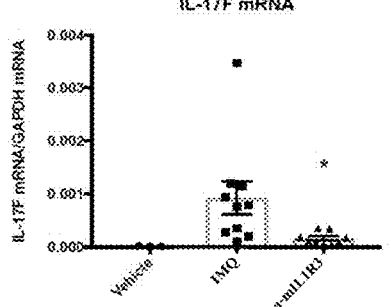
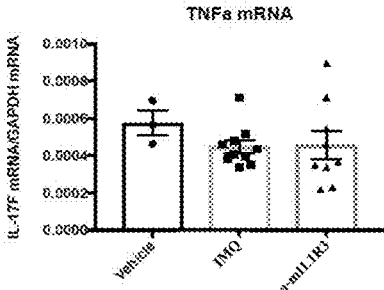

Fig. 24: Effector cell mediated function of anti-IL1R3 IgG1 and IgG1-LALA antibodies
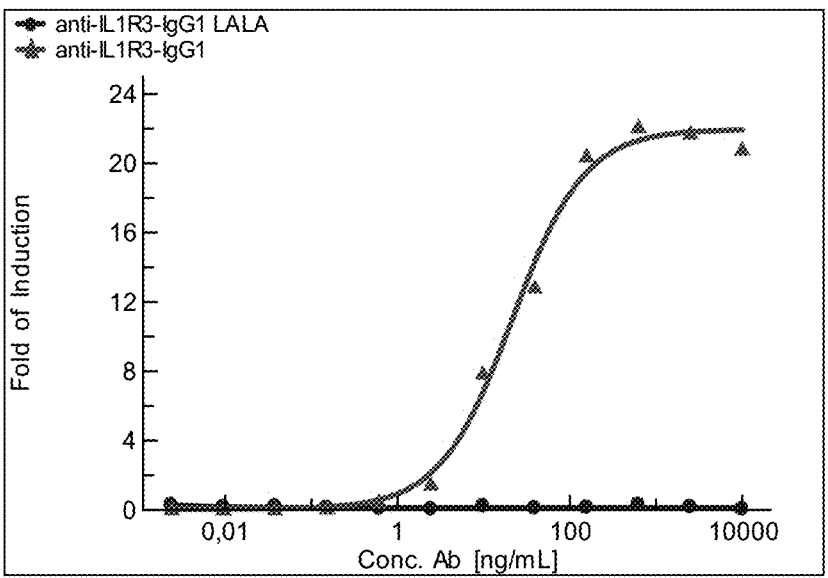

ANTI-IL-1R3 ANTIBODIES FOR USE IN INFLAMMATORY CONDITIONS

RELATED APPLICATIONS

This application is a continuation of U.S. patent application Ser. No. 16/612,052, which is a 35 U.S.C. § 371 filing of International Patent Application No. PCT/EP2018/061846, filed May 8, 2018, which claims priority to European Patent Application No. 17169953.1, the entire disclosures of which are hereby incorporated herein by reference.

SEQUENCE LISTING

The content of the electronically submitted Sequence Listing in XML file (Name: 740810_SA9-299USCON_ST26.xml; Size: 236,129 bytes; and Date of Creation: Mar. 15, 2023) is incorporated herein by reference in its entirety.

FIELD OF INVENTION

The invention pertains to methods for treating medical conditions and/or disorders characterized by uncontrolled or abnormal expression of members of the IL1R3 signaling pathway such as IL-1α, IL-1ß, IL-33, IL-36, IL1RA and/or IL1R3. More specifically, the present invention relates to methods and uses of anti-IL-1R3 antibodies in inflammatory conditions and/or disorders.

BACKGROUND

The interleukin 1 receptor accessory protein (IL1RAP), also called IL1R3, is a coreceptor of type 1 interleukin 1 receptor (IL1R1) and is indispensable for transmission of IL-1 signaling. Upon binding of IL-1, IL-1R1 associates with IL-1RAcP forming a functional signaling receptor complex, which stimulates NFkB activity.

IL-33, its receptor ST2, and IL-1RAcP form also a complex (IL-33/ST2/IL-1RAcP) with a similar activity in regard to NFkB activation as the IL-1β/IL-1R1/IL-1RAcP complex. IL-36 (IL-36α (IL-1F6), IL-36β (IL-1F8), and IL-36γ (IL-1F9)), their receptor IL-36R, and IL-1RAcP form also a complex (IL-36/Il-36R/IL-1RAcP) with a similar activity in regard to NFkB activation as the IL-1β/IL-1R1/IL-1RAcP complex.

The Interleukin-1 (IL-1) pathway is a cellular signaling pathway that plays a crucial role in the mammalian inflammatory response and is associated with a wide range of immunologic, metabolic, physiological and hematopoietic activities. The IL-1 family includes three structurally related cytokines: IL-1 alpha, IL-1 beta and IL-1 receptor antagonist (IL-1 ra). Of the three, IL-1 alpha and IL-1 beta are proinflammatory agonists while IL-1 receptor antagonist (IL-1ra) functions to block IL-1 alpha and IL-1 beta activity. All known biological functions of IL-1 are mediated through the type I IL-1 R. IL-1 alpha, IL-1 beta and IL-1 ra bind the type I IL-1 R with high affinity. In contrast, IL-1 beta binds the type II IL-1R with high affinity and IL-1 alpha and IL-Ira bind the type II IL-1 R with a low affinity. The type II IL-1 R has a severely truncated cytoplasmic domain and upon binding to IL-1 does not transduce signal to a cell, but instead is involved in regulating an IL-1-mediated response by acting as a decoy receptor.

IL-1 production is triggered by infections, microbial toxins, inflammatory agents and allergic reactions. Overall the main functions of IL-1 is to regulate the amplitude and duration of the immune and inflammatory response at the sites of inflammation or allergic immune reaction. When excess IL-1 is produced or IL-1 expression is not appropriately regulated disease states can develop. Accordingly, IL-1 has been implicated in a variety of inflammatory and immunoregulatory diseases and conditions. It has been proposed that a systemic or localized excess of IL-1 contributes to the incidence of numerous medical disorders. Further to this proposal, it has been shown that IL-1ra, which blocks IL-1 alpha and IL-1 beta activity, has varying degrees of efficacy in treating some diseases thought to be mediated by IL-1 signaling.

It has been suggested that the suppression of IL-1 might be beneficial in patients suffering from various disorders characterized by abnormal or excessive IL-1 expression or IL-1 activity. The IL-1ra and ICE inhibitors have met with limited degrees of success as therapeutics for diseases associated with IL-1 activity.

Although progress has been made in devising effective treatment for such diseases, improved medicaments and methods of treatment are needed.

Unfortunately, existing IL-1 pathway inhibitors such as Kineret, ilaris or Arcalyst have certain disadvantages which impede their therapeutic use. For example, Kineret (IL-1Ra) has a short half-life and therefore needs very frequent treatment intervals (daily). Antibodies targeting single cytokines (e.g. Ilaris) allow redundant signaling/activities of other IL-1 family cytokines to occur. In addition, IL-1 family cytokines are known to elicit both pro-inflammatory and IL-1R3-independent anti-inflammatory signaling, both of which are interfered with when targeting the cytokines or their alpha-chain receptors. In contrast, the antibodies of the present invention combine the advantages of infrequent treatment intervals, concomitant inhibition of different IL-1 family cytokine mediated signaling and specificity with regard to blocking pro-inflammatory signaling pathways.

Therefore, the present invention provides for novel and improved methods for treating conditions associated with an uncontrolled expression of members of the IL1R3 signaling pathway with the favorable features described in the following.

SUMMARY OF INVENTION

The present invention relates to methods for treating medical conditions and/or disorders characterized by uncontrolled or abnormal expression of members of the IL1R3 signaling pathway such as IL-1α, IL-1ß, IL-33, IL-36, IL1RA and/or IL1R3, as well as variants thereof.

More specifically, the present invention relates anti-IL1R3 antibodies for use in the treatment of an IL1R3-mediated inflammatory condition and/or disorder in a subject.

Such conditions and disorders include but are not limited to inflammatory diseases, immune disorders, fibrotic disorders, eosinophilic disorders, infection, pain, a central nervous system disorder, an ophthalmologic disorder, Hereditary Systemic Inflammatory Diseases, and Systemic and Local Inflammatory Diseases and cancer associated chronic inflammation.

Definitions

The term "rabbit" according to the invention means an animal of the members of the taxonomic order Lagomorpha, which includes the families (hares and rabbits) and Ocho-tonidae (pikas), preferably of genus *Oryctolagus*.

The term "antibody" encompasses the various forms of antibody structures including, but not being limited to, whole antibodies and antibody fragments as long as it shows the properties according to the invention.

The term "rabbit monoclonal antibody" according to the invention means a monoclonal antibody produced by immu-nizing a rabbit and isolated from a antigen producing cell of said rabbit as well as such an antibody which is further modified, preferably a humanized antibody, a chimeric anti-body, a fragment thereof, or a further genetically engineered and recombinant produced antibody as long as the charac-teristic properties according to the invention are retained. Preferably the antibody is from a B cell or a rabbit hybridoma cell of said rabbit.

The term "antibody producing cell" according to the invention means a rabbit B cell which produce antibodies, preferably a B cell or rabbit hybridoma cell.

"Native antibodies" are usually heterotetrameric glyco-proteins composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence iden-tity. Alignment for purposes of determining percent amino acid sequence identity can be achieved in various ways that are within the skill in the art, for instance, using publicly available computer software such as BLAST, BLAST-2, ALIGN or Megalign (DNASTAR) software.

The term "VL (or VH) region" has the same meaning as VL (or VH) domain.

The terms "Fc receptor" or "FcR" according to the invention refers to a human receptor that binds to the Fc region of an antibody. FcRs bind IgG antibodies and include receptors of the FcγRI, FcγRII, and FcγRIII subclasses, including allelic variants and alternatively spliced forms of these receptors. FcγRII receptors include FcγRIIA (an "acti-vating receptor") and FcγRIIB (an "inhibiting receptor"), which have similar amino acid sequences that differ primar-ily in the cytoplasmic domains thereof. Activating receptor FcγRIIA contains an immunoreceptor tyrosine-based acti-vation motif (ITAM) in its cytoplasmic domain. Inhibiting receptor FcγRIIB contains an immunoreceptor tyrosine-based inhibition motif (ITIM) in its cytoplasmic domain (see review M. in Daeron, Annu. Rev. Immunol. 15:203-234 (1997)). FcRIIIA (CD16a) mediates ADCC. FcRs are reviewed in Ravetch and Kinet, Annu. Rev. Immunol 9:457-92 (1991); Capel et al, Immunomethods 4:25-34 (1994); and de Haas et al, J. Lab. CHn. Med. 126:330-41 (1995). These and all other FcRs are encompassed by the term "FcR" herein. The term also includes the neonatal receptor, FcRn, which is responsible for the transfer of maternal IgGs to the fetus (Guyer et al, J. Immunol. 117:587 (1976) and Kim et al, J. Immunol. 24:249 (1994)) and mediates slower catabo-lism, thus longer half-life.

The term "antibody effector function(s)," or "effector function" as used herein refers to a function contributed by an Fc effector domain(s) of an IgG (e.g., the Fc region of an immunoglobulin). Such function can be effected by, for example, binding of an Fc effector domain(s) to an Fc receptor on an immune cell with phagocytic or lytic activity or by binding of an Fc effector domain(s) to components of the complement system. Typical effector functions are ADCC, ADCP and CDC.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear anti-bodies; single-chain antibody molecules (e.g. scFv); and multispecific antibodies formed from antibody fragments.

An "antibody that binds to the same epitope" as a refer-ence antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

"Antibody-dependent cell-mediated cytotoxicity" and "ADCC" refer to a cell-mediated reaction in which nonspe-cific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FCYRIII.

The term "Antibody-dependent cellular phagocytosis" and "ADCP" refer to a process by which antibody-coated cells are internalized, either in whole or in part, by phago-cytic immune cells (e.g., macrophages, neutrophils and dendritic cells) that bind to an immunoglobulin Fc region.

C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commer-cially from, e.g. Quidel, San Diego, Calif.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$.

The heavy chain constant domains that correspond to the different classes of immunoglobulins are called α, δ, ε, γ, and μ, respectively.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat, et al., Sequences of Proteins of Immunological Interest, 5th Ed. Public Health Service, National Institutes of Health, Bethesda, MD (1991).

A "variant Fc region" comprises an amino acid sequence which differs from that of a "native" or "wildtype" sequence Fc region by virtue of at least one "amino acid modification" as herein defined. The term "Fc-variant" as used herein refers to a polypeptide comprising a modification in an Fc domain. The Fc variants of the present invention are defined according to the amino acid modifications that compose them. Thus, for example, P329G is an Fc variant with the substitution of proline with glycine at position 329 relative to the parent Fc polypeptide, wherein the numbering is according to the EU index. The identity of the wildtype amino acid may be unspecified, in which case the aforementioned variant is referred to as P329G. For all positions discussed in the present invention, numbering is according to the EU index. The EU index or EU index as in Kabat or EU numbering scheme refers to the numbering of the EU antibody (Edelman, et al., Proc Natl Acad Sci USA 63 (1969) 78-85, hereby entirely incorporated by reference.) The modification can be an addition, deletion, or substitution. Substitutions can include naturally occurring amino acids and non-naturally occurring amino acids. Variants may comprise non-natural amino acids. Examples include U.S. Pat. No. 6,586,207; WO 98/48032; WO 03/073238; US 2004/0214988 AI; WO 05/35727 A2; WO 05/74524 A2; Chin, J. W., et al., Journal of the American Chemical Society 124 (2002) 9026-9027; Chin, J. W., and Schultz, P. G., ChemBioChem 11 (2002) 1135-1137; Chin, J. W., et al., PICAS United States of America 99 (2002) 11020-11024; and, Wang, L., and Schultz, P. G., Chem. (2002) 1-10, all entirely incorporated by reference.

The term "Fc region-containing polypeptide" refers to a polypeptide, such as an antibody or immunoadhesin (see definitions below), which comprises an Fc region.

The terms "Fc receptor" or "FcR" are used to describe a receptor that binds to the Fc region of an antibody. A FcR which binds an IgG antibody (a gamma receptor) includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see review in Daeron, M., Annu. Rev. Immunol. 15 (1997) 203-234). FcRs are reviewed in Ravetch, and Kinet, Annu. Rev. Immunol 9 (1991) 457-492; Capel, et al., Immunomethods 4 (1994) 25-34; and de Haas, et al., J. Lab. Clin. Med. 126 (1995) 330-41. Other FcRs, including those to be identified in the future, are encompassed by the term "FcR" herein. The term also includes the neonatal receptor, FcRn, which is responsible for the transfer of maternal IgGs to the fetus (Guyer, et al., J. Immunol. 117 (1976) 587 and Kim, et al., J. Immunol. 24 (1994) 249).

By "IgG Fc ligand" as used herein is meant a molecule, preferably a polypeptide, from any organism that binds to the Fc region of an IgG antibody to form an Fc/Fc ligand complex. Fc ligands include but are not limited to FcγRs, FcγRs, FcγRs, FcRn, Clq, C3, mannan binding lectin, mannose receptor, staphylococcal protein A, streptococcal

6 protein G, and viral FcγR. Fc ligands also include Fc receptor homologs (FcRH), which are a family of Fc receptors that are homologous to the FcγRs (Davis, et al., Immunological Reviews 190 (2002) 123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans, this family includes but is not limited to FcγRI (CD64), including isoforms FcγRIA, FcγRIB, and FcγRIC; FcγRII (CD32), including isoforms FcγRIIA (including allotypes H131 and R131), FcγRIIB (including FcγRIIB-I and FcγRIIB-2), and FcγRIIc; and FcγRIII (CD 16), including isoforms FcγRIIIA (including allotypes VI 58 and F158) and FcγRIIIb (including allotypes FcγRIIB-NAI and FcγRIIB-NA2) (Jefferis, et al., Immunol Lett 82 (2002) 57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD 16), and FCYRIII-2 (CD 16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

An "immunoconjugate" means an antibody conjugated to one or more cytotoxic agents, such as a chemotherapeutic agent, a drug, a growth inhibitory agent, a toxin, another antibody or a radioactive isotope.

"Antibody fragments" comprise a portion of a full-length antibody, preferably the variable regions thereof, or at least the antigen binding site thereof. Examples of antibody fragments include diabodies, Fab fragments, and single-chain antibody molecules. scFv antibodies are, e.g., described in Huston, J. S., Methods in Enzymol. 203 (1991) 46-88.

The terms "monoclonal antibody" or "monoclonal antibody composition" as used herein refer to a preparation of antibody molecules of a single amino acid composition.

The term "humanized antibody" or "humanized version of an antibody" also refers to antibodies for which both heavy and light chains are humanized as a result of antibody engineering. A humanized chain is typically a chain in which the V-region amino acid sequence has been changed so that, analyzed as a whole, is closer in homology to a human germline sequence than to the germline sequence of the species of origin. Humanization assessment is based on the resulting amino acid sequence and not on the methodology per se.

The terms "specifically binding, against target, or anti-target antibody", as used herein, refer to binding of the antibody to the respective antigen (target), measured by ELISA, wherein said ELISA preferably comprises coating the respective antigen to a solid support, adding said antibody under conditions to allow the formation of an immune complex with the respective antigen or protein, detecting said immune complex by measuring the Optical Density values (OD) using a secondary antibody binding to an antibody according to the invention and using a peroxidase-mediated color development.

The term "antigen" according to the invention refers to the antigen used for immunization or a protein comprising said antigen as part of its protein sequence. For example, for immunization a fragment of the extracellular domain of a protein (e.g. the first 20 amino acids) can be used and for detection/assay and the like the extracellular domain of the protein or the full-length protein can be used.

The term "specifically binding" or "specifically recognized" herein means that an antibody exhibits appreciable affinity for an antigen and, preferably, does not exhibit significant cross-reactivity. "Appreciable" binding affinity includes binding with an affinity of at least $10^{-7}$M, specifically at least $10^{-8}$M, more specifically at least $10^{-9}$M, or even more specifically at least $10^{-10}$M.

An antibody that "does not exhibit significant cross-reactivity" is one that will not appreciably bind to an undesirable other protein. An antibody specific for an epitope according to the invention will, for example, not significantly cross-react with other epitopes on IL-1R3. Specific binding can be determined according to any art-recognized means for determining such binding, e.g. by competitive binding assays (e.g. ELISA).

All protein terms as used herein refers to the human proteins. If a protein from another species is meant, this is explicitly mentioned.

The term "IL-1alpha"", as used herein, refers to human IL-1 (UniProtKB P01583). The term "IL-1beta"", as used herein, refer to human IL-1beta (UniProtKB P01584). IL-1 stimulates thymocyte proliferation by inducing IL-2 release, B-cell maturation and proliferation, and fibroblast growth factor activity. IL-1 proteins are involved in the inflammatory response, being identified as endogenous pyrogens (UniProtKB).

The term "IL-33"", as used herein, refers to human IL-33 (UniProtKB 095760), a cytokine that binds to and signals through the IL1RL1/ST2 receptor which in turn activates NF-kappa-B and MAPK signaling pathways in target cells (UniProtKB).

The term "IL-36"", as used herein, refers to human IL-36alpha (UniProtKB Q9UHA7, IL-36beta (UniProtKB Q9NZH7) and or IL-36gamma (UniProtKB Q9NZH8). IL-36 are cytokines that bind to and signal through the IL1RL2/IL-36R receptor which in turn activates NF-kappa-B and MAPK signaling pathways in target cells linked to a pro-inflammatory response. IL-36 seems to be involved in skin inflammatory response by acting on keratinocytes, dendritic cells and indirectly on T cells to drive tissue infiltration, cell maturation and cell proliferation (UniProtKB).

The term "NFkB" as used herein, refer to human nuclear factor NF-kappa-B, which consists of p105 subunit (P19838) and p100 subunit (Q00653).

"Inhibition of NFkB" is measured according to the invention as inhibition of NFkB dependent luciferase gene expression in human cells. Such methods are e.g. described in Windheim M. et al., Mol. Cell. Biol. 28 (2008) 1783-1791; Huang J. et al. PNAS USA 94 (1997) 12829-12832; Xiaoxia L. et al., Mol. Cell, Biol. 19 (1999) 4643-4652. If murine NFkB is meant herein it is explicitly mentioned.

The "variable region (or domain) of an antibody according to the invention" (variable region of a light chain (VL), variable region of a heavy chain (VH)) as used herein denotes each of the pair of light and heavy chain regions which are involved directly in binding the antibody to the antigen. The variable light and heavy chain regions have the same general structure and each region comprises four framework (FR) regions whose sequences are widely conserved, connected by three complementary determining regions, CDRs. The antibody according to the invention comprises a VH region and a VL region or parts thereof, which are both together sufficient for the specific binding to the respective antigen.

The term "antigen-binding portion of an antibody" when used herein refer to the amino acid residues of an antibody which are responsible for antigen-binding. The antigen-binding portion of an antibody comprises preferably amino acid residues from the "complementary determining regions" or "CDRs". The CDR sequences are defined, and their residues are numbered, according to Kabat et al, Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable region. The Kabat numbering of residues may be determined for a given antibody by alignment at regions of homology of the sequence of the antibody with a "standard" Kabat numbered sequence.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term "cancer" as used herein may be, for example, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers.

DETAILED DESCRIPTION OF THE INVENTION

As outlined in the introduction of this application, there are several difficulties in providing for suitable methods to treat inflammatory conditions that are mediated through an uncontrolled expression of members of the IL1R3 pathway. The present invention is meeting this need and provides for methods of treating, inhibiting, or ameliorating inflammatory conditions and/or disorders, including an immune disorder, a fibrotic disorder, an eosinophilic disorder, an infection, pain, a central nervous system disorder, an ophthalmologic disorder, Hereditary Systemic Inflammatory Diseases, and Systemic and Local Inflammatory Diseases.

The present invention relates to a method of treating, inhibiting or ameliorating an inflammatory condition and/or disorder in a subject in need thereof, the method comprising administering to the subject a therapeutically effective amount of an antagonistic IL1R3 antibody.

In particular, the invention encompasses anti-IL1R3 antibody for use in the treatment of an IL1R3-mediated inflammatory condition and/or disorder in a subject.

Such inflammatory condition and/or disorder may be selected from the group consisting of an inflammatory condition, an immune disorder, a fibrotic disorder, an eosinophilic disorder, an infection, pain, a central nervous system disorder, an ophthalmologic disorder, Hereditary Systemic Inflammatory Diseases, and Systemic and Local Inflammatory Diseases.

In one aspect of the invention, the inflammatory disorder treated is an IL-1 dependent diseases. The disease can be a Systemic and Local Inflammatory Diseases such as Schnitzler Syndrome, Behçet Disease, secondary amyloidosis, Henoch-Schonlein purpura, Idiopathic recurrent pericarditis, Systemic-onset Juvenile Idiopathic Arthritis, Adult Onset Still Disease, Macrophage Activation Syndrome, Sweet's Syndrome/neutrophilic dermatoses, neutrophilic panniculitis, Erdheim-Chester/histiocytoses, SAPHO, PFAPA, Multicentric Castleman Disease, Jessner-Kanof Disease, Primary Sjoegren Syndrome Fatigue, Kawasaki Disease, Colitis in Chronic Granulomatous Disease, Hidradenitis Suppurativa, Autoimmune Inner Ear Disease, Severe Traumatic Brain Injury), or a Hereditary Systemic Inflammatory Diseases such as Familial Mediterranean fever (FMF), CAPS, TRAPSa, HIDS, PAPA, PASH, DIRA, Blau syndrome/granulomatous arthritis, mevalonate kinase deficiency, Majeed Syndrome, NLRP12 Autoinflammatory Syndrome.

In preferred aspects of the invention, the inflammatory condition is selected from the group of COPD, inflammatory skin diseases, psoriasis, generalized pustular psoriasis (GPP), Inflammatory bowel disease (IBD), asthma, atopic dermatitis, Idiopathic pulmonary fibrosis, peritonitis, rheumatoid arthritis (RA), or a metabolic rheumatic disorder associated with hyperuricemia.

In one preferred embodiment, the inflammatory condition is a metabolic rheumatic disorder associated with hyperuricemia. The metabolic rheumatic disorder can be selected from the group of gout, pseudogout, drug-induced gout and chronic active (refractory) gout.

For the treatment of said metabolic rheumatic disorders in accordance with one aspect of the invention, an IL1R3 antagonistic antibody is administered. Said IL1R3 antagonistic antibody can be administered in combination with a therapeutic agent for the treatment of gout.

It can be administered simultaneously with a therapeutic agent for the treatment of gout. But it can also be administered sequentially with a therapeutic agent for the treatment of gout.

Another aspect of the invention encompasses methods for treatment of an inflammatory condition and/or disorder, wherein the inflammatory condition is a cancer associated chronic inflammation.

The invention also relates to anti-IL1R3 antibodies for the treatment of an inflammatory condition and/or disorder, wherein the inflammatory condition is a cancer associated chronic inflammation.

The term "cancer" as used herein may be, for example, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers.

Preferably, the antibody according to the invention is used for the treatment of a cancer associated chronic inflammation wherein the cancer is selected from the group consisting of pancreatic cancer, liver cancer, lung cancer (associated with inflammation caused by asbestos, infections, smoking, silica), non-small-cell-lung cancer, colorectal cancer/colitis-associated cancer (associated with Inflammatory bowel disease), stomach cancer, gastric cancer, chronic gastritis associated gastric cancer, estrogen-receptor-positive breast cancer, head and neck squamous cell carcinoma, Mesothelioma, Gall bladder cancer (chronic cholecystitis associated), ovarian cancer, bladder cancer, prostate cancer, E. coli-infection associated prostate cancer, Thyroid cancer, Hodgkin disease, MALT lymphoma, salivary gland cancer, melanoma, endometriosis associated endometrial carcinoma, Barrett's esophagitis associated Esophageal cancer.

Preferably, the cancer is breast cancer, colon cancer, lung cancer, pancreatic cancer, liver cancer, non-small-cell-lung cancer, colorectal cancer, stomach cancer, gastric cancer, estrogen-receptor-positive breast cancer, head and neck squamous cell carcinoma, Mesothelioma, Gall bladder cancer, ovarian cancer, bladder cancer, prostate cancer, Thyroid cancer, Hodgkin disease, MALT lymphoma, salivary gland cancer, or melanoma.

The antibodies of the invention can be used for treating a cancer associated chronic inflammation as some tumors are caused or promoted by tumor micro-environment cells secreting inflammatory cytokines such as IL-1α, IL-1ß, IL-33, IL-36. In some instances, expression of such cytokines results in the formation of tumor resistance.

Therefore, in one aspect of the invention, the antibody is used for the treatment of subjects, wherein the subjects comprise a tumor, such as a solid tumor, and show tumor resistance or insufficient response to cytotoxic, cytostatic or targeted/immunotherapy. Preferably, the subjects are human subjects, e.g. cancer patients.

A concomitant or sequential use of cytokine inhibitors and anti-cancer compounds significantly improves the response rate of such treatments or can break tumor resistance.

The present invention therefore also encompasses a method for the treatment of a subject, wherein the subject is characterized in being resistant or showing insufficient response to treatment with one or more cytotoxic, cytostatic or targeted anti-cancer agents.

In one aspect of this invention, said IL1R3 antibody is administered in combination with one or more cytotoxic, cytostatic or targeted anti-cancer agents.

In one aspect of the invention, said IL1R3 antagonistic antibody is administered simultaneously with one or more cytotoxic, cytostatic or targeted anti-cancer agents. In another aspect, the IL1R3 antagonistic antibody is administered sequentially with one or more cytotoxic, cytostatic or targeted anti-cancer agents.

In the latter case, it is preferred that the antibody is administered after treatment with one or more cytotoxic, cytostatic or targeted anti-cancer agents.

The cytotoxic or cytostatic anti-cancer agents according to the invention can be taxanes, anthracyclins, alkylating agents, Histone Deacetylase Inhibitors, Topoisomerase inhibitors, kinase inhibitors, nucleotide analogs, peptide antibiotics, and platinum-based agents.

Preferably the targeted anti-cancer agents are used in targeted therapy and selected from one of the following, or combinations thereof: anti-EGFR compounds such as cetuximab, gefitinib, erlotinib, lapatinib, panitumumab, and anti-HER2 compounds such as trastuzumab, ado-trastuzumab emtansine, pertuzumab.

It is further preferred that the targeted anti-cancer agents are targeted checkpoint inhibitors. These can be but are not limited to: anti-PD1 compounds such as pembrolizumab, and nivolumab, and anti-PDL1 compounds such as atezolizumab, Avelumab, and Durvalumab, and anti-CTLA-4 compounds such as Ipilimumab and Tremelimumab.

The present invention provides for a significantly improved response rate to targeted cancer therapy as a broad spectrum of the inhibition of cytokine induced signaling is achieved. Such an activity in cancer indications is not achieved through a direct depletion activity of cancer cells (as done by several compounds of prior art) but through the inhibition of the cancer associated inflammation by modulating IL1R3 signaling pathways.

The antibodies of the present invention provide for a very advantageous activity profile because they enable the effective inhibition of cancer associated chronic inflammation and, at the same time, avoid undesired side effects, because they do not affect the viability of targeted cells that express IL-1R3.

The present invention therefore provides for several advantages over other IL-1 family targeting therapies. The commercially compound Kineret (IL-1Ra) has a short half-life and very frequent treatment intervals (daily). Antibodies targeting single cytokines (e.g. Ilaris) allow redundant signaling/activities of other IL-1 family cytokines to occur. In addition, IL-1 family cytokines are known to elicit both pro-inflammatory and IL-1R3-independent anti-inflammatory signaling, both of which are interfered with when targeting the cytokines or their alpha-chain receptors. In contrast, the antibodies of the present invention combine the advantages of infrequent treatment intervals, concomitant inhibition of different IL-1 family cytokine mediated signaling and specificity with regard to blocking pro-inflammatory signaling pathways.

The antibodies as described herein are preferably monoclonal antibodies with high affinity, high specificity, and potent neutralizing activity against IL-1R3. The present invention therefore also encompasses IL-1R3 antibody, with high affinity and specificity for IL-1R 3, with potent IL-1R3 neutralizing activity, and improved stability.

In one preferred embodiment of the invention, the antibodies have reduced effector functions. Preferably, the antibodies according to the invention show reduced or no Fcγ-receptor signaling. Further preferred, the antibody does not induce ADCC.

It is another aspect of the invention that the anti-IL1R3 antibodies according comprises at least amino acid substitutions L234A and L235A of the human IgG1 Fc region or S228P and L235E of the human $IgG_4$ Fc region or a corresponding functional mutation in another organism.

In one embodiment of the invention, the anti-IL1R3 antibody comprises a) a heavy chain variable region (VH) comprising the complementary determining regions comprising CDR-H1, CDR-H2, and CDR-H3
    wherein the CDR-H1 region comprises an amino acid sequence selected from the group of SEQ ID NO: 69-85, and 178
    wherein the CDR-H2 region comprises an amino acid sequence selected from the group of SEQ ID NO: 86-102, and 179
    and wherein the CDR-H3 region comprises an amino acid sequence selected from the group of SEQ ID NO: 103-119 and 180; and b) a light chain variable region (VL) comprising the complementary determining regions comprising CDR-L1, CDR-L2, and CDR-L3
    wherein the CDR-L1 region comprises an amino acid sequence selected from the group of SEQ ID NO: 120-136 and 181,
    wherein the CDR-L2 region comprises an amino acid sequence selected from the group of SEQ ID NO: 137-153 and 182, and
    wherein the CDR-L3 region comprises an amino acid sequence selected from the group of SEQ ID NO: 154-170, and SEQ ID NO: 175 and 183.

In one embodiment, said antibody of the invention comprises a substitution at position 2 of CDR-L3. Said substitution may be a cysteine to serine substitution.

In one aspect of the invention, the subject is a human subject and the antibody comprises a) a heavy chain variable region (VH) comprising the complementary determining regions comprising CDR-H1, CDR-H2, and CDR-H3
    wherein the CDR-H1 region comprises an amino acid sequence selected from the group of SEQ ID NO: 69-85,
    wherein the CDR-H2 region comprises an amino acid sequence selected from the group of SEQ ID NO: 86-102,
    and wherein the CDR-H3 region comprises an amino acid sequence selected from the group of SEQ ID NO: 103-119; and b) a light chain variable region (VL) comprising the complementary determining regions comprising CDR-L1, CDR-L2, and CDR-L3 wherein the CDR-L1 region comprises an amino acid sequence selected from the group of SEQ ID NO: 120-136, wherein the CDR-L2 region comprises an amino acid sequence selected from the group of SEQ ID NO: 137-153, and wherein the CDR-L3 region comprises an amino acid sequence selected from the group of SEQ ID NO: 154-170, and SEQ ID NO: 175.

In another aspect of the invention, the subject is a mouse and the antibody comprises a) a heavy chain variable region (VH) comprising the complementary determining regions comprising CDR-H1, CDR-H2, and CDR-H3 wherein the CDR-H1 region comprises the amino acid sequence of SEQ ID NO: 178, wherein the CDR-H2 region comprises the amino acid sequence of SEQ ID NO: 179, and wherein the CDR-H3 region comprises the amino acid sequence of SEQ ID NO: 180; and b) a light chain variable region (VL) comprising the complementary determining regions comprising CDR-L1, CDR-L2, and CDR-L3 wherein the CDR-L1 region comprises the amino acid sequence of SEQ ID NO: 181, wherein the CDR-L2 region comprises the amino acid sequence of SEQ ID NO: 182, and wherein the CDR-L3 region comprises an amino acid sequence of SEQ ID NO: 183.

In other embodiments of the invention, the antibody comprises a heavy chain variable (VH) region that is at least 90% identical to a VH region selected from the group consisting of VH regions of SEQ ID NO: 1 to 34 and 173 and 176, and a light chain variable (VL) region that is at least 90% identical to a VL region selected from the group consisting of VL regions of SEQ ID NO: 35 to 68 and 174 and 177.

In one embodiment to the invention, the antibody is a humanized antibody.

In such embodiments, the subject is a human subject and the antibody comprises a heavy chain variable (VH) region that is at least 90% identical to a VH region selected from the group consisting of VH regions of SEQ ID NO: 1 to 34 and 173, and a light chain variable (VL) region that is at least 90% identical to a VL region selected from the group consisting of VL regions of SEQ ID NO: 35 to 68 and 174.

In another embodiment, the subject is a mouse and the antibody comprises a heavy chain variable (VH) region that is at least 90% identical to the VH region of SEQ ID NO: 176, and a light chain variable (VL) region that is at least 90% identical to the VL region of SEQ ID NO: 177.

The antibodies according to the invention are in one embodiment, antibodies that bind specifically to IL-1R3 or a fragment or derivative thereof that contains at least a portion of said antibody that is sufficient to confer IL-1R3 binding specificity, and may comprise a heavy chain variable (VH) region that is at least 60% identical, preferably at least 70% identical, more preferably at least 80% identical, more preferably at least 90% identical to a VH region selected from the group consisting of VH regions of SEQ ID NO: 1 to 34 and 173 and 176.

In one embodiment, said antibodies comprise a heavy chain variable region (VH) sequence having at least 90%, 91%, 92%, 93%, 94%, 95%, 96%, 97%, 98%, 99%, or 100% sequence identity to an amino acid sequence selected from the group of VH sequences according to the invention.

In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, whereby the antibody retains the ability to bind specifically according to the invention to the respective antigen.

The present invention also relates to an antibody that specifically binds to IL-1R3 or a fragment or derivative thereof and contains at least a portion of said antibody that is sufficient to confer IL-1R3 binding specificity, and comprises a light chain variable (VL) region that is least 60% identical, preferably at least 70% identical, more preferably at least 80% identical, more preferably at least 90% identical to a VL region selected from the group consisting of VL regions of SEQ ID NO: 35 to 68 and 174 and 177.

Said antibody may comprise a light chain variable region (VL) having at least 90%, 91%, 92%, 93%, 94%, 95%, 96%, 97%, 98%, 99%, or 100% sequence identity to the amino acid sequence of the VL sequences according to the invention.

In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, whereby the antibody retains the ability to bind specifically to the respective antigen.

In certain embodiments, a total of 1 to 10 amino acids have been substituted, inserted and/or deleted in said VL sequences. In certain embodiments, the substitutions, insertions, or deletions occur in regions outside the CDRs (i.e., in the FRs). The invention also comprises affinity matured antibodies which can be produced according to methods known in the art. Marks et al. Bio/Technology 10:779-783 (1992) describes affinity maturation by VH and VL domain shuffling. Random mutagenesis of CDR and/or framework residues is described by: Barbas et al., Proc Nat. Acad. Sci, USA 91: 3809-3813 (1994); Schier et al., Gene 169: 147-155 (1995); Yelton et al., J. Immunol. 1 55:1994-2004 (1995); Jackson et al., J. Immunol. 1 54(7):3310-9 (1995); and Hawkins et al., J. Mol. Biol. 226:889-896 (1992) and WO2010108127.

In certain embodiments, a total of 1 to 10 amino acids have been substituted, inserted and/or deleted in each of said VH or VL sequences. In one embodiment, the antibody of the invention comprises a substitution at position 90 of the VH or VL sequence. It is preferred that the amino acid at position 90 is substituted by a serine. This substitution is preferably at position 90 of the light chain variable region (VL). In a preferred embodiment, the cysteine at position 90 of SEQ ID. NO: 62 is substituted by a serine. However, the antibodies of this invention are not limited to an amino acid substitution at position 90 but may comprise any substitution, deletion or insertion that leads to a functional antibody possessing the properties of the antibodies of this invention. Therefore, the VL and VH sequences of the antibodies of this invention may also comprise further mutations at different positions.

In certain embodiments, substitutions, insertions, or deletions occur in regions outside the CDRs (i.e., in the FRs).

In other embodiments, the substitutions, insertions, or deletions occur in regions inside the CDRs. In one preferred embodiment, the antibody of the invention comprises a substitution at position 2 of CDR-L3. It is preferred that this substitution is cysteine to serine. In one embodiment, said substitution is in SEQ ID NO: 164.

The present invention also encompasses an antibody that specifically binds to IL-1R3 or a fragment or derivative thereof that contains at least a portion of said antibody that is sufficient to confer IL-1R3 binding specificity, wherein the antibody comprises a heavy chain variable region (VH) comprising an amino acid sequence selected from the group of SEQ ID NO: 1 to 34 and 173 and 176.

Preferably, the heavy chain variable region (VH) sequence is SEQ ID NO:1, alternatively SEQ ID NO:2, or SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29, SEQ ID NO:30, SEQ ID NO:31, SEQ ID NO:32, SEQ ID NO:33, or alternatively SEQ ID NO:34 or 173 and 176.

Furthermore, the invention relates to methods in which said antibody that specifically binds to IL-1R3 or a fragment or derivative thereof that contains at least a portion of said antibody that is sufficient to confer IL-1R3 binding specificity, comprises a light chain variable region (VL) comprising an amino acid sequence selected from the group of SEQ ID NO: 35 to 68 and 174 and 177.

Even more preferred, the light chain variable region (VL) sequence is SEQ ID NO:35, or SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, or alternatively SEQ ID NO:68 or 174 or 177.

A antibody according to the invention that specifically binds to IL-1R3 or a fragment or derivative thereof that contains at least a portion of said antibody that is sufficient to confer IL-1R3 binding specificity, also comprises a VH region and a VL region comprising the respective CDR1, CDR2 and CDR3 regions of an antibody selected from the group consisting of MAB-15-0139, MAB-15-0106MAB-15-0108, MAB-15-0110, MAB-15-0117, MAB-15-0121, MAB-15-0140, MAB-15-0115, MAB-15-0125, MAB-15-0119, MAB-15-0109, MAB-15-0097, MAB-15-0135, MAB-15-0133, MAB-15-0107, MAB-15-0128, MAB-15-0116, MAB-16-0004, MAB-16-0009, MAB-16-0028, MAB-16-0031, MAB-16-0043, MAB-16-0049, MAB-16-0045, MAB-16-0040, MAB-16-0036, MAB-16-0046, MAB-16-0030, MAB-16-0021, MAB-16-0019, MAB-16-0015, MAB-16-0027, MAB-16-0048, MAB-16-0041, MAB-16-0149, MAB-16-0150, MAB-16-0531.

In one embodiment, the antibody that specifically binds to IL-1R3 or a fragment or derivative thereof that contains at least a portion of said antibody that is sufficient to confer IL-1R3 binding specificity, comprises SEQ ID NO.: 1 and 35, or SEQ ID NO.: 2 and 36. An antibody according to the invention may also comprise SEQ ID NO.: 3 and 37, or SEQ ID NO.: 4 and 38, or SEQ ID NO.: 5 and 39., or SEQ ID NO.: 6 and 40., or SEQ ID NO.: 7 and 41, or SEQ ID NO.: 8 and 42, or SEQ ID NO.: 9 and 43, or SEQ ID NO.: 10 and 44, or SEQ ID NO.: 11 and 45, or SEQ ID NO.: 12 and 46. Alternatively, an antibody according to the invention comprises SEQ ID NO.: 13 and 47, or SEQ ID NO.: 14 and 48, or SEQ ID NO.: 15 and 49, or SEQ ID NO.: 16 and 50, or SEQ ID NO.: 17 and 51, or SEQ ID NO.: 18 and 52, or SEQ ID NO.: 19 and 53, or SEQ ID NO.: 20 and 54, or SEQ ID NO.: 21 and 55, or SEQ ID NO.: 22 and 56, or SEQ ID NO.: 23 and 57, or SEQ ID NO.: 24 and 58, or SEQ ID NO.: 25 and 59, or SEQ ID NO.: 26 and 60, or SEQ ID NO.: 27 and 61.

Alternatively, an antibody according to the invention comprises SEQ ID NO.: 28 and 62, or SEQ ID NO.: 29 and 63, or SEQ ID NO.: 30 and 64, or SEQ ID NO.: 31 and 65, or SEQ ID NO.: 32 and 66, or SEQ ID NO.: 33 and 67, or SEQ ID NO.: 34 and 68, or SEQ ID NO.: 173 and 54, or SEQ ID NO.: 28 and 174, or SEQ ID NO.: 176 and 177.

Most preferably, the antibody that specifically binds to IL-1R3 or a fragment or derivative thereof that contains at least a portion of said antibody that is sufficient to confer IL-1R3 binding specificity comprises the constant region sequences CR-H (SEQ ID NO. 172) and CR-L (SEQ ID NO. 171) and a VH region selected from the group of SEQ ID NO: 1 to 34 and 173 and 176 and a VL region selected from the group of SEQ ID NO: 35 to 68 and 174 and 177.

The antibody that specifically binds to IL-1R3 or a fragment or derivative thereof that contains at least a portion of said antibody that is sufficient to confer IL-1R3 binding specificity, also comprises the constant region sequences CR-H (SEQ ID NO. 172) and CR-L (SEQ ID NO. 171) and a VH region and a VL region comprising the respective CDR1, CDR2 and CDR3 regions of an antibody selected from the group consisting of MAB-15-0139, MAB-15-0106, MAB-15-0108, MAB-15-0110, MAB-15-0117, MAB-15-0121, MAB-15-0140, MAB-15-0115, MAB-15-0125, MAB-15-0119, MAB-15-0109, MAB-15-0097, MAB-15-0135, MAB-15-0133, MAB-15-0107, MAB-15-0128, MAB-15-0116, MAB-16-0004, MAB-16-0009, MAB-16-0028, MAB-16-0031, MAB-16-0043, MAB-16-0049, MAB-16-0045, MAB-16-0040, MAB-16-0036, MAB-16-0046, MAB-16-0030, MAB-16-0021, MAB-16-0019, MAB-16-0015, MAB-16-0027, MAB-16-0048, MAB-16-0041, MAB-16-0149 and MAB-16-150, and MAB-16-0531.

According to the preferred therapeutic application of the antibodies according to the invention, the effector functions (such as ADCC) of the antibodies of the invention are reduced or lacking. In contrast to other antibodies of prior art, such as CAN04 (e.g. WO 2015/132602 A1), the antibodies of the invention avoid unwanted depletion of immune cells.

Preferably, the antibodies according to the invention show reduced or no Fcγ-receptor signaling.

Therefore, the invention also relates to an antibody, wherein said antibody comprises at least amino acid substitutions at L234A and L235A of the human IgG1 Fc region or S228P and L235E of the human IgG4 Fc region, or a functional equivalent mutation.

In one embodiment according to the invention, the antibody is a humanized IgG1$_{LALA}$ antibody. In another embodiment, the antibody is a mouse-IgG2a$_{LALA}$ antibody.

In one embodiment according to the invention, the antibody inhibits IL-1R3 induced NFkB activity.

In another embodiment, the antibody that specifically binds to IL-1R3 or a fragment or derivative thereof that contains at least a portion of said antibody that is sufficient to confer IL-1R3 binding specificity, binds to the same epitope as an antibody selected from the group of antibodies MAB-15-0139, MAB-15-0106, MAB-15-0108, MAB-15-0110, MAB-15-0117, MAB-15-0121, MAB-15-0140, MAB-15-0115, MAB-15-0125, MAB-15-0119, MAB-15-0109, MAB-15-0097, MAB-15-0135, MAB-15-0133, MAB-15-0107, MAB-15-0128, MAB-15-0116, MAB-16-0004, MAB-16-0009, MAB-16-0028, MAB-16-0031, MAB-16-0043, MAB-16-0049, MAB-16-0045, MAB-16-0040, MAB-16-0036, MAB-16-0046, MAB-16-0030, MAB-16-0021, MAB-16-0019, MAB-16-0015, MAB-16-0027, MAB-16-0048, MAB-16-0041, MAB-16-0149, MAB-16-150 and MAB-16-0531.

The antibodies according to the invention have the advantage to be very potent when it comes to binding to their target. They exhibit a strong binding capacity to their antigen, IL1R3, but not to other receptors. The binding properties of the antibodies were studied in biochemical enzyme-linked immunosorbent assays (ELISA) and cell binding analysis (flow cytometry) and are exemplified in FIGS. 2, 6 and 7.

Preferred antibodies according to the invention, show a half maximal effective concentration (EC50) of less than 30 ng/ml, preferably of less than 20 ng/ml. In other embodiments, they show an EC50 of less than 15 ng/ml, 10 ng/ml or of less than 5 ng/ml. A preferred antibody according to the invention shows an EC50 of 16.3 ng/ml in a biochemical ELISA experiment (cf. FIG. 7).

The antibodies according to the invention also show a very strong binding to their antigen in experiments in which human IL1R3 is expressed in different cell lines while the antibodies do not bind cell lines not expressing human IL1R3 (e.g. NIH-3T3, cf. FIG. 5).

In the IL1R3 high-expressing cell line SK-MEL-30 (cf. FIG. 6, Example 4) the antibodies exhibit an EC50 of preferably less than 400 ng/ml, more preferably less than 350 ng/ml, or less than 310 ng/ml.

In one preferred embodiment encompassed by the invention, the antibody according to the invention inhibits IL-1alpha and/or IL-1beta stimulated NFkB activity. FIGS. 3, 4 and 8 exemplify the strong inhibitory activity of the antibodies according to the invention.

In one embodiment, the antibody that specifically binds to IL-1R3 or a fragment or derivative thereof that contains at least a portion of said antibody that is sufficient to confer IL-1R3 binding specificity, inhibits IL-1alpha stimulated NFkB activity.

In another embodiment, the antibody that specifically binds to IL-1R3 or a fragment or derivative thereof that contains at least a portion of said antibody that is sufficient to confer IL-1R3 binding specificity inhibits IL-1beta stimulated NFkB activity.

It is preferred that an antibody according to the invention inhibits IL-1beta stimulated NFkB activity in HEK293T/17-FR cells with an EC50 of less than 100 ng/ml, preferably of less than 95 ng/ml, 85 ng/ml, 75 ng/ml, 65 ng/ml, 55 ng/ml, 45 ng/ml, 35 ng/ml, 25 ng/ml, 20 ng/ml and most preferred of less than 15 ng/ml (e.g. cf. FIG. 3).

It is further preferred that an antibody according to the invention inhibits IL-1alpha stimulated NFkB activity with an EC50 of less than 1000 ng/ml, preferably of less than 500 ng/ml, 300 ng/ml, 200 ng/ml, and most preferred of less than 100 ng/ml (e.g. cf. FIG. 8) in A549-NFkB-RE-Luc cells.

It is further preferred that an antibody according to the invention inhibits IL-1beta stimulated NFkB activity with an EC50 of less than 700 ng/ml, preferably of less than 600 ng/ml, 300 ng/ml, 200 ng/ml, 100 ng/ml and most preferred of less than 50 ng/ml in A549-NFkB-RE-Luc cells (e.g. cf. FIG. 8).

The invention also encompasses a antibody, wherein said antibody inhibits NFkB activity stimulated by a complex selected from the group consisting of IL-1β/IL-1R1/IL- 1RAcP, IL-1α/IL-1R1/IL-1RAcP IL-33/ST2/IL-1RAcP, and/or IL-36/Il-36R/IL-1RAcP.

Moreover, an antibody according to invention inhibits in a concentration of 10 µg/ml (rabbit IgG isotype has a molecular weight of 150 KD) NFkB expression in A549-NFkB-RE-Luc cell lysates (Steady-Glo™ Luciferase Assay System; Promega; Cat. No. E2510) stimulated with 0.1 ng/ml human IL-1alpha, human IL-1beta, IL-33 and/or IL-36 (molecular weight see UniProtKB/Swiss-Prot), for 50% or more, preferably for 70% or more, preferably for 80% or more preferably for 90% and more, and more preferably for 95% or more, related to the same assay without said antibody according to the invention.

In one embodiment, the antibody according to the invention inhibits IL-1alpha, IL-1beta, IL-33, and/or IL-36, respectively, stimulated luciferase activity in HEK 293T/17 cells (HEK 293T/17-FR cells transfected with luciferase under control of NF-kB reporter gene)), HEK-Blue-IL33™ cells (Invivogen) or HEK-293/17-IF cells.

Preferably, said IL-1alpha, stimulated luciferase activity is inhibited by 50% or more, preferably by 70% or more, preferably by 80% or more, preferably by 90% and more, and more preferably by 95% or more. Preferably, said IL-1alpha, stimulated luciferase activity is inhibited by 95%.

Preferably, said IL-1beta, stimulated luciferase activity is inhibited by 50% or more, preferably by 70% or more, preferably by 80% or more, preferably by 90% and more, and more preferably by 95% or more. Preferably, said IL-1beta, stimulated luciferase activity is inhibited by 95%.

Preferably, said IL-33, stimulated luciferase activity is inhibited by 50% or more, preferably by 70% or more, preferably by 80% or more, preferably by 90% and more, and more preferably by 95% or more. Preferably, said IL-33, stimulated luciferase activity is inhibited by 95%.

Preferably, said IL-36, stimulated luciferase activity is inhibited by 50% or more, preferably by 70% or more, preferably by 80% or more, preferably by 90% and more, and more preferably by 95% or more. Preferably, said IL-36, stimulated luciferase activity is inhibited by 95%.

Furthermore, the antibodies according to the invention inhibit human IL-1a and IL-1b mediated IL-6 release and are superior to polyclonal antibodies. This potent inhibitory activity is shown and exemplified in FIG. 9. In these experiments, the EC50 values demonstrate that humanized anti-IL-1R3 IgG1-LALA antibodies are superior to that of goat-anti-human-IL1-R3 polyclonal antibody AF676 (R&D Systems). In preferred embodiments of the invention, the antibodies inhibit human IL-a mediated IL-6 release with an EC50 of less than 2500 ng/ml, preferably of less than 1500 ng/ml, less than 1000 ng/ml, less than 600 ng/ml, less than 400 ng/ml, or less than 300 ng/ml. It is also preferred that the antibodies of the invention inhibit human IL-b mediated IL-6 release with an EC50 of less than 500 ng/ml, preferably of less than 400 ng/ml, less than 300 ng/ml, less than 200 ng/ml, or less than 150 ng/ml.

In another embodiment according to the invention, the antibodies inhibit human IL-33 mediated NfkB-signaling. FIG. 10 exemplifies the inhibitory activity of selected antibodies according to the invention in HEK-Blue-IL33™ cells and demonstrates the superiority over polyclonal antibodies. In preferred embodiments of the invention, the antibodies inhibit human IL-33 mediated NfkB-signaling with an EC50 of less than 20000 ng/ml, preferably of less than 18000 ng/ml, less than 3000 ng/ml, less than 1000 ng/ml, less than 500 ng/ml, or less than 400 ng/ml.

The antibodies of the invention may also inhibit human IL-36 mediated NfkB-signaling (FIG. 11). Preferably, they inhibit human IL-36 mediated NfkB-signaling at an EC50 of less than 100 ng/ml, preferably at less than 50 ng/ml, less than 40 ng/ml, less than 30 ng/ml, less than 20 ng/ml, or less than 15 ng/ml.

Strikingly, the inventors found that the antibodies according to the invention inhibit cytokine release mediated by various different stimuli. For example, the antibodies inhibit cytokine release mediated by IL-1a, IL-33 and IL-36a. Results of a selected antibody are shown in FIG. 12. For example, the antibody MAB-16-0030 inhibits cytokine release mediated by all three stimuli, while IL-1Ra affects only IL-1a mediated cytokine release.

Diseases associated with acute or chronic inflammation are maintained or establish by the action of multiple cytokines either at the same time or consecutively. Early "alarmins" such as IL-1a and IL-33 may trigger other cytokines including IL-1b and IL-36 to establish a strong inflammatory environment. Therefore, the concomitant inhibition of signaling mediated by multiple cytokines exerts efficacious control of inflammatory processes. It is a key aspect of the antibodies of the invention that they inhibit multi-cytokine signaling via the blockage of the IL1R3 receptor.

Binding of antibodies to immune cells may result in cell depleting and deleterious effects, e.g. by direct induction of apoptotic signaling pathways, stimulation of excessive cytokine release or antibody-dependent cellular cytotoxicity (ADCC).

Importantly, the antibodies according to the invention do not affect the viability of immune cells. For example, they do not affect the viability of human peripheral blood mononuclear cells (PBMCs) and they do not induce IL-6 release in PBMCs (cf. FIG. 13).

The antibodies according to the invention, do not only inhibit the functional activation of cytokine release in different cell lines as described above, but also in PMBCs or whole blood cells from donors. They inhibit cytokine release mediated by different specific or complex stimuli. For example, they inhibit activation of PBMCs stimulated with LPS, heat-inactivated *Candida albicans*, IL-12/IL-33 or anti-CD3/CD28 antibodies (cf. FIGS. 14 and 15).

Also, in one embodiment, the anti-IL-1R3 IgG1-LALA antibodies according to the invention are able to inhibit release of IFNg, IL-6, TNF-a, IL-13, IL-17 and IL-10 in mixed lymphocyte reactions (cf. FIG. 16).

The method of the present invention also encompasses the administering to a patient a pharmaceutically effective amount of the antibody, or derivative or fragment thereof according to the invention in form of a pharmaceutical composition.

Such a pharmaceutically composition may comprise a pharmaceutically acceptable carrier and a therapeutically effective amount of the antibody that specifically binds to the IL-1R3 or a fragment or derivative thereof that contains at least a portion of said antibody that is sufficient to confer IL-1R3 binding specificity, according to the invention.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

In another aspect, the present invention relates to an antibody that specifically binds to the mouse-IL-1R3 receptor or a fragment or derivative thereof, wherein the antibody comprises a heavy chain variable (VH) region that is at least 90% identical to a VH region of SEQ ID NO: 176, and a light chain variable (VL) region that is at least 90% identical to a VL region of SEQ ID NO: 177.

Preferably, said antibody comprises a heavy chain variable region (VH) sequence having at least 90%, 91%, 92%, 93%, 94%, 95%, 96%, 97%, 98%, 99%, or 100% sequence identity to an amino acid sequence selected from the group of VH sequences according to the invention.

In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, whereby the antibody retains the ability to bind specifically according to the invention to the respective antigen.

In another aspect of the invention, said antibody comprises a light chain variable region (VL) sequence having at least 90%, 91%, 92%, 93%, 94%, 95%, 96%, 97%, 98%, 99%, or 100% sequence identity to an amino acid sequence selected from the group of VL sequences according to the invention.

In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, whereby the antibody retains the ability to bind specifically according to the invention to the respective antigen.

It is preferred that said antibody that specifically binds to the mouse-IL-1R3 receptor or a fragment or derivative thereof, has reduced or is lacking its effector functions.

Preferably, the antibodies according to the invention show reduced or no Fcγ-receptor signaling. It is further preferred that they do not induce ADCC.

In one embodiment, the antibody of the invention that specifically binds to the mouse-IL-1R3 receptor or a fragment or derivative thereof, is mouse IgG2a with mutations L234A and L235A in its FC part (amino acid positions according to EU numbering index).

Another aspect of the invention relates to an antibody that specifically binds to the mouse-IL-1R3 receptor or a fragment or derivative thereof, for use in pre-clinical studies. Such studies can be carried out in animal models, preferably in murine disease models. Such model systems include but are not limited to monosodium urate crystal (MSU)-induced mouse peritonitis model, Serum transfer induced rheumatoid arthritis, collagen-induced arthritis, antibody-induced arthritis, collagen antibody-induced arthritis, K/B×N antibody transfer arthritis, imiquimod-induced inflammatory skin disease/psoriasis, Epidermolysis bullosa acquisita model, Thioglycollate induced peritonitis, Immunecomplex induced peritonitis, bleomycin induced lung fibrosis, xenotranplantation psoriasis, tobacco smoke-induced lung inflammation COPD, tracheal instillation of elastase COPD, Fluorescein isothiocyanate (FITC) induced lung injury/fibrosis, Radiation-Induced Fibrosis, Silica induced lung fibrosis, asbestos fibre induced lung fibrosis, DSS induced colitis, Trinitrobenzene Sulfonic Acid induced Colitis, Oxazolone induced Colitis, Adoptive Transfer Colitis, house dust mite (HDM), cockroach, or *Alternaria* alternate induced asthma, ovalbumin induced asthma, papain-induced lung inflammation, epicutaneous sensitization atopic dermatitis model (ovalbumin, House dust mite (HDM), Hapten, *S. aureus*), xenograft or patient-derived-xenograft tumor growth models using immunocompromised or humanized mice, grafting of syngeneic tumors, chemical induced skin tumor models, DSS-induced colorectal tumor models.

Preferably, the antibody is used in the monosodium urate crystal (MSU)-induced mouse peritonitis model.

EXAMPLES

The following examples are used in conjunction with the figures and tables to illustrate the invention.

Example 1: Human-IL-1R3 Biochemical ELISA

Assay Principle:

NUNC Maxisorp 384 well microtiter plates are coated with Fc-tagged human IL-1R3. After a blocking process, specific antibodies from B-cell supernatants bind to the antigen and are then detected by a POD-labeled antibody. Samples are tested 1:2 diluted.

Materials:

Plates: 384 well NUNC Maxisorp plates; Cat. No. 464718

Proteins: Fc-tagged human IL-1R3 (Conc. 1.5 mg/ml; Assay Conc. 0.5 μg/ml)

Standard Ab: P013-02 (Conc. 1 mg/ml; Start Assay Conc. 2 μg/ml)

Detection Ab: Anti-rabbit IgG, peroxidase-linked species-specific whole antibody (from donkey) (ECL); GE; Cat. No. NA9340; assay dilution: 1:5000

PBS: Buffers in a Box, Premixed PBS Buffer, 10×; Roche Applied Sciences; Cat. No. 11666789001

BSA: Bovine Serum Albumin Fraction V from bovine serum; Roche Applied Sciences; Cat. No. 10735086001

Tween 20: Tween 20; Carl Roth; Cat. No. 9127.2

TMB: TMB Solution; Life Technologies; Cat. No. SB02

HCl: 1M Titripur Hydrochloric Acid; Merck; Cat. No. 1090571000

ELISA Buffer: PBS, 0.5% BSA, 0.05% Tween

Wash Buffer: PBS, 0.1% Tween

Block Buffer: PBS, 2% BSA, 0.05% Tween

Procedure:

1. Add 12.5 μL Fc-tagged human IL-1R3 (0.5 μg/ml) in PBS to a 384 well NUNC Maxisorp plate and incubate for 1 h at RT.
2. Wash 3× with 90 μl Wash Buffer.
3. Add 90 μL Blocking buffer to each well and incubate for 1 h at RT.
4. Wash 3× with Wash Buffer.
5. Add 12.5 μL antibody in Elisa Buffer and incubate for 1 h at RT.
6. Wash 3× with Wash Buffer.
7. Add 12.5 μL 1:5000 POD-Antibody in Elisa Buffer and incubate for 1 h at RT.
8. Wash 6× with Wash Buffer.
9. Add 15 μL TMB.
10. Add 15 μL HCl after sufficient development.
11. Read absorbance at 450 nm/620 nm.

Example 2: Characterization of h-IL-1R3-Specific Antibodies Inhibiting hIL-1R3-Receptor by Luciferase Reporter Experiment Assay Principle:

293T/17-FR cells, which express a NF-kB-RE firefly luciferase reporter, are seeded into Poly-D-Lysin-Cell culture plates. After stimulation with IL-1b the 293T/17-FR lysate is tested for activated NF-kB using the Steady-Glo Luciferase Assay Kit. Supernatants with functional antibodies bind to hIL-1R3 and inhibit the NF-kB activation, which is shown in low signal.

Materials:

Plates: Cell plate: 384 well PDL Costar Cell Culture plate; Cat. No. 3844

Assay plate: 384 well lumitrac white-plate; Corning; Cat. No. 3572

Cells: 293T/17-FR; assay conc. 250.000 cells/ml

Proteins: IL-1b (Conc. 0.03 mg/ml; Assay Conc. 115 μg/ml; Working Conc. 230 pg/ml)

Standard Ab: P013_06 (Conc. 0.2 mg/ml; Start Working Conc. 6 µg/ml)

Kit: Steady-Glo Luciferase Assay System; Promega; Cat. No. E2510

Cell-Medium: DMEM Medium; PAN Biotech; Cat. No. P04-04510

FCS: Fetal Bovine Serum, HyClone; Thermo; Cat. No. St30070.03

293T/17-FR Medium: DMEM Medium, 10% FCS, (+20 µg/ml Hygromycin-B)

Procedure:

1. Cell Culture Procedure:

Split confluent 293T/17-FR cells every Monday (seed out: 5×106 cells/T175 flask) and Friday (seed out: 3×106 cells/T175 flask) using trypsin/EDTA (incubate just for 30 sec at RT).

2. Seed cells (0.25×106 cells/ml) in 25 µl DMEM+10% FCS to a 384-well PDL-plate (Corning cat #3844) and incubate over night at 37° C. and 5% CO2.

3. Aspirate media and add 12.5 µl antibodies in Conditioned Medium or just Conditioned Medium and incubate for 30 min at 37° C. and 5% CO2 (program: 3 Aspiration and Sample transfer)

4. Add 12.5 µl IL-1b in DMEM+10% FCS and incubate for 5 hours at 37° C. and 5% CO2.

5. Equilibrate cultured cells to RT for 10 min.

6. Add 25 µl Steady-Glo Reagent and mix several times with pipette

7. Wait 5 minutes before transfer 45 µl supernatant to a 384-well lumitrac white plate (Corning Cat #3572)

8. Measure luminescence in Tecan Reader: Integration Time: 0.5 sec

Example 3: Inhibition of NFKB-Expression of A549-NFKB-RE-Luc Stable Transfected Cells after Stimulation with IL-1 (α/β)

Assay Principle:

A549-NFκB-RE-Luc stable transfected cells (Signosis) are pipetted to a 384-well plate and incubated overnight. On day 2 anti-IL1R3 antibodies are allowed to bind to A549-NFkB-RE-Luc stable transfected cells, which are then stimulated by addition of IL-1 (α or β). This results in transcription of the luciferase gene due to NFKB signaling pathway activation and can be measured by cell lysis and addition of luciferin.

It is tested whether antibodies can inhibit the activation of NFkB pathway and therefore lower the luminescence signal.

Materials:

Plates: 384-well Low Flange White Flat Bottom Polystyrene TC-Treated Microplates Sterile; Corning; Cat. No. 3570

Proteins: IL-1 α (P026_09); Recombinant Human IL-1alpha/IL-1F1; 10 µg/mL; R&D Systems; Cat. No. 200-LA-002

IL-1 β (P026_10); Recombinant Human IL-1beta/IL-1F2; 25 µg/mL; R&D Systems; Cat. No. 200-LB-005

Standard Ab: MAB-15-0115; MAB Discovery GmbH; 2.51 mg/ml; working conc. 10 µg/ml Cells: A549-NFKB-RE-Luc stable transfected cells; Signosis; Cat. No. SL-0014

Medium: DMEM; PAN; Cat. No. P04-04510

FCS: Fetal Bovine Serum South Africa Low IgG; PAN; Cat. No. 1552-P120909

Pen/Strep: 10,000 U Penicillin/ml; 10 mg Streptomycin/ml; PAN Biotech; Cat. No. P06-07100

Detaching Agent: Trypsin-EDTA 1×; PAN; Cat. No. P10-023100 (4 mL for T175/2 mL for T75; ~8 min 37° C.)

Cell-Medium: DMEM, 10% FCS, 1% Pen/Strep

Detection Kit: Steady-Glo™ Luciferase Assay System; Promega; Cat. No. E2510

Procedure:

1. Cultivate A549-NFKB-RE-Luc stable transfected cells (1.7E+04 cells/cm$^2$ for 3 days; 2.28E+04 cells/cm$^2$ for 2 days) in Cell-Medium. Do not go beyond 10 passages!

2. Plate out 40,000 A549-NFKB-RE-Luc stable transfected cells in 25 µL medium per well (conc.=1.6×10$^6$ cells/mL) to a white cell-culture treated 384 well plate with flat bottom.

Incubate over night at 37° C./5% CO$_2$.

3. Aspirate medium from plate and add 10 µL sample or standard in medium to plate using CyBio pipetting roboter (Program: "Medium removal and sample transfer" in folder P026/NFκB). Incubate for 1 h at 37° C./5% CO$_2$.

4. Add 10 µL IL-1 (α or β) in medium to plate using CyBio pipetting roboter (Program: "Transfer from reservoir" in folder P026/NFκB) (working conc.: 0.2 ng/mL; assay conc.: 0.1 ng/mL) and incubate 5 h at 37° C./5% CO$_2$.

Before performing step 4, dissolve Steady-Glo substrate in Steady-Glo buffer according to Steady-Glo protocol and equilibrate this solution and the assay plate to RT.

5. Add 20 µL Steady-Glo mix, mix thoroughly to guarantee proper cell lysis. Incubate at RT, 10 min.

6. Determine the relative luminescence units of each well, using a microplate reader set to 500 ms integration time (program: Lumineszenz-384).

Example 4: Cell Binding Analysis

A549 and NIH-3T3 cells were cultured in DMEM+10% FCS. HEK-293 cells were cultured in DMEM+15% FCS and SK-MEL-30 in RPMI+10% FBS. Cells were harvested using Accumax (Sigma), washed with PBS and resuspended in stain buffer (BD Pharmingen). Anti-IL-1R3 antibodies were incubated with the cells in stain buffer for 30 minutes at 4° C. at a concentration of 10 µg/ml. For EC50 SK-MEL-30 cell binding analysis, cells were incubated in a 1:2 dilution series starting with 20 µg/ml. Cells were washed with stain buffer and incubated with Alexa-488 labelled goat-anti-human secondary antibody (Dianova) for 30 minutes at 4° C. Cells were washed with stain buffer and resuspended in buffer containing 1:100 diluted DRAQ7 (Abcam) dead cell stain. Cells were analysed using a BD Accuri C6 Sampler flow cytometer. Fitting curve and EC50 calculation was done using Excel (Microsoft) and XLfit (IDBS).

Example 5: Biochemical Human-IL-1R3 ELISA

Nunc 384-well Maxisorp plates were coated with recombinant Fc-tagged hIL-1R3 (Ser21-Glu359) at a concentration of 0.25 µg/ml in PBS for 60 minutes at room temperature. Plates were washed three times with wash buffer (PBS 0.1% Tween) and blocked with PBS, 0.2% BSA, 0.05% Tween for 60 minutes at room temperature. After three washes with wash buffer, antibodies were added in ELISA buffer (PBS, 0.5% BSA, 0.05% Tween) at concentrations ranging from 6 to 0.03 µg/ml (1:3 dilution series) and were incubated for 60 min at room temperature. Plates were washed three times with wash buffer, followed by incubation with anti-human-IgG peroxidase-linked, species specific F(ab)2 Fragment (goat, AbD Serotec) at a dilution of 1:5000 in ELISA Buffer for 60 minutes at room temperature. Plates were washed six times with wash buffer before TMB substrate solution (Invitrogen, 15 µl/well) was added. After 5 minutes of incubation, stop solution (1M HCl, 151l/well) was added and absorbance (450 nm/620 nm) measured using a Tecan M1000 plate reader. Fitting curves and EC50 calculation were done using Excel (Microsoft) and XLfit (IDBS).

Example 6: IL-1α and IL-1β Functional Neutralization Assay

A-549-NFκB-RE-Luc (Signosis) were cultivated in DMEM, 10% FCS, 1% Pen/Strep for 5 days before they were seeded out in 384-well white flat bottom polystyrene tissue-culture-treated microplates (Corning) at a cell density of 40,000 cells/well in 25 µl medium. Cells were incubated over night at 37° C./5% $CO_2$. Medium was removed by aspiration and monoclonal or polyclonal (goat-anti-human-IL-1R3, AF676, R&D Systems) antibodies added at various concentrations in a volume of 10 µl medium and incubated for 60 minutes at 37° C./5% $CO_2$. Recombinant human IL-1α or IL-1β (R&D Systems) proteins were added in 10 µl medium to a final concentration of 0.1 ng/ml and plates were incubated for 5 hours at 37° C./5% $CO_2$. 20 µl Steady-Glo™ (Promega) solution were added to each well, mixed thoroughly and plates were incubated for 10 minutes at room temperature before luminesce was measured using a Tecan M1000 plate reader. Fitting curves and EC50 calculation were done using Excel (Microsoft) and XLfit (IDBS).

Example 7: IL-1α and IL-1β Functional Neutralization Assay—A-549 IL6-Release Assay A549 cells were seeded out at a density of 6,000 cells/well in 25 µl medium in 384-well clear cell culture treated plates (Corning) in DMEM, 10% FCS, 1% Pen/Strep. Cells were incubated over night at 37° C./5% $CO_2$. Medium was removed by aspiration and monoclonal or polyclonal (goat-anti-human-IL-1R3, AF676, R&D Systems) antibodies were added at various concentrations in a volume of 12.5 µl medium and incubated for three hours at 37° C./5% $CO_2$. Recombinant human IL-1α or IL-1β (R&D Systems) proteins were added in 12.5 µl medium to a final concentration of 0.1 ng/ml and plates were incubated for 48 hours at 37° C./5% $CO_2$. Secreted human-IL-6 levels in the cell supernatant were measured using the DuoSet human IL-6 ELISA kit (R&D Systems, Cat. No. DY206-05) according to the manufacturer's instructions. Fitting curves and EC50 calculation were done using Excel (Microsoft) and XLfit (IDBS).

Example 8: IL-33 Functional Neutralization Assay

HEK-Blue™ IL-33 cells (InvivoGen) were cultivated in DMEM, 10% FCS for 5 days before they were seeded out in 384-well clear, flat bottom, cell culture treated microplates (Corning) at a cell density of 25,000 cells/well in 15 µl medium. Various concentrations of monoclonal or polyclonal (goat-anti-human-IL-1R3, AF676, R&D Systems) antibodies were added in a volume of 5 µl medium and plates were incubated for 60 minutes at 37° C./5% $CO_2$. Recombinant human IL-33 (R&D Systems) protein was added in 5 µl medium to a final concentration of 5 ng/ml and plates were incubated over night at 37° C./5% $CO_2$. 5 µl cell supernatants were transferred to clear, flat bottom polystyrene NBS™ microplates (Corning) containing 20 µl 2×QUANTI-Blue reagent (InvivoGen). Plates were incubated at 37° C. for 45 minutes and optical density measured at 655 nm using a Tecan M1000 plate reader. Fitting curves and EC50 calculation were done using Excel (Microsoft) and XLfit (IDBS).

Example 9: IL-36 Functional Neutralization Assay

HEK293/17-IF Cells (MAB Discovery GmbH) were cultivated in DMEM, 10% FCS, 20 µg/ml hygromycin for 5 days before they were seeded out in 384-well white, flat bottom, cell culture treated plates (Corning) at a cell density of 30,000 cells/well in 20 µl medium. Cells were incubated over night at 37° C./5% $CO_2$. Medium was removed by aspiration and various concentrations of monoclonal or polyclonal (goat-anti-human-IL-1R3, AF676, R&D Systems) antibodies were added in a volume of 10 µl medium. Plates were incubated for 60 minutes at 37° C./5% $CO_2$. Recombinant human IL-36g (R&D Systems) protein was added in 10 µl medium to a final concentration of 15 ng/ml and plates were incubated for 5 hours at 37° C./5% $CO_2$. 20 µl Steady-Glo™ (Promega) solution was added to each well, mixed thoroughly and plates were incubated for 10 minutes at room temperature before luminescence was read using a Tecan M1000 plate reader. Fitting curves and EC50 calculation were done using Excel (Microsoft) and XLfit (IDBS).

Example 10: Neutralization of IL-1α, IL-33 and IL-36α

The functions of anti-IL-1R3 antibodies were tested on three different cell lines with either IL-1α, IL-33 or IL-36α to determine the impact on the signaling pathways involving the three IL-1 receptors (IL-1R1, -R4 or -R6) dependent upon IL-1R3 for signaling.

The human epithelial lung cell line A549 was stimulated with IL-1α as a model of IL-1 dependent diseases such as auto-inflammatory diseases. The cell line was cultured in T75 flasks (37° C., 5% $CO_2$) in complete F-12K media (10% FCS, 1% Pen/Strep) and split on average 2 times/week, not exceeding 15 passages before assaying. A549 cells were seeded out (50.000/well) in a 96 flat-bottom plate, rested for 3 hrs before pre-incubating 1 hr with MAB-16-0030 (20 µg/mL-1 µg/mL) or IL-1Ra (10 µg/mL). Cells were then stimulated with recombinant human IL-1α (50 µg/mL, Peprotech) for 24 hrs before harvesting supernatants and assaying for IL-6 production (Duoset ELISA, RnD Systems).

A human mast cell line (HMC-1) was investigated for IL-33-dependent induction of IL-8 production. The cell line was cultured in T75 flasks (37° C., 5% $CO_2$) in complete Iscove's modified Dulbeccos's medium (IMDM, 10% FCS, 1% Pen/Strep) and split on average 3 times/week, not having a cell density above $2*10^6$/mL nor exceeding 15 passages before assaying. HMC-1 cells were seeded out (30.000/well) in a 96 flat-bottom plate, rested for 3 hrs before pre-incubating 1 hr with MAB-16-0030 (20 µg/mL-1 µg/mL) or IL-1Ra (10 µg/mL). Cells were then stimulated with recombinant human IL-33 (20 ng/mL, RnD systems) for 24 hrs before harvesting supernatants and assaying for IL-8 production (Duoset ELISA, RnD Systems).

The impact on IL-36 signaling was investigated using a human keratinocytic cell line (HaCaT). The cell line was cultured in T75 flasks (37° C., 5% $CO_2$) in complete DMEM (10% FCS, 1% Pen/Strep) and split on average 3 times/week not exceeding 15 passages before assaying. HaCaT cells were seeded out (50.000/well) in a 96 flat-bottom plate, rested for 3 hrs before pre-incubating 1 hr with MAB-16-0030 (20 μg/mL-1 μg/mL) or IL-1Ra (10 μg/mL). Cells were then stimulated with recombinant human IL-36α (50 ng/mL, RnD systems) for 24 hrs before harvesting supernatants and assaying for IL-8 production (Duoset ELISA, RnD Systems).

Example 11: Viability and IL-6 Release of PBMC

The impact of anti-hIL-1R3 antibody MAB-16-0030 on the viability of unstimulated PBMCs (500.000/well) from three healthy donors was tested using a conventional MTT reduction assay. Briefly, PBMCs (200 μL) were incubated with either media alone or MAB-16-0030 (20 μg/mL). After 24 hrs, 3 and 5 days, PBMCs were incubated for 2 hrs with MTT (20 μL), before measuring absorbance at 570 nM on an ELISA reader. Using the known linearity between absorbance and viable cells converting MTT, the number of viable cells was calculated using media alone as the control set to 100%. At the same day of MTT analysis, supernatants from PBMCs incubated under same conditions and from same donors, were harvested and subsequently assayed for IL-6 production (Duoset ELISA, RnD systems) to evaluate any possible stimulatory effect of MAB-16-0030 alone.

Example 12: Functional Blockage of PBMCs

Freshly isolated PBMCs from healthy donors were used to evaluate the impact of MAB-16-0030 on human cells stimulated with diverse antigens. For all stimuli, the experiments were carried out using 500.000 PBMCs/well, stimulating in a total volume of 200 μL. Cells were seeded out and incubated with either media alone, MAB-16-0030 (20-0.1 μg/mL) or IL-1Ra (10 μg/mL) for 1 hr before stimulation. The following stimuli were used; LPS (10 ng/mL, 24 hrs, RPMI no FCS), anti-human CD3/CD28 (1.25 μg/mL; 0.5 μg/mL (eBioscience) 3 days, RPMI 10% FCS), IL-12/-33 (2 ng/mL; 20 ng/mL (Peprotech; RnD Systems)), 3 days, RPMI 10% FCS) or heat-inactivated *Candida albicans* ($0.5*10^6$/ mL, 5 days, RPMI 10% FCS). After stimulation, supernatants were harvested and assayed for cytokine production using Duoset ELISAs (RnD Systems) according to manufactures protocol.

Example 13: Functional Blockage of Immune Cells in Whole Blood

Heat-inactivated *Candida albicans* were used to stimulate whole blood. Freshly harvested blood from healthy donors (EDTA tubes) were distributed in micro-centrifuge tubes (250 μL/tube) and pre-incubated with either media alone (RPMI, no FCS), MAB-16-0030 (20-0.1 μg/mL) or IL-1Ra (10 μg/mL) for 1 hr before stimulation with *Candida albicans* ($0.5*10^6$/mL) to a final volume of 1 mL. After 24 hrs incubation (37° C., 5% $CO_2$), supernatants were harvested and assayed for cytokine production by ELISA (Duoset, RnD Systems).

Example 14: Mixed Lymphocyte Reactions (MLR)

PBMCs from healthy, non-matching donors were mixed in a 1:1 ratio (250.000/donor) and incubated for 5 days (RPMI, 10% FCS) with either media alone, MAB-16-0030 (20-1 μg/mL) or IL-1Ra (10 μg/mL). Cytokine production were assayed using a Quansys multiplex platform according to manufacturer's protocol.

Example 15: NFkB Luciferase Gene Reporter Assay

NFkB Luciferase Reporter NIH 3T3 cell (Signosis) were seeded out at 20,000 cells in 25 μL DMEM, 10% FCS, 1% Pen/Strep medium per well (conc.=$0.8\times10^6$ cells/mL) in white cell-culture treated, flat bottom 384 well plate. Cells were incubated over night at 37° C./5% $CO_2$. Medium was aspirated and 12.5 μL of the antibody solution with MAB-16-0531 was added to the cells at diverse concentrations. After incubation for 1 h at 37° C./5% $CO_2$, 12.5 μL mouse-IL-1β was added in medium to a final concentration of 50 μg/ml. Cells were incubated for 5 h at 37° C./5% $CO_2$. 25 μl Steady-Glo™ (Promega) solution was added to each well, mixed thoroughly and plates were incubated for 10 minutes at room temperature before luminescence was measured using a Tecan M1000 plate reader. Fitting curves and EC50 calculation were obtained by using Excel (Microsoft) and XLfit (IDBS).

Example 16: NIH-3T3 IL6-Release Assay

NIH 3T3 cell were seeded out at 12,500 cells in 15 μL DMEM+1% FCS medium per well (conc.=$0.83\times10^6$ cells/ mL) in a cell-culture treated, flat bottom 384 well plate. Cells were incubated for 2 hours at 37° C./5% $CO_2$. 10 μL antibody MAB-16-0531 was added in medium to the cells at diverse concentrations. After incubation for 1.5 h at 37° C./5% $CO_2$, 25 μL human-IL-1β was added in medium to a final concentration of 50 μg/ml. Cells were incubated over night at 37° C./5% $CO_2$. Secreted mouse-IL6 in culture supernatants was quantified by ELISA (DuoSet ELISA; R&D Systems; Cat. No. 840171) according to manufacturer's instructions. Fitting curves and EC50 calculation were done using Excel (Microsoft) and XLfit (IDBS).

Example 17: Monosodium Urate Crystal (MSU)-Induced Mouse Peritonitis Model 3 mg of MSU (Invitrogen) per mouse was used for intraperitoneal injection (I.P) as a stimulant, and anti-IL-1R3 (MAB-16-0531, 500 μg/mouse) or IL-1Ra (10 mg/kg) for inhibition. Saline was used both as control for stimulation and inhibition. The four groups were comprised of 4 mice as control of stimuli (Saline (inhib.)+Saline(stimuli)), 8 mice with MSU alone (Saline+MSU), 8 mice with MAB-16-0531 (500 μg/mouse+MSU) and 8 mice with IL-1Ra (10 mg/kg+ MSU). MAB-16-0531 and IL-1Ra were injected I.P. 1 hr before MSU stimulation. 6 hours after MSU or saline injection the mice were euthanized. Blood was collected in micro-centrifuge tubes containing EDTA and peritoneal fluid collected by lavage using 10 mL of ice-cold PBS. Bone-marrow cells were isolated, and organs immediately frozen in liquid nitrogen. The number of cells in the peritoneal fluid was counted (HESKA HemaTrue).

Example 18: Neutrophil Activation and Cytokine Production in MSU Peritonitis Neutrophils are the most abundant cell type in gout and activation correlates with elastase production. IP fluid and IP cell lysates from Example 17 were analyzed for levels of neutrophil elastase marker and MPO levels. IP lysates were prepared in TritonX 0.5%. Cytokines were measured in both IP fluid and IP cell lysates. For low abundance cytokines in the IP fluid, 8 mL of fluid was concentrated (end range: 4.7-10.9× concentrated) in pre-boiled (15 min) dialysis membranes (MWCO 3.5 kDa., Spectra/Por3 Dialysis membrane, Spectrumlabs) submerged in polyethylene glycol (MN 6-8000, Sigma Aldrich) as the hygroscopic solution at 4° C. Initial concentrations were calculated by dividing with the dialysis concentration factor. Spleen and whole blood lysates were assayed for cytokine levels and normalized to protein concentration of the lysates. Cytokine concentrations were measured according to protocol using Duoset ELISA (R&D Systems) or multiplex assays (Quansys Biosciences). Protein levels in spleen lysates and IP fluid were assayed with a standard Bradford assay, using protein assay dye reagent (BioRad) and BSA as standard. As shown in FIG. 20 a-c, treatment with a-mIL1R3 antibody MAB-16-0531 significantly reduces MSU-induced intracellular Elastase and Elastase in the IP fluid. IL-6, G-CSF, KC and CCL-2 levels are strongly reduced in the IP fluid in MAB-16-0531 mice. Systemically, MPO and KC are also reduced in spleen lysates, IL-6 and G-CSF are reduced in plasma (FIG. 20 d).

Example 19: OVA Allergic Asthma In Vivo Model

An OVA-induced allergic asthma model has been applied as an IL-33 dependent in vivo model. Wildtype 6 weeks old C57BL/6 male mice (Jackson Laboratories) were sensitized IP using OVA (15 g/100 µL, Sigma-Aldrich) mixed 1:1 with Imject Alum Adjuvant (100 µL, ThermoFischer). Mice were injected at day 1, 14 and 21. At day 25-28 mice were injected IP with MAB-16-0531 (500 µg/mouse, MAB Discovery) or mouse IgG2a-LALA control (500 µg/mouse, MAB Discovery, groups "Vehicle" and "OVA"). Intratracheal instillation of OVA (50 g/mouse in 50 L) was done 30 min post-injection at day 26-28 in short-term carbon dioxide anesthesia. Bronchoalveolar lavage (BAL) was carried out by inserting a catheter into the trachea and washing the airways with 3×1 ml washes. This was followed by cell phenotyping using flow cytometry. The following monoclonal antibodies (mAbs) against mouse targets were used for flow cytometry following mouse Fc Block (BD Biosciences): PE-Cy7 CD11c (N418), PerCP-Cy5.5 CD11b (M1/70), FITC-Ly6G (1A8-Ly6G) (all from eBioscience); PE-Siglec-F (E250-4440) (from BD Biosciences) (stained in DPBS containing 10 mg/ml BSA, 0.1 mg/ml NaN$_3$). Cells were analyzed on a Canto II flow cytometer using FlowJo software (Treestar). BAL cells were enumerated by trypan blue exclusion. Following BAL, lungs were inflated with pre-warmed 3% low melt agarose in DPBS and allowed to cool before removal into phosphate buffered formalin overnight. Lungs were embedded in paraffin, sectioned and stained with H&E and PAS. Histology was evaluated using a Leica DM2000 LED microscope and LAS V4.12 software. FIG. 21 a-b shows that MAB-16-0531 treatment significantly reduced total BAL white blood cell count (WBC), eosinophils and neutrophils. In FIG. 21 c, lung section HE staining confirm a reduced pathology by MAB-16-0531 treatment and PAS staining demonstrates a reduced amount of mucus producing goblet cells in the airways (PAS).

Example 20: Imiquimod Induced Psoriasis In Vivo Model

IL-36 has a prominent role in skin inflammation and mutations in the IL-36Ra are linked to human pustular psoriasis. Therefore, application of an anti-IL1R3 therapy to skin inflammatory diseases has been tested using an imiquimod induced psoriasis in vivo model. WT twelve weeks old C57BL/6 mice (Jackson Laboratories) were back-skin shaved and treated with hair removal cream (Nair). Application of 75 mg IMQ (Aldara 5% IMQ) or control cream (Vaseline cream) was done daily (day 1-5) on back-skin (IMQ; IMQ (n=10) and a-mIL1R3 (n=9) group, control cream; vehicle group (n=3)) and IP injections every other day (day 1, 3 and 5). Vehicle and IMQ groups received mouse IgG control (20 mg/kg, MAB Discovery), treatment group received MAB-16-0531 (20 mg/kg, MAB Discovery). Ears were concurrently applied with control cream on left ear (all mice; 5 mg Vaseline cream) and group appropriate stimuli cream on right ear (Vehicle; 5 mg Vaseline cream, IMQ and a-mIL1R3; 5 mg IMQcream).

Body weight was monitored daily. Mice were euthanized day 6, left and right ear thickness was measured using a gauge. Whole blood cell counts were assessed using a HemaTrue analyzer (HESKA). Pictures of back-skin were visually scored (erythema and scaling, score 0 (no response) to 4 (maximum affected)) by 6 blinded people. RNA was isolated from skin puncture biopsies. RNA was extracted from lysates and cDNA was produced from 0.8 µg RNA (NanoDrop) (High Capacity cDNA Reverse Transcription Kit (Applied Biosystems)). 50 ng cDNA was used in real time qPCR reaction using SYBR Green master mix (Applied Biosystems) and 0.1 µM of cytokine specific primer. GAPDH was used as reference gene, and ratios calculated using the Pfaffl method including analyzed primer efficiencies.

Myeloperoxidase (MPO) levels were measured in a freshly obtained skin biopsy by ELISA. MPO levels were normalized to total protein measurements (determined by the Bradford method). FIGS. 22 and 23 demonstrate that treatment with MAB-16-0531 significantly reduces imiquimod-induced skin inflammation which is also associated with a reduction in skin granulocyte infiltration, MPO levels and IL17F mRNA expression.

Example 21: Activation of Fc-Receptor Mediated Effector Function by IgG1 and IgG1-LALA Anti-IL1R3 Antibodies To test the activity of IgG-1 and IgG1-LALA versions of a humanized anti-IL1R3 antibody in eliciting Fc-mediated effector cell functions such as ADCC, MAB-16-0030 was produced as an IgG1 or IgG1-LALA antibody. hIL1R3 expressing target cells SK-MEL-30 cells were seeded in a 384-well tissue-culture treated plate at a density of 2500 cells/well in 25 µl RPMI medium containing 10% FCS. 24 h after seeding, 4000 effector cells/well (ADCC Bioassay Effector cells, Jurkat, Promega Cat. #G701A) were added in RPMI medium containing 4% low-IgG-FCS. Antibodies were then added to final concentrations ranging from 10000 to 0.002 ng/ml and the plate was incubated for 6 hours at 37° C. and 5% CO$_2$. Activation of NF-kB signaling in luciferase gene reporter Jurkat cells was measured according to manufacturer's instructions (Bio-Glo Luciferase Assay) and using a Tecan M1000 microplate reader. "Fold of induction" values represent RLU (antibody treated−background)/RLU (no antibody control−background). Fitting curves and EC50 calculation were obtained by using Excel (Microsoft) and XLfit (IDBS). As shown in FIG. 24, only the IgG1-version of MAB-16-0030 induces NF-kB signaling in effector Jurkat reporter cells, while effector cell activation with the IgG1-LALA version is abolished.

FIGURE LEGEND

FIG. 1: Sequences (amino acids in one letter code) Complete sequences of Variable Regions (VR):

| Heavy chain: | VH complete: | SEQ ID NO: 1-34 and SEQ ID NO: 173 and 176 |
|---|---|---|
| Light chain: | VL complete: | SEQ ID NO: 35-68 and SEQ ID NO: 174 and 177 |

Complementary Determining Regions (CDR):

| Heavy Chain: | CDRH1: | SEQ ID NO: 69-85 and 178 |
|---|---|---|
| | CDRH2: | SEQ ID NO: 86-102 and 179 |
| | CDRH3: | SEQ ID NO: 103-119 and 180 |
| Light Chain: | CDRL1: | SEQ ID NO: 120-136 and 181 |
| | CDRL2: | SEQ ID NO: 137-153 and 182 |
| | CDRL3: | SEQ ID NO: 154-170 and 175 and 183 |

Constant Regions (CR):

| Light Chain: | CR-L: | SEQ ID NO: 171 |
|---|---|---|
| Heavy Chain: | CR-H: | SEQ ID NO: 172 |

In the following Figures, AF676 is a commercial polyclonal antibody preparation purchased from the following link: https://www.rndsystems.com/products/human-il-1-racp-il-1-r3-antibody_af676

FIG. 2: Human IL-1R3 ELISA

A 384-microtiter plate was coated with human Il-1R3 protein representing the human extracellular domain of IL-1R3 (0.5 mg/ml, at least 1 h). After an intensive washing step followed by a blocking step, antibodies were added (12.5 µl per well) and incubated for 1 h at RT. Unbound antibody was washed out intensively. The amount of bound antibody was identified by incubating the microtiter plate with a Peroxidase labelled anti-human detection antibody (1 h at RT). The Peroxidase reaction was initiated by adding TMB and measuring the absorbance at 450 nm/620 nm.

FIG. 3: HEK293 reporter assay

HEK293T/17-FR cells were stable transfected with the pGL4.32[luc2P/NF-κB-RE/Hygro] vector (Promega) and seeded in 384 well PDL Costar Cell Culture plates followed by 30 min incubation with the antibodies. The cells were then stimulated with IL-1ß for 5 hours before the NF-kB activity was determined using the Steady-Glo Luciferase Assay Kit (Promega) according to manufacturer's protocol.

FIG. 4: NFκB luciferase reporter assay using an A549 stable cell line

A549-NFkB-RE-Luc stable transfected cells (purchased from Signosis) have been cultivated for 3 days (1.7E+04 cells/cm³). 384-well low flange white flat bottom polystyrene TC-treated microtiter plates (Corning) were filled with $4 \times 10^4$ cells per well. After a cultivation period of 10 h the cells were incubated with the antibodies for 1 h before the cells were stimulated with 10 µl IL-1β for another 5 h. NFkB modulation has been measured by Steady-Glo™ Luciferase Assay System (Promega) determining relative luminescence units of each well in relation to non-stimulated cells.

FIG. 5: Cell binding analysis: Binding to IL-1R3 expressing cells

Humanized anti-IL-1R3 IgG1-LALA antibodies were tested for binding to cell lines with different IL-1R3 receptor densities using flow cytometry. Humanized anti-IL-1R3

IgG1-LALA antibodies bind to low- and high-IL-1R3-expressing cell lines. Antibodies do not bind to mouse NIH-3T3 cells. Experiments were carried out according to the method described in Example 4.

FIG. 6: Cell binding analysis: Cell binding on human-IL-1R3 high expressing cell line SK-MEL-30

EC50 cell binding values of humanized anti-IL-1R3 IgG1-LALA antibodies were determined by binding to high-IL-1R3-expressing cell line SK-MEL-30 using flow cytometry. Humanized anti-IL-1R3 IgG1-LALA antibodies MAB-16-0030 and MAB-16-0149 show cell binding of 307 and 306 ng/ml, respectively. Experiments were carried out according to the method described in Example 4.

FIG. 7: Human-IL-1R3 biochemical ELISA

Binding of humanized anti-IL-1R3 IgG1-LALA antibodies to recombinant human IL-1R3 protein was tested in biochemical ELISA. Exemplified antibodies show EC50 binding values of 16.3 ng/ml and 29.1 ng/ml, respectively. Experiments were carried out according to the method described in Example 5.

FIG. 8: Inhibition of human IL-1a and IL-1b mediated NfKB signaling in A549-NFkB-RE-Luc cells Functional neutralization of IL-1a and IL-1b was tested in a cell based gene reporter assay using A549-NFkB-RE-Luc cells stimulated with 0.1 ng/ml IL-1a and IL-1b, respectively. Humanized anti-IL-1R3 IgG1-LALA antibodies show EC50 values superior to that of goat-anti-human-IL1-R3 polyclonal antibody AF676 (R&D Systems). Experiments were carried out according to the method described in Example 6.

FIG. 9: IL-1α and IL-1β functional neutralization assay—Inhibition of human IL-1a and IL-1b mediated IL-6 release by A-549 cells Neutralization of IL-1a and IL-1b mediated cellular release of IL-6 by humanized anti-IL-1R3 IgG1-LALA antibodies was tested using A-549 cells. EC50 values demonstrate that humanized anti-IL-1R3 IgG1-LALA antibodies are superior to that of goat-anti-human-IL1-R3 polyclonal antibody AF676 (R&D Systems). Experiments were carried out according to the method described in Example 7.

FIG. 10: IL-33 functional neutralization assay—Inhibition of human IL-33 mediated NfkB-signaling in HEK-Blue-IL33™ cells Neutralization of IL-33 mediated cell signaling by humanized anti-IL-1R3 IgG1-LALA antibodies was tested using IL-33 stimulated gene reporter HEK-Blue-IL33™ cells (InvivoGen). EC50 values demonstrate that humanized anti-IL-1R3 IgG1-LALA antibodies are superior to that of goat-anti-human-IL1-R3 polyclonal antibody AF676 (R&D Systems). Experiments were carried out according to the method described in Example 8.

FIG. 11: IL-36 functional neutralization assay—Inhibition of human IL-36 mediated NfkB-signaling in HEK-293/17-IF cells Neutralization of IL-36 mediated cell signaling by humanized anti-IL-1R3 IgG1-LALA antibodies was tested using IL-36g stimulated gene reporter HEK-293/17-IF cells. Typical humanized anti-IL-1R3 IgG1-LALA antibodies show EC50 values superior to that of goat-anti-human-IL1-R3 polyclonal antibody AF676 (R&D Systems). Experiments were carried out according to the method described in Example 9.

FIG. 12: Neutralization of IL-1a, IL-33 and IL-36a mediated cellular cytokine release Neutralization of IL-1a, IL-33 and IL-36a mediated cellular cytokine release was tested using specific IL-1a, IL-33 and IL-36a dependent cell systems. The Inhibition of cytokine release by A representative humanized anti-IL-1R3 IgG1-LALA antibody according to the invention (MAB-16-0030) was tested and compared to IL-1Ra. While the antibody according to the invention was able to inhibit cytokine release mediated by all three stimuli, IL-1Ra affected only IL-1a mediated cytokine release. Experiments were carried out according to the method described in Example 10.

FIG. 13: Viability and IL-6 release of unstimulated PBMC treated with a humanized anti-IL-1R3 IgG1-LALA antibody Binding of antibodies to immune cells may result in cell depleting and deleterious effects, e.g. by direct induction of apoptotic signaling pathways, stimulation of excessive cytokine release or antibody-dependent cellular cytotoxicity (ADCC). To exclude that humanized anti-IL-1R3 IgG1-LALA antibodies directly affect the viability of PBMCs, the viability of PBMCs of three donors and IL-6 release was investigated after incubation with different concentrations of a representative humanized anti-IL-1R3 IgG1-LALA antibody according to the invention (MAB-16-0030) for 1, 3 and 5 days. Neither viability nor IL-6 release was affected. These results support that the humanized anti-IL-1R3 IgG1-LALA antibodies block IL-1R3 function on immune cells without circumstantial cell-depletion and induction of cell-deleterious effects. Experiments were carried out according to the method described in Example 11.

FIG. 14: Functional blockage of PBMCs activated with different stimuli

To test whether humanized anti-IL-1R3 IgG1-LALA antibodies inhibit activation of PBMCs stimulated with specific or complex stimuli, PBMCs of 10 donors were stimulated with LPS, heat-inactivated *Candida albicans*, IL-12/IL-33 or anti-CD3/CD28 antibodies. A representative humanized anti-IL-1R3 IgG1-LALA antibody according to the invention (MAB-16-0030) was able to inhibit cytokine release mediated by all tested stimuli. Experiments were carried out according to the method described in Example 12.

FIG. 15: Functional blockage of immune cells in whole blood activated with *Candida albicans*

To test whether humanized anti-IL-1R3 IgG1-LALA antibodies inhibit activation of immune cells in whole blood, whole blood of 8 donors was stimulated with heat-inactivated *Candida albicans*. A representative humanized anti-IL-1R3 IgG1-LALA antibody according to the invention (MAB-16-0030) was able to inhibit *Candida* induced IL-6 cytokine release. Experiments were carried out according to the method described in Example 13.

FIG. 16: Blockage of cytokine release in Mixed Lymphocyte Reactions (MLR) The ability of humanized anti-IL-1R3 IgG1-LALA antibodies to block release of diverse cytokines was tested in mixed lymphocyte reactions (MLR) using PBMCs of healthy, unmatched donors. A representative humanized anti-IL-1R3 IgG1-LALA antibody according to the invention (MAB-16-0030) was able to inhibit release of IFNg, IL-6, TNF-α, IL-13, IL-17 and IL-10. Experiments were carried out according to the method described in Example 14.

FIG. 17: Neutralization of IL-1b mediated signaling in murine cells

Functional neutralization of IL-1b by an anti-mouse-IL-1R3 antibody according to the invention was tested using a mouse NIH-3T3 cell based NFkB luciferase gene reporter assay. A representative antibody according to the invention (MAB-16-0531) showed dose-dependent inhibition of IL-1b mediated NFkB signaling with an EC50 of 805 ng/ml. Experiments were carried out according to the method described in Example 15.

FIG. 18: Neutralization of IL-1b mediated IL-6 release from murine cells

Inhibition of IL-6 release from mouse cells by an anti-mouse-IL-1R3 antibody according to the invention was tested in IL-1b stimulated NIH-3T3 cells. A representative antibody according to the invention (MAB-16-0531) showed dose-dependent inhibition of IL-6 release with an EC50 of 1560 ng/ml. Experiments were carried out according to the method described in Example 16.

FIG. 19: Monosodium urate crystal (MSU)-induced mouse peritonitis model

To test the rationale of applying an anti-IL-R3 therapy to gout patients, a monosodium urate crystal (MSU)-induced mouse peritonitis model was used. The administration of MSU produces a strong inflammatory response in the peritoneal cavity, inducing the influx of several inflammatory cells (such as monocytes and neutrophils), mimicking a classic inflammatory profile of an acute gout response. A representative anti-IL1R3 antibody according to the invention (MAB-16-0531) or IL-1Ra were administered I.P. one hour before injection of 3 mg MSU in the peritoneum. Measurements of cells in the peritoneal cavity show that anti-IL-1R3 antibody treatment significantly inhibits MSU induced infiltration of lymphocytes, monocytes and granulocytes. Experiments were carried out according to the method described in Example 17.

FIG. 20: Neutrophil activation and cytokine production in MSU peritonitis

Attenuation of neutrophil activation including local and systemic markers of inflammation in MSU peritonitis. (a) Levels of the neutrophil protease Elastase in IP fluid. (b) Total levels of intracellular Elastase in cells from IP fluid. (c) Total levels of intracellular MPO in cells from IP fluid. (d) Cyto- and chemokine concentrations locally (IP fluid) and systemically. WB; lysed whole blood, norm.; normalized per mg of protein in spleen. MSU; vehicle+MSU. a-mIL1R3; a-mIL1R3+MSU. IL 1Ra; IL 1Ra+MSU. Inhibitor treated groups compared to MSU stimulated group. *p<0.05, p<0.01, *p<0.001, ****p<0.0001 (Student's t-test, mean+SEM, except: (b), G CSF, KC (WB) and KC (spleen); Mann-Whitney U-test, median with IQR).

FIG. 21: OVA allergic asthma in vivo model a-mIL1R3 antibody decreases OVA induced cell influx in vivo. (a) Total WBC from BAL fluid. (b) Flow defined cell differentials from (a). (c) Histology from group average (WBC) thick dot marked mice using H&E and PAS stained lung tissue. Comparisons between OVA stimulated+a-mIL1R3 (MAB-16-0531) treated mice and OVA alone. *p<0.05, p<0.01, *p<0.001 (Student's t-test). Mean+SEM.

FIG. 22: Imiquimod psoriasis in vivo model (a) IL 36a mRNA induction in skin. (b) Fold change in ear thickness between IMQ and control cream applied ears. (c) Visual scoring by n=6 blinded people at end of study (0; unaffected-4; maximum affected (erythema and scaling)). (d) MPO concentration in skin, normalized per mg of protein. (e) Spearman correlation between data from (c) and (d). (e) Granulocyte concentrations in whole blood. Comparisons between inhibitor treated and IMQ stimulated groups. *p<0.05, p<0.01, *p<0.001, ****p<0.0001, ((b,f) Mann-Whitney U-test (d,e) Student's t-test, mean±SEM except (d) median with IQR).

FIG. 23: Imiquimod psoriasis in vivo model

IL36α/β/γ, IL17F and TNFa mRNA levels in skin biopsies of imiquimod-treated mice FIG. 24: Effector cell mediated function of anti-IL1R3 IgG1 and IgG1-LALA antibodies Anti-IL1R3 antibody MAB-16-0030, either containing an IgG1-LALA or an IgG1 Fc-part was tested for activation of Fc-receptor mediated NF-kB signaling in effector cells. Binding of increasing concentrations of the IgG1 antibody to hIL1R3 expressing SK-MEL-30 cells elicit Fc-receptor 5 mediated signaling in Jurkat gene reporter effector cells in contrast to the IgG1-LALA antibody

The invention claimed is:

1. A method for treating a neutrophilic inflammatory disorder in a subject, comprising administering to the subject an antibody, or antigen binding fragment thereof, that specifically binds IL-1R3, wherein the antibody or antigen binding fragment comprises: a) a heavy chain variable region (VH) comprising the complementarity determining regions comprising CDR-H1, CDR-H2, and CDR-H3, wherein the CDR-H1 region comprises an amino acid sequence set forth in SEQ ID NO: 79, wherein the CDR-H2 region comprises an amino acid sequence set forth in SEQ ID NO: 96, and wherein the CDR-H3 region comprises an amino acid sequence set forth in SEQ ID NO: 113; and b) a light chain variable region (VL) comprising the complementarity determining regions comprising CDR-L1, CDR-L2, and CDR-L3, wherein the CDR-L1 region comprises an amino acid sequence set forth in SEQ ID NO: 130, wherein the CDR-L2 region comprises an amino acid sequence set forth in SEQ ID NO: 147, and wherein the CDR-L3 region comprises an amino acid sequence set forth in SEQ ID NO: 175, thereby treating the neutrophilic inflammatory disorder in the subject.

2. The method of claim 1, wherein the antibody comprises a human IgG1 Fc region.

3. The method of claim 2, wherein the human IgG1 Fc region comprises at least amino acid substitutions L234A and L235A, wherein the numbering of amino acid residues in the Fc region is according to the EU numbering system.

4. The method of claim 1, wherein the VH region is at least 90% identical to the amino acid sequence set forth in SEQ ID NO: 28, and the VL region is at least 90% identical to the amino acid sequence set forth in SEQ ID NO: 174.

5. The method of claim 1, wherein the antibody comprises a human IgG4 Fc region.

6. The method of claim 5, wherein the human IgG4 Fc region comprises at least amino acid substitutions S228P and L235E, wherein the numbering of amino acid residues in the Fc region is according to the EU numbering system.

7. A method for attenuating neutrophil activation in a subject, comprising administering to the subject an antibody, or antigen binding fragment thereof, that specifically binds IL-1R3, wherein the antibody or antigen binding fragment comprises: a) a heavy chain variable region (VH) comprising the complementarity determining regions comprising CDR-H1, CDR-H2, and CDR-H3, wherein the CDR-H1 region comprises an amino acid sequence set forth in SEQ ID NO: 79, wherein the CDR-H2 region comprises an amino acid sequence set forth in SEQ ID NO: 96, and wherein the CDR-H3 region comprises an amino acid sequence set forth in SEQ ID NO: 113; and b) a light chain variable region (VL) comprising the complementarity determining regions comprising CDR-L1, CDR-L2, and CDR-L3, wherein the CDR-L1 region comprises an amino acid sequence set forth in SEQ ID NO: 130, wherein the CDR-L2 region comprises an amino acid sequence set forth in SEQ ID NO: 147, and wherein the CDR-L3 region comprises an amino acid sequence set forth in SEQ ID NO: 175, thereby attenuating neutrophil activation in the subject.

8. The method of claim 7, wherein the antibody comprises a human IgG1 Fc region.

9. The method of claim 8, wherein the human IgG1 Fc region comprises at least amino acid substitutions L234A and L235A, wherein the numbering of amino acid residues in the Fc region is according to the EU numbering system.

10. The method of claim 7, wherein the VH region is at least 90% identical to the amino acid sequence set forth in SEQ ID NO: 28, and the VL region is at least 90% identical to the amino acid sequence set forth in SEQ ID NO: 174.

11. The method of claim 10, wherein the human IgG4 Fc region comprises at least amino acid substitutions S228P and L235E, wherein the numbering of amino acid residues in the Fc region is according to the EU numbering system.

12. The method of claim 7, wherein the antibody comprises a human IgG4 Fc region.

\* \* \* \* \*

```
                          SEQUENCE LISTING

Sequence total quantity: 183
SEQ ID NO: 1              moltype = AA   length = 118
FEATURE                   Location/Qualifiers
REGION                    1..118
                          note = humanized antibody
source                    1..118
                          mol_type = protein
                          organism = synthetic construct
SEQUENCE: 1
EVQLEESGGG LVQPGGSLRL SCAASGFSFS SSYWICWVRQ APGKGLEWVS CIYTGSGGTY 60
YASWEKGRFT ISRDNSKNTL YLQMNSLRAE DTAVYFCARD PGYSSWLWGQ GTLVTVSS   118

SEQ ID NO: 2              moltype = AA   length = 122
FEATURE                   Location/Qualifiers
REGION                    1..122
                          note = humanized antibody
source                    1..122
                          mol_type = protein
                          organism = synthetic construct
SEQUENCE: 2
EVQLEESGGD LVQPGGSLRL SCAASGFSFS SSHYMCWVRQ APGKGLEWVS CIYAGSSGNT 60
YYANWAKGRF TISRDNSKNT LYLQMNSLRA EDTAVYFCAR VDASSSGSWD LWGQGTLVTV 120
SS                                                                122

SEQ ID NO: 3              moltype = AA   length = 123
FEATURE                   Location/Qualifiers
REGION                    1..123
                          note = humanized antibody
source                    1..123
                          mol_type = protein
                          organism = synthetic construct
SEQUENCE: 3
EVQLEESGGR LVQPGGSLRL SCAVSGIDLS SYAMGWVRQA PGKGLEYVSV ITSSATTYYA 60
SWAKGRFTIS RDNSKNTLYL QMNSLRAEDT AVYFCARGGP GYSTNTHYAF DPWGQGTLVT 120
VSS                                                               123

SEQ ID NO: 4              moltype = AA   length = 119
FEATURE                   Location/Qualifiers
REGION                    1..119
                          note = humanized antibody
source                    1..119
                          mol_type = protein
                          organism = synthetic construct
SEQUENCE: 4
EVQLEESGGR VVQPGRSLRL SCAVSGIDLD NYAMGWVRQA PGKGLEYVAV ISSDGFFYDA 60
SWAKGRFTIS RDNSKNTLYL QMNSLRAEDT AVYFCARDRG TSTGSLDLWG QGTLVTVSS  119

SEQ ID NO: 5              moltype = AA   length = 125
FEATURE                   Location/Qualifiers
REGION                    1..125
                          note = humanized antibody
source                    1..125
                          mol_type = protein
                          organism = synthetic construct
SEQUENCE: 5
EVQLEESGGR LVQPGGSLRL SCAASGFSLS SYYMSWVRQA PGKGLEWVSI ISGSASTYYA 60
TWAKGRFTIS RDNSKNTLYL QMNSLRAEDT AVYFCARTHY AAVAGYGYAS RLDLWGQGTL 120
VTVSS                                                             125

SEQ ID NO: 6              moltype = AA   length = 120
FEATURE                   Location/Qualifiers
REGION                    1..120
                          note = humanized antibody
source                    1..120
                          mol_type = protein
                          organism = synthetic construct
SEQUENCE: 6
EVQLEESGGD LVQPGGSLRL SCAASGFSFS SNYWICWVRQ APGKGLELVS CIYTSTGNTW 60
YASWAKGRFT ISRDNSKNTL YLQMNSLRAE DTAVYFCARD LLVVTSFNLW GQGTLVTVSS 120
```

-continued

```
SEQ ID NO: 7              moltype = AA  length = 120
FEATURE                   Location/Qualifiers
REGION                    1..120
                          note = humanized antibody
source                    1..120
                          mol_type = protein
                          organism = synthetic construct
SEQUENCE: 7
EVQLEESGGD LVQPGGSLRL SCAASGFSFS SSYYMCWVRQ APGKGLEWVS CIYAGSSGVT  60
YYASWAKGRF TISRDNSKNT LYLQMNSLRA EDTAVYFCAS ETDGNYFNLW GQGTLVTVSS  120

SEQ ID NO: 8              moltype = AA  length = 120
FEATURE                   Location/Qualifiers
REGION                    1..120
                          note = humanized antibody
source                    1..120
                          mol_type = protein
                          organism = synthetic construct
SEQUENCE: 8
EVQLEQSGGG LVQPGGSLRL SCAASGFSLS TSYWRCWVRQ APGKGLEWVS CIYAGSGDVT  60
YYANWVNGRF TISRDNSKNT LYLQMNSLRA EDTAVYYCAS GVGFGYFNLW GQGTLVTVSS  120

SEQ ID NO: 9              moltype = AA  length = 122
FEATURE                   Location/Qualifiers
REGION                    1..122
                          note = humanized antibody
source                    1..122
                          mol_type = protein
                          organism = synthetic construct
SEQUENCE: 9
EVQLEESGGG LVQPGGSLRL SCAASGIDFS SYYYMCWVRQ APGKGLEWVS CIFIGYGDVT  60
WYASWAKGRF TISRDNSKNT LYLQMNSLRA EDTAVYFCAR ALGSSGYRVN LWGQGTLVTV  120
SS                                                                 122

SEQ ID NO: 10             moltype = AA  length = 115
FEATURE                   Location/Qualifiers
REGION                    1..115
                          note = humanized antibody
source                    1..115
                          mol_type = protein
                          organism = synthetic construct
SEQUENCE: 10
EVQLEESGGR LVQPGGSLRL SCAASGFSLS SYWMSWVRQA PGKGLEWVSM IYGSGYTYYA  60
SWAKGRFTIS RDNSKNTLYL QMNSLRAEDT AVYFCARDPQ YFILWGQGTL VTVSS       115

SEQ ID NO: 11             moltype = AA  length = 120
FEATURE                   Location/Qualifiers
REGION                    1..120
                          note = humanized antibody
source                    1..120
                          mol_type = protein
                          organism = synthetic construct
SEQUENCE: 11
EVQLEESGGR LVQPGGSLRL SCAVSGFSLS SYDMSWVRQA PGKGLEWVST IYIGGTTAYA  60
SWPKGRFTIS RDNSKNTLYL QMNSLRAEDT AVYFCARLQG ANYYNSLALW GQGTLVTVSS  120

SEQ ID NO: 12             moltype = AA  length = 120
FEATURE                   Location/Qualifiers
REGION                    1..120
                          note = humanized antibody
source                    1..120
                          mol_type = protein
                          organism = synthetic construct
SEQUENCE: 12
EVQLVESGGG LVQPGGSLRL SCAASGFDFS SNYYMCWVRQ APGKGLELVS CIYTNSGNTW  60
SASWAKGRFT ISRDNSKNTL YLQMNSLRAE DTAVYFCARD LNYPDTSNLW GQGTLVTVSS  120

SEQ ID NO: 13             moltype = AA  length = 119
FEATURE                   Location/Qualifiers
REGION                    1..119
                          note = humanized antibody
source                    1..119
                          mol_type = protein
                          organism = synthetic construct
SEQUENCE: 13
EVQLEESGGD LVQPGGSLRL SCAASGFSFS FGYYMCWVRQ APGKGLEWVS CIYGDSSDTL  60
YANWAKGRFT ISRDNSKNTL YLQMNSLRAE DTAVYFCARY PGGSYYNLWG QGTLVTVSS   119
```

```
SEQ ID NO: 14            moltype = AA   length = 122
FEATURE                  Location/Qualifiers
REGION                   1..122
                         note = humanized antibody
source                   1..122
                         mol_type = protein
                         organism = synthetic construct
SEQUENCE: 14
EVQLEESGGD LVQPGGSLRL SCAASGFSFS STYYMCWVRQ APGKGLEWVS CIYAGSSGST   60
YYASWAKGRF TISRDNSKNT LYLQMNSLRA EDTAVYFCAR VDGSSSGSWD LWGQGTLVTV  120
SS                                                                 122

SEQ ID NO: 15            moltype = AA   length = 122
FEATURE                  Location/Qualifiers
REGION                   1..122
                         note = humanized antibody
source                   1..122
                         mol_type = protein
                         organism = synthetic construct
SEQUENCE: 15
EVQLEESGGD LVQPGGSLRL SCAASGISFS SSDFMCWVRQ APGKGLEWVS CIYAGSSVSI   60
YYATWAKGRF TISRDNSKNT LYLQMNSLRA EDTAVYFCAR STGSVGRGFN LWGQGTLVTV  120
SS                                                                 122

SEQ ID NO: 16            moltype = AA   length = 121
FEATURE                  Location/Qualifiers
REGION                   1..121
                         note = humanized antibody
source                   1..121
                         mol_type = protein
                         organism = synthetic construct
SEQUENCE: 16
EVQLVESGGG LVQPGGSLRL SCAASGFSFS SIYYMCWVRQ APGKGLEWVS CIYTGNSDFT   60
YYANWAKGRF TISRDNSKNT LYLQMNSLRA EDTAVYFCAR FRDDYASLKL WGQGTLVTVS  120
S                                                                  121

SEQ ID NO: 17            moltype = AA   length = 120
FEATURE                  Location/Qualifiers
REGION                   1..120
                         note = humanized antibody
source                   1..120
                         mol_type = protein
                         organism = synthetic construct
SEQUENCE: 17
EVQLEESGGG LVQPGGSLRL SCAASGFSFS SGYDMCWVRQ APGKGLEWVS CIYTGSGSTY   60
YANWAKGRFT ISRDNSKNTL YLQMNSLRAE DTAVYFCARN SNDWMYFNLW GQGTLVTVSS  120

SEQ ID NO: 18            moltype = AA   length = 117
FEATURE                  Location/Qualifiers
REGION                   1..117
                         note = humanized antibody
source                   1..117
                         mol_type = protein
                         organism = synthetic construct
SEQUENCE: 18
EVQLEQSGGG LVQPGGSLRL SCAASGFSFS SSYWICWVRQ APGKGLEWVA CIYTGSGGTY   60
YASWEKGRFT ISKTSSTTLY LQMNSLRAED TAVYFCARDP GYSSWLWGQG TLVTVSS     117

SEQ ID NO: 19            moltype = AA   length = 122
FEATURE                  Location/Qualifiers
REGION                   1..122
                         note = humanized antibody
source                   1..122
                         mol_type = protein
                         organism = synthetic construct
SEQUENCE: 19
EVQLEESGGD LVQPGASLRL SCAASGFSFS SSHYMCWVRQ APGKGLEWVA CIYAGSSGNT   60
YYANWAKGRF TISKTNSKNT LYLQMNSLRA EDTAVYFCAR VDASSSGSWD LWGQGTLVTV  120
SS                                                                 122

SEQ ID NO: 20            moltype = AA   length = 122
FEATURE                  Location/Qualifiers
REGION                   1..122
                         note = humanized antibody
source                   1..122
                         mol_type = protein
                         organism = synthetic construct
SEQUENCE: 20
EVQLLESGGR LVQPGTSLRL SCAVSGIDLS SYAMGWVRQA PGKGLEYVGV ITSSATTYYA   60
```

-continued

```
SWAKGRFTIS KTSSTTLYLQ MNSLRAEDTA VYFCARGGPG YSTNTHYAFD PWGQGTLVTV    120
SS                                                                   122

SEQ ID NO: 21                moltype = AA  length = 119
FEATURE                      Location/Qualifiers
REGION                       1..119
                             note = humanized antibody
source                       1..119
                             mol_type = protein
                             organism = synthetic construct
SEQUENCE: 21
EVQLEESGGR VVQPGTSLRL SCAVSGIDLD NYAMGWVRQA PGKGLEYVAV ISSDGFFYDA    60
SWAKGRFTIS KANSKNTLYL QMNSLRAEDT AVYFCARDRG TSTGSLDLWG QGTLVTVSS     119

SEQ ID NO: 22                moltype = AA  length = 123
FEATURE                      Location/Qualifiers
REGION                       1..123
                             note = humanized antibody
source                       1..123
                             mol_type = protein
                             organism = synthetic construct
SEQUENCE: 22
QVQLEESGGR LVQPGTSLRL SCAASGFSLS SYYMSWVRQA PGKGLEWVAI ISGSASTYYA    60
TWAKGRFTIS KTSTTLYLQM NSLRAEDTAV YFCARTHYAA VAGYGYASRL DLWGQGTLVT    120
VSS                                                                  123

SEQ ID NO: 23                moltype = AA  length = 120
FEATURE                      Location/Qualifiers
REGION                       1..120
                             note = humanized antibody
source                       1..120
                             mol_type = protein
                             organism = synthetic construct
SEQUENCE: 23
QVQLQESGGD LVQPGGSLRL SCAASGFSFS SNYWICWVRQ APGKGLELVA CIYTSTGNTW    60
YASWAKGRFT ISRDNSKNTL YLQMNSLRAE DTAVYFCARD LLVVTSFNLW GQGTLVTVSS    120

SEQ ID NO: 24                moltype = AA  length = 119
FEATURE                      Location/Qualifiers
REGION                       1..119
                             note = humanized antibody
source                       1..119
                             mol_type = protein
                             organism = synthetic construct
SEQUENCE: 24
EVQLVESGGD LVQPGASLRL SCAASGFSFS SSYYMCWVRQ APGKGLEWVA CIYAGSSGVT    60
YYASWAKGRF TISDTSSTTL YLQMNSLRAE DTAVYFCASE TDGNYFNLWG QGTLVTVSS     119

SEQ ID NO: 25                moltype = AA  length = 120
FEATURE                      Location/Qualifiers
REGION                       1..120
                             note = humanized antibody
source                       1..120
                             mol_type = protein
                             organism = synthetic construct
SEQUENCE: 25
EVQLEQSGGG LVQPGGSLRL SCAASGFSLS TSYWRCWVRQ APGKGLEWVA CIYAGSGDVT    60
YYANWVNGRF TISRDNSKST LYLQMNSLRA EDTAVYYCAS GVGFGYFNLW GQGTLVTVSS    120

SEQ ID NO: 26                moltype = AA  length = 122
FEATURE                      Location/Qualifiers
REGION                       1..122
                             note = humanized antibody
source                       1..122
                             mol_type = protein
                             organism = synthetic construct
SEQUENCE: 26
EVQLEESGGG LVQPGGSLRL SCAASGIDFS SYYYMCWVRQ APGKGLEWVA CIFIGYGDVT    60
WYASWAKGRF TISKANSKNT LYLQMNSLRA EDTAVYFCAR ALGSSGYRVN LWGQGTLVTV    120
SS                                                                   122

SEQ ID NO: 27                moltype = AA  length = 113
FEATURE                      Location/Qualifiers
REGION                       1..113
                             note = humanized antibody
source                       1..113
                             mol_type = protein
                             organism = synthetic construct
SEQUENCE: 27
```

```
QVQLEESGGR LVQPGASLRL SCAASGFSLS SYWMSWVRQA PGKGLEWVAM IYGSGYTYYA  60
SWAKGRFTIS TTSTTLYLQM NSLRAEDTAV YFCARDPQYF ILWGQGTLVT VSS         113

SEQ ID NO: 28              moltype = AA  length = 120
FEATURE                    Location/Qualifiers
REGION                     1..120
                           note = humanized antibody
source                     1..120
                           mol_type = protein
                           organism = synthetic construct
SEQUENCE: 28
EVQLEESGGR LVQPGTSLRL SCAVSGFSLS SYDMSWVRQA PGKGLEWVST IYIGGTTAYA  60
SWPKGRFTIS KTNSKNTLYL QMNSLRAEDT AVYFCARLQG ANYYNSLALW GQGTLVTVSS  120

SEQ ID NO: 29              moltype = AA  length = 119
FEATURE                    Location/Qualifiers
REGION                     1..119
                           note = humanized antibody
source                     1..119
                           mol_type = protein
                           organism = synthetic construct
SEQUENCE: 29
QVQLVESGGG LVQPGGSLRL SCAASGFDFS SNYYMCWVRQ APGKGLELVA CIYTNSGNTW  60
SASWAKGRFT ISKTNSTTLY LQMNSLRAED TAVYFCARDL NYPDTSNLWG QGTLVTVSS   119

SEQ ID NO: 30              moltype = AA  length = 119
FEATURE                    Location/Qualifiers
REGION                     1..119
                           note = humanized antibody
source                     1..119
                           mol_type = protein
                           organism = synthetic construct
SEQUENCE: 30
EVQLEESGGD LVQPGGSLRL SCAASGFSFS FGYYMCWVRQ APGKGLEWVA CIYGDSSDTL  60
YANWAKGRFT ISKTNSKNTL YLQMNSLRAE DTAVYFCARY PGGSYYNLWG QGTLVTVSS   119

SEQ ID NO: 31              moltype = AA  length = 120
FEATURE                    Location/Qualifiers
REGION                     1..120
                           note = humanized antibody
source                     1..120
                           mol_type = protein
                           organism = synthetic construct
SEQUENCE: 31
QVQLQESGGD LVQPGASLRL SCAASGFSFS STYYMCWVRQ APGKGLEWVA CIYAGSSGST  60
YYASWAKGRF TISKNSSTLY LQMNSLRAED TAVYFCARVD GSSSGSWDLW GQGTLVTVSS  120

SEQ ID NO: 32              moltype = AA  length = 121
FEATURE                    Location/Qualifiers
REGION                     1..121
                           note = humanized antibody
source                     1..121
                           mol_type = protein
                           organism = synthetic construct
SEQUENCE: 32
EVQLEESGGD LVQPGASLRL SCAASGISFS SSDFMCWVRQ APGKGLEWVA CIYAGSSVSI  60
YYATWAKGRF TISKASSTTL YLQMNSLRAE DTAVYFCARS TGSVGRGFNL WGQGTLVTVS  120
S                                                                  121

SEQ ID NO: 33              moltype = AA  length = 121
FEATURE                    Location/Qualifiers
REGION                     1..121
                           note = humanized antibody
source                     1..121
                           mol_type = protein
                           organism = synthetic construct
SEQUENCE: 33
EVQLVESGGG LVQPGGSLRL SCAASGFSFS SIYYMCWVRQ APGKGLEWVG CIYTGNSDFT  60
YYANWAKGRF TISRDNSKST LYLQMNSLRA EDTAVYFCAR FRDDYASLKL WGQGTLVTVS  120
S                                                                  121

SEQ ID NO: 34              moltype = AA  length = 120
FEATURE                    Location/Qualifiers
REGION                     1..120
                           note = humanized antibody
source                     1..120
                           mol_type = protein
                           organism = synthetic construct
SEQUENCE: 34
```

-continued

```
QVQLQESGGG LVQPGGSLRL SCTASGFSFS SGYDMCWVRQ APGKGLEWVG CIYTGSGSTY    60
YANWAKGRFT ISKDNSKTTL YLQMNSLRAE DTAVYFCARN SNDWMYFNLW GQGTLVTVSS    120

SEQ ID NO: 35              moltype = AA  length = 110
FEATURE                    Location/Qualifiers
REGION                     1..110
                           note = humanized antibody
source                     1..110
                           mol_type = protein
                           organism = synthetic construct
SEQUENCE: 35
DIVMTQSPSS LSASVGDRVT ITCQASESIS NYLSWYQQKP GQAPKLLIYL ASTLASGVPS    60
RFSGSGSGTD FTLTISSLQP EDFATYYCQN WWVIEHNGAA FGGGTKVVIK               110

SEQ ID NO: 36              moltype = AA  length = 110
FEATURE                    Location/Qualifiers
REGION                     1..110
                           note = humanized antibody
source                     1..110
                           mol_type = protein
                           organism = synthetic construct
SEQUENCE: 36
DIQMTQSPSS LSASVGDRVT ITCQASESIY SNLAWYQQKP GQAPKLLIYA ASLLASGVPS    60
RFSGSGSGTD FTLTISSLQP EDFATYYCQS ASYSTGPDWT FGQGTKVVIK               110

SEQ ID NO: 37              moltype = AA  length = 110
FEATURE                    Location/Qualifiers
REGION                     1..110
                           note = humanized antibody
source                     1..110
                           mol_type = protein
                           organism = synthetic construct
SEQUENCE: 37
DIQMTQSPSS LSASVGDRVT ITCQASQSIY IYLSWYQQKP GQAPKLLIYD ASKLASGVPS    60
RFSGSGSGTD FTLTISSLQP EDFATYYCQQ GATTYNVDNV FGQGTKVVIK               110

SEQ ID NO: 38              moltype = AA  length = 111
FEATURE                    Location/Qualifiers
REGION                     1..111
                           note = humanized antibody
source                     1..111
                           mol_type = protein
                           organism = synthetic construct
SEQUENCE: 38
DIVMTQSPSS LSASVGDRVT ITCQASENIG NGLAWYQQKP GQAPKLLIYG ASTLASGVPS    60
RFSGSGSGTD FTLTISSLQP EDFATYYCQC TYWNPDYIGG AFGGGTKVVI K             111

SEQ ID NO: 39              moltype = AA  length = 110
FEATURE                    Location/Qualifiers
REGION                     1..110
                           note = humanized antibody
source                     1..110
                           mol_type = protein
                           organism = synthetic construct
SEQUENCE: 39
DIQMTQSPSS LSASVGDRVT ITCLASEDIY SGISWYQQKP GKAPKLLIYA ASNLESGVPS    60
RFSGSGSGTD FTLTISSLQP EDFATYYCLG GYSYSNTGPT FGQGTKVEIK               110

SEQ ID NO: 40              moltype = AA  length = 113
FEATURE                    Location/Qualifiers
REGION                     1..113
                           note = humanized antibody
source                     1..113
                           mol_type = protein
                           organism = synthetic construct
SEQUENCE: 40
DIVMTQSPSS LSASVGDRVT ITCQASEDIY SNLAWFQQKP GQAPKLLIYG ASTLASGVPS    60
RFSGSGSGTE FTLTISSLQP EDFATYYCLG VCTDISTDDL YNAFGQGTKV VIK           113

SEQ ID NO: 41              moltype = AA  length = 110
FEATURE                    Location/Qualifiers
REGION                     1..110
                           note = humanized antibody
source                     1..110
                           mol_type = protein
                           organism = synthetic construct
SEQUENCE: 41
DIVMTQSPSS LSASVGDRVT ITCQASEDIY SNLAWFQQKP GQAPKLLIYR ASTLASGVPS    60
RFSGSGSGTE FTLTISSLQP EDFATYYCLG VYTYSTDIHA FGGGTKVVIK               110
```

```
SEQ ID NO: 42            moltype = AA  length = 110
FEATURE                  Location/Qualifiers
REGION                   1..110
                         note = humanized antibody
source                   1..110
                         mol_type = protein
                         organism = synthetic construct
SEQUENCE: 42
DIVMTQSPSS LSASVGDRVT ITCQASEDIY SNLAWFQQKP GQAPKLLIYD ASTLASGVPS   60
RFSGSGSGTE FTLTISSLQP EDFATYYCLG VYTHISADNA FGGGTKVVIK              110

SEQ ID NO: 43            moltype = AA  length = 111
FEATURE                  Location/Qualifiers
REGION                   1..111
                         note = humanized antibody
source                   1..111
                         mol_type = protein
                         organism = synthetic construct
SEQUENCE: 43
DIQMTQSPSS LSASVGDRVT ITCQASENIY SSLAWYQQKP GQAPKLLIYD ASDLASGVPS   60
RFSGSGSGTD FTLTISSLQP EDFATYYCQQ GYYSGGTDND VFGGGTKVVI K           111

SEQ ID NO: 44            moltype = AA  length = 112
FEATURE                  Location/Qualifiers
REGION                   1..112
                         note = humanized antibody
source                   1..112
                         mol_type = protein
                         organism = synthetic construct
SEQUENCE: 44
DIVMTQSPSS LSASVGDRVT ITCQSSQSVD GNNLLSWYQQ KPGQAPKLLI YDASNLASGV   60
PSRFSGSGSG TDFTLTISSL QPEDFATYYC QGSYYSSSWY NVFGQGTKVV IK          112

SEQ ID NO: 45            moltype = AA  length = 108
FEATURE                  Location/Qualifiers
REGION                   1..108
                         note = humanized antibody
source                   1..108
                         mol_type = protein
                         organism = synthetic construct
SEQUENCE: 45
DIQMTQSPSS LSASVGDRVT ITCQASQSIY SFLSWYQQKP GQAPKLLIYA ASDLESGVPS   60
RFSGSGSGTD FTLTISSLQP EDFATYYCQN YIIDYGAFG QGTKVVIK               108

SEQ ID NO: 46            moltype = AA  length = 108
FEATURE                  Location/Qualifiers
REGION                   1..108
                         note = humanized antibody
source                   1..108
                         mol_type = protein
                         organism = synthetic construct
SEQUENCE: 46
DIQMTQSPSS LSASVGDRVT ITCQASQSIG YYLAWYQQKP GQAPKLLIYR ASTLASGVPS   60
RFSGSGSGTD FTLTISSLQP EDFATYYCQS YYNSDSDAFG QGTKVVIK               108

SEQ ID NO: 47            moltype = AA  length = 110
FEATURE                  Location/Qualifiers
REGION                   1..110
                         note = humanized antibody
source                   1..110
                         mol_type = protein
                         organism = synthetic construct
SEQUENCE: 47
DIVMTQSPSS LSASVGDRVT ITCQASQTIS INLAWYQQKP GQAPKLLIYY ASTLASGVPS   60
RFSGSGSGTD FTLTISSLQP EDFATYYCQQ GYTEDNIDNT FGQGTKVVIK             110

SEQ ID NO: 48            moltype = AA  length = 110
FEATURE                  Location/Qualifiers
REGION                   1..110
                         note = humanized antibody
source                   1..110
                         mol_type = protein
                         organism = synthetic construct
SEQUENCE: 48
DIQMTQSPSS LSASVGDRVT ITCQASQNIY SNLAWYQQKP GQAPKLLIYA ASLLASGVPS   60
RFSGSGSGTD FTLTISSLQP EDFATYYCQG AVYSGNTEWA FGQGTKVVIK             110

SEQ ID NO: 49            moltype = AA  length = 113
```

-continued

```
FEATURE              Location/Qualifiers
REGION               1..113
                     note = humanized antibody
source               1..113
                     mol_type = protein
                     organism = synthetic construct
SEQUENCE: 49
DIVMTQSPSS LSASVGDRVT ITCQASQSVY NSNHLSWYQQ KPGQAPKLLI YSASTLASGV  60
PSRFSGSGSG TDFTLTISSL QPEDFATYYC QGEFSCVSAD CIAFGGGTKV VIK         113

SEQ ID NO: 50        moltype = AA   length = 110
FEATURE              Location/Qualifiers
REGION               1..110
                     note = humanized antibody
source               1..110
                     mol_type = protein
                     organism = synthetic construct
SEQUENCE: 50
DIQMTQSPSS LSASVGDRVT ITCQASQSIS SYLSWYQQKP GQAPKLLIYG ASNLASGVPS  60
RFSGSGSGTD FTLTISSLQP EDFATYYCQC TYYDNNYGGA FGGGTKVVIK             110

SEQ ID NO: 51        moltype = AA   length = 114
FEATURE              Location/Qualifiers
REGION               1..114
                     note = humanized antibody
source               1..114
                     mol_type = protein
                     organism = synthetic construct
SEQUENCE: 51
DIVMTQSPSS LSASVGDRVT ITCQASESIS ANYWSWYQQK PGQAPKLLIY GASTLASGVP  60
SRFSGSGSGT DFTLTISSLQ PEDFATYFCQ SWYYSGSGSY HSWAFGQGTK VVIK        114

SEQ ID NO: 52        moltype = AA   length = 110
FEATURE              Location/Qualifiers
REGION               1..110
                     note = humanized antibody
source               1..110
                     mol_type = protein
                     organism = synthetic construct
SEQUENCE: 52
DIVMTQSPSS LSASVGDRVT ITCQASESIS NYLSWYQQKP GQAPKLLIYL ASTLASGVPS  60
RFSGSGSGTD FTLTISSLQP EDFATYYCQN WWVIEHNGAA FGGGTKVVIK             110

SEQ ID NO: 53        moltype = AA   length = 110
FEATURE              Location/Qualifiers
REGION               1..110
                     note = humanized antibody
source               1..110
                     mol_type = protein
                     organism = synthetic construct
SEQUENCE: 53
AIQMTQSPSS LSASVGDRVT ITCQASESIY SNLAWYQQKP GQAPKLLIYA ASLLASGVPS  60
RFSGSGSGTD YTLTISSLQP EDFATYYCQS ASYSTGPDWT FGQGTKVVIK             110

SEQ ID NO: 54        moltype = AA   length = 110
FEATURE              Location/Qualifiers
REGION               1..110
                     note = humanized antibody
source               1..110
                     mol_type = protein
                     organism = synthetic construct
SEQUENCE: 54
AIRMTQSPSS LSASVGDRVT ITCQASQSIY IYLSWYQQKP GQAPKLLIYD ASKLASGVPS  60
RFSGSGSGTD FTLTISSLQP EDFATYYCQQ GATTYNVDNV FGQGTKVVIK             110

SEQ ID NO: 55        moltype = AA   length = 111
FEATURE              Location/Qualifiers
REGION               1..111
                     note = humanized antibody
source               1..111
                     mol_type = protein
                     organism = synthetic construct
SEQUENCE: 55
ELVMTQSPSS LSASVGDRVT ITCQASENIG NGLAWYQQKP GQAPKLLIYG ASTLASGVPS  60
RFSGSGSGTD FTLTISSLQP EDFATYYCQC TYWNPDYIGG AFGGGTKVVI K           111

SEQ ID NO: 56        moltype = AA   length = 110
FEATURE              Location/Qualifiers
REGION               1..110
```

-continued

```
                              note = humanized antibody
source                        1..110
                              mol_type = protein
                              organism = synthetic construct
SEQUENCE: 56
AIQMTQSPSS LSASVGDRVT ITCLASEDIY SGISWYQQKP GKAPKLLIYA ASNLESGVPS  60
RFSGSGSGTD YTLTISSLQP EDFATYYCLG GYSYSNTGPT FGQGTKVEIK              110

SEQ ID NO: 57                 moltype = AA   length = 113
FEATURE                       Location/Qualifiers
REGION                        1..113
                              note = humanized antibody
source                        1..113
                              mol_type = protein
                              organism = synthetic construct
SEQUENCE: 57
DIVMTQSPSS LSASVGDRVT ITCQASEDIY SNLAWFQQKP GQAPKLLIYG ASTLASGVPS  60
RFSGSGSGTE FTLTISSLQP EDFATYYCLG VCTDISTDDL YNAFGQGTKV VIK          113

SEQ ID NO: 58                 moltype = AA   length = 110
FEATURE                       Location/Qualifiers
REGION                        1..110
                              note = humanized antibody
source                        1..110
                              mol_type = protein
                              organism = synthetic construct
SEQUENCE: 58
DIVMTQSPSS LSASVGDRVT ITCQASEDIY SNLAWFQQKP GQAPKLLIYR ASTLASGVPS  60
RFSGSGSGTE FTLTISSLQP EDFATYYCLG VYTYSTDIHA FGGGTKVVIK             110

SEQ ID NO: 59                 moltype = AA   length = 110
FEATURE                       Location/Qualifiers
REGION                        1..110
                              note = humanized antibody
source                        1..110
                              mol_type = protein
                              organism = synthetic construct
SEQUENCE: 59
ELVMTQSPSS LSASVGDRVT ITCQASEDIY SNLAWFQQKP GQAPKLLIYD ASTLASGVPS  60
RFSGSGSGTE FTLTISSLQP EDFATYYCLG VYTHISADNA FGGGTKVEIK             110

SEQ ID NO: 60                 moltype = AA   length = 111
FEATURE                       Location/Qualifiers
REGION                        1..111
                              note = humanized antibody
source                        1..111
                              mol_type = protein
                              organism = synthetic construct
SEQUENCE: 60
ALQMTQSPSS LSASVGDRVT ITCQASENIY SSLAWYQQKP GQAPKLLIYD ASDLASGVPS  60
RFSGSGSGTD FTLTISSLQP EDFATYYCQQ GYYSGGTDND VFGGGTKVVI K           111

SEQ ID NO: 61                 moltype = AA   length = 112
FEATURE                       Location/Qualifiers
REGION                        1..112
                              note = humanized antibody
source                        1..112
                              mol_type = protein
                              organism = synthetic construct
SEQUENCE: 61
NIVMTQSPSS LSASVGDRVT ITCQSSQSVD GNNLLSWYQQ KPGQAPKLLI YDASNLASGV  60
PSRFSGSGSG TDFTLTISSL QPEDFATYYC QGSYYSSSWY NVFGQGTKVV IK          112

SEQ ID NO: 62                 moltype = AA   length = 108
FEATURE                       Location/Qualifiers
REGION                        1..108
                              note = humanized antibody
source                        1..108
                              mol_type = protein
                              organism = synthetic construct
SEQUENCE: 62
DVQMTQSPSS LSASVGDRVT ITCQASQSIY SFLSWYQQKP GQAPKLLIYA ASDLESGVPS  60
RFSGSGSGTD FTLTISSLQP EDFATYYCQC NYIIDYGAFG QGTKVVIK               108

SEQ ID NO: 63                 moltype = AA   length = 108
FEATURE                       Location/Qualifiers
REGION                        1..108
                              note = humanized antibody
source                        1..108
```

```
                          mol_type = protein
                          organism = synthetic construct
SEQUENCE: 63
DIQMTQSPSS LSASVGDRVT ITCQASQSIG YYLAWYQQKP GQAPKLLIYR ASTLASGVPS  60
RFSGSGSGTD FTLTISSLQP EDFATYYCQS YYNSDSDAFG QGTKVVIK               108

SEQ ID NO: 64            moltype = AA  length = 110
FEATURE                  Location/Qualifiers
REGION                   1..110
                          note = humanized antibody
source                   1..110
                          mol_type = protein
                          organism = synthetic construct
SEQUENCE: 64
AIVMTQSPSS LSASVGDRVT ITCQASQTIS INLAWYQQKP GQAPKLLIYY ASTLASGVPS  60
RFSGSGSGTD FTLTISSLQP EDFATYYCQQ GYTEDNIDNT FGQGTKVVIK             110

SEQ ID NO: 65            moltype = AA  length = 110
FEATURE                  Location/Qualifiers
REGION                   1..110
                          note = humanized antibody
source                   1..110
                          mol_type = protein
                          organism = synthetic construct
SEQUENCE: 65
AIQMTQSPSS LSASVGDRVT ITCQASQNIY SNLAWYQQKP GQAPKLLIYA ASLLASGVPS  60
RFSGSGSGTD YTLTISSLQP EDFATYYCQG AVYSGNTEWA FGQGTKVVIK             110

SEQ ID NO: 66            moltype = AA  length = 113
FEATURE                  Location/Qualifiers
REGION                   1..113
                          note = humanized antibody
source                   1..113
                          mol_type = protein
                          organism = synthetic construct
SEQUENCE: 66
DIVMTQSPSS LSASVGDRVT ITCQASQSVY NSNHLSWYQQ KPGQAPKLLI YSASTLASGV  60
PSRFSGSGSG TDFTLTISSL QPEDFATYYC QGEFSCVSAD CIAFGGGTKV VIK         113

SEQ ID NO: 67            moltype = AA  length = 110
FEATURE                  Location/Qualifiers
REGION                   1..110
                          note = humanized antibody
source                   1..110
                          mol_type = protein
                          organism = synthetic construct
SEQUENCE: 67
DVVMTQSPSS LSASVGDRVT ITCQASQSIS SYLSWYQQKP GQAPKLLIYG ASNLASGVPS  60
RFSGSGSGTD FTLTISSLQP EDFATYYCQC TYYDNNYGGA FGGGTKVEIK             110

SEQ ID NO: 68            moltype = AA  length = 114
FEATURE                  Location/Qualifiers
REGION                   1..114
                          note = humanized antibody
source                   1..114
                          mol_type = protein
                          organism = synthetic construct
SEQUENCE: 68
DIVMTQSPSS LSASVGDRVT ITCQASESIS ANYWSWYQQK PGQAPKLLIY GASTLASGVP  60
SRFSGSGSGT DFTLTISSLQ PEDFATYFCQ SWYYSGSGSY HSWAFGQGTK VVIK        114

SEQ ID NO: 69            moltype = AA  length = 6
FEATURE                  Location/Qualifiers
REGION                   1..6
                          note = humanized antibody
source                   1..6
                          mol_type = protein
                          organism = synthetic construct
SEQUENCE: 69
SSYWIC                                                              6

SEQ ID NO: 70            moltype = AA  length = 6
FEATURE                  Location/Qualifiers
REGION                   1..6
                          note = humanized antibody
source                   1..6
                          mol_type = protein
                          organism = synthetic construct
SEQUENCE: 70
```

-continued

```
SSHYMC                                                               6

SEQ ID NO: 71          moltype = AA  length = 5
FEATURE                Location/Qualifiers
REGION                 1..5
                       note = humanized antibody
source                 1..5
                       mol_type = protein
                       organism = synthetic construct
SEQUENCE: 71
SYAMG                                                                5

SEQ ID NO: 72          moltype = AA  length = 5
FEATURE                Location/Qualifiers
REGION                 1..5
                       note = humanized antibody
source                 1..5
                       mol_type = protein
                       organism = synthetic construct
SEQUENCE: 72
NYAMG                                                                5

SEQ ID NO: 73          moltype = AA  length = 5
FEATURE                Location/Qualifiers
REGION                 1..5
                       note = humanized antibody
source                 1..5
                       mol_type = protein
                       organism = synthetic construct
SEQUENCE: 73
SYYMS                                                                5

SEQ ID NO: 74          moltype = AA  length = 6
FEATURE                Location/Qualifiers
REGION                 1..6
                       note = humanized antibody
source                 1..6
                       mol_type = protein
                       organism = synthetic construct
SEQUENCE: 74
SNYWIC                                                               6

SEQ ID NO: 75          moltype = AA  length = 6
FEATURE                Location/Qualifiers
REGION                 1..6
                       note = humanized antibody
source                 1..6
                       mol_type = protein
                       organism = synthetic construct
SEQUENCE: 75
SSYYMC                                                               6

SEQ ID NO: 76          moltype = AA  length = 6
FEATURE                Location/Qualifiers
REGION                 1..6
                       note = humanized antibody
source                 1..6
                       mol_type = protein
                       organism = synthetic construct
SEQUENCE: 76
TSYWRC                                                               6

SEQ ID NO: 77          moltype = AA  length = 6
FEATURE                Location/Qualifiers
REGION                 1..6
                       note = humanized antibody
source                 1..6
                       mol_type = protein
                       organism = synthetic construct
SEQUENCE: 77
SYYYMC                                                               6

SEQ ID NO: 78          moltype = AA  length = 5
FEATURE                Location/Qualifiers
REGION                 1..5
                       note = humanized antibody
source                 1..5
                       mol_type = protein
                       organism = synthetic construct
```

```
SEQUENCE: 78
SYWMS                                                                    5

SEQ ID NO: 79          moltype = AA   length = 5
FEATURE                Location/Qualifiers
REGION                 1..5
                       note = humanized antibody
source                 1..5
                       mol_type = protein
                       organism = synthetic construct
SEQUENCE: 79
SYDMS                                                                    5

SEQ ID NO: 80          moltype = AA   length = 6
FEATURE                Location/Qualifiers
REGION                 1..6
                       note = humanized antibody
source                 1..6
                       mol_type = protein
                       organism = synthetic construct
SEQUENCE: 80
SNYYMC                                                                   6

SEQ ID NO: 81          moltype = AA   length = 6
FEATURE                Location/Qualifiers
REGION                 1..6
                       note = humanized antibody
source                 1..6
                       mol_type = protein
                       organism = synthetic construct
SEQUENCE: 81
FGYYMC                                                                   6

SEQ ID NO: 82          moltype = AA   length = 6
FEATURE                Location/Qualifiers
REGION                 1..6
                       note = humanized antibody
source                 1..6
                       mol_type = protein
                       organism = synthetic construct
SEQUENCE: 82
STYYMC                                                                   6

SEQ ID NO: 83          moltype = AA   length = 6
FEATURE                Location/Qualifiers
REGION                 1..6
                       note = humanized antibody
source                 1..6
                       mol_type = protein
                       organism = synthetic construct
SEQUENCE: 83
SSDFMC                                                                   6

SEQ ID NO: 84          moltype = AA   length = 6
FEATURE                Location/Qualifiers
REGION                 1..6
                       note = humanized antibody
source                 1..6
                       mol_type = protein
                       organism = synthetic construct
SEQUENCE: 84
SIYYMC                                                                   6

SEQ ID NO: 85          moltype = AA   length = 6
FEATURE                Location/Qualifiers
REGION                 1..6
                       note = humanized antibody
source                 1..6
                       mol_type = protein
                       organism = synthetic construct
SEQUENCE: 85
SGYDMC                                                                   6

SEQ ID NO: 86          moltype = AA   length = 17
FEATURE                Location/Qualifiers
REGION                 1..17
                       note = humanized antibody
source                 1..17
                       mol_type = protein
```

-continued

```
                               organism = synthetic construct
SEQUENCE: 86
CIYTGSGGTY YASWEKG                                                17

SEQ ID NO: 87       moltype = AA   length = 18
FEATURE             Location/Qualifiers
REGION              1..18
                    note = humanized antibody
source              1..18
                    mol_type = protein
                    organism = synthetic construct
SEQUENCE: 87
CIYAGSSGNT YYANWAKG                                               18

SEQ ID NO: 88       moltype = AA   length = 16
FEATURE             Location/Qualifiers
REGION              1..16
                    note = humanized antibody
source              1..16
                    mol_type = protein
                    organism = synthetic construct
SEQUENCE: 88
VITSSATTYY ASWAKG                                                 16

SEQ ID NO: 89       moltype = AA   length = 16
FEATURE             Location/Qualifiers
REGION              1..16
                    note = humanized antibody
source              1..16
                    mol_type = protein
                    organism = synthetic construct
SEQUENCE: 89
VISSDGFFYD ASWAKG                                                 16

SEQ ID NO: 90       moltype = AA   length = 16
FEATURE             Location/Qualifiers
REGION              1..16
                    note = humanized antibody
source              1..16
                    mol_type = protein
                    organism = synthetic construct
SEQUENCE: 90
IISGSASTYY ATWAKG                                                 16

SEQ ID NO: 91       moltype = AA   length = 17
FEATURE             Location/Qualifiers
REGION              1..17
                    note = humanized antibody
source              1..17
                    mol_type = protein
                    organism = synthetic construct
SEQUENCE: 91
CIYTSTGNTW YASAWKG                                                17

SEQ ID NO: 92       moltype = AA   length = 18
FEATURE             Location/Qualifiers
REGION              1..18
                    note = humanized antibody
source              1..18
                    mol_type = protein
                    organism = synthetic construct
SEQUENCE: 92
CIYAGSSGVT YYASWAKG                                               18

SEQ ID NO: 93       moltype = AA   length = 18
FEATURE             Location/Qualifiers
REGION              1..18
                    note = humanized antibody
source              1..18
                    mol_type = protein
                    organism = synthetic construct
SEQUENCE: 93
CIYAGSGDVT YYANWVNG                                               18

SEQ ID NO: 94       moltype = AA   length = 18
FEATURE             Location/Qualifiers
REGION              1..18
                    note = humanized antibody
source              1..18
```

```
                            mol_type = protein
                            organism = synthetic construct
SEQUENCE: 94
CIFIGYGDVT WYASWAKG                                                18

SEQ ID NO: 95             moltype = AA  length = 16
FEATURE                   Location/Qualifiers
REGION                    1..16
                          note = humanized antibody
source                    1..16
                          mol_type = protein
                          organism = synthetic construct
SEQUENCE: 95
MIYGSGYTYY ASWAKG                                                  16

SEQ ID NO: 96             moltype = AA  length = 16
FEATURE                   Location/Qualifiers
REGION                    1..16
                          note = humanized antibody
source                    1..16
                          mol_type = protein
                          organism = synthetic construct
SEQUENCE: 96
TIYIGGTTAY ASWPKG                                                  16

SEQ ID NO: 97             moltype = AA  length = 17
FEATURE                   Location/Qualifiers
REGION                    1..17
                          note = humanized antibody
source                    1..17
                          mol_type = protein
                          organism = synthetic construct
SEQUENCE: 97
CIYTNSGNTW SASWAKG                                                 17

SEQ ID NO: 98             moltype = AA  length = 17
FEATURE                   Location/Qualifiers
REGION                    1..17
                          note = humanized antibody
source                    1..17
                          mol_type = protein
                          organism = synthetic construct
SEQUENCE: 98
CIYGDSSDTL YANWAKG                                                 17

SEQ ID NO: 99             moltype = AA  length = 18
FEATURE                   Location/Qualifiers
REGION                    1..18
                          note = humanized antibody
source                    1..18
                          mol_type = protein
                          organism = synthetic construct
SEQUENCE: 99
CIYAGSSGST YYASWAKG                                                18

SEQ ID NO: 100            moltype = AA  length = 18
FEATURE                   Location/Qualifiers
REGION                    1..18
                          note = humanized antibody
source                    1..18
                          mol_type = protein
                          organism = synthetic construct
SEQUENCE: 100
CIYAGSSVSI YYATWAKG                                                18

SEQ ID NO: 101            moltype = AA  length = 18
FEATURE                   Location/Qualifiers
REGION                    1..18
                          note = humanized antibody
source                    1..18
                          mol_type = protein
                          organism = synthetic construct
SEQUENCE: 101
CIYTGNSDFT YYANWAKG                                                18

SEQ ID NO: 102            moltype = AA  length = 17
FEATURE                   Location/Qualifiers
REGION                    1..17
                          note = humanized antibody
```

-continued

```
source                    1..17
                          mol_type = protein
                          organism = synthetic construct
SEQUENCE: 102
CIYTGSGSTY YANWAKG                                              17

SEQ ID NO: 103            moltype = AA   length = 8
FEATURE                   Location/Qualifiers
REGION                    1..8
                          note = humanized antibody
source                    1..8
                          mol_type = protein
                          organism = synthetic construct
SEQUENCE: 103
DPGYSSWL                                                        8

SEQ ID NO: 104            moltype = AA   length = 11
FEATURE                   Location/Qualifiers
REGION                    1..11
                          note = humanized antibody
source                    1..11
                          mol_type = protein
                          organism = synthetic construct
SEQUENCE: 104
VDASSSGSWD L                                                    11

SEQ ID NO: 105            moltype = AA   length = 15
FEATURE                   Location/Qualifiers
REGION                    1..15
                          note = humanized antibody
source                    1..15
                          mol_type = protein
                          organism = synthetic construct
SEQUENCE: 105
GGPGYSTNTH YAFDP                                                15

SEQ ID NO: 106            moltype = AA   length = 11
FEATURE                   Location/Qualifiers
REGION                    1..11
                          note = humanized antibody
source                    1..11
                          mol_type = protein
                          organism = synthetic construct
SEQUENCE: 106
DRGTSTGSLD L                                                    11

SEQ ID NO: 107            moltype = AA   length = 17
FEATURE                   Location/Qualifiers
REGION                    1..17
                          note = humanized antibody
source                    1..17
                          mol_type = protein
                          organism = synthetic construct
SEQUENCE: 107
THYAAVAGYG YASRLDL                                              17

SEQ ID NO: 108            moltype = AA   length = 10
FEATURE                   Location/Qualifiers
REGION                    1..10
                          note = humanized antibody
source                    1..10
                          mol_type = protein
                          organism = synthetic construct
SEQUENCE: 108
DLLVVTSFNL                                                      10

SEQ ID NO: 109            moltype = AA   length = 9
FEATURE                   Location/Qualifiers
REGION                    1..9
                          note = humanized antibody
source                    1..9
                          mol_type = protein
                          organism = synthetic construct
SEQUENCE: 109
ETDGNYFNL                                                       9

SEQ ID NO: 110            moltype = AA   length = 9
FEATURE                   Location/Qualifiers
REGION                    1..9
```

-continued

```
                              note = humanized antibody
source                        1..9
                              mol_type = protein
                              organism = synthetic construct
SEQUENCE: 110
GVGFGYFNL                                                        9

SEQ ID NO: 111                moltype = AA  length = 11
FEATURE                       Location/Qualifiers
REGION                        1..11
                              note = humanized antibody
source                        1..11
                              mol_type = protein
                              organism = synthetic construct
SEQUENCE: 111
ALGSSGYRVN L                                                     11

SEQ ID NO: 112                moltype = AA  length = 7
FEATURE                       Location/Qualifiers
REGION                        1..7
                              note = humanized antibody
source                        1..7
                              mol_type = protein
                              organism = synthetic construct
SEQUENCE: 112
DPQYFIL                                                          7

SEQ ID NO: 113                moltype = AA  length = 12
FEATURE                       Location/Qualifiers
REGION                        1..12
                              note = humanized antibody
source                        1..12
                              mol_type = protein
                              organism = synthetic construct
SEQUENCE: 113
LQGANYYNSL AL                                                    12

SEQ ID NO: 114                moltype = AA  length = 10
FEATURE                       Location/Qualifiers
REGION                        1..10
                              note = humanized antibody
source                        1..10
                              mol_type = protein
                              organism = synthetic construct
SEQUENCE: 114
DLNYPDTSNL                                                       10

SEQ ID NO: 115                moltype = AA  length = 9
FEATURE                       Location/Qualifiers
REGION                        1..9
                              note = humanized antibody
source                        1..9
                              mol_type = protein
                              organism = synthetic construct
SEQUENCE: 115
YPGGSYYNL                                                        9

SEQ ID NO: 116                moltype = AA  length = 11
FEATURE                       Location/Qualifiers
REGION                        1..11
                              note = humanized antibody
source                        1..11
                              mol_type = protein
                              organism = synthetic construct
SEQUENCE: 116
VDGSSSGSWD L                                                     11

SEQ ID NO: 117                moltype = AA  length = 11
FEATURE                       Location/Qualifiers
REGION                        1..11
                              note = humanized antibody
source                        1..11
                              mol_type = protein
                              organism = synthetic construct
SEQUENCE: 117
STGSVGRGFN L                                                     11

SEQ ID NO: 118                moltype = AA  length = 10
FEATURE                       Location/Qualifiers
```

```
REGION                    1..10
                          note = humanized antibody
source                    1..10
                          mol_type = protein
                          organism = synthetic construct
SEQUENCE: 118
FRDDYASLKL                                                                         10

SEQ ID NO: 119            moltype = AA  length = 10
FEATURE                   Location/Qualifiers
REGION                    1..10
                          note = humanized antibody
source                    1..10
                          mol_type = protein
                          organism = synthetic construct
SEQUENCE: 119
NSNDWMYFNL                                                                         10

SEQ ID NO: 120            moltype = AA  length = 11
FEATURE                   Location/Qualifiers
REGION                    1..11
                          note = humanized antibody
source                    1..11
                          mol_type = protein
                          organism = synthetic construct
SEQUENCE: 120
QASESISNYL S                                                                       11

SEQ ID NO: 121            moltype = AA  length = 11
FEATURE                   Location/Qualifiers
REGION                    1..11
                          note = humanized antibody
source                    1..11
                          mol_type = protein
                          organism = synthetic construct
SEQUENCE: 121
QASESIYSNL A                                                                       11

SEQ ID NO: 122            moltype = AA  length = 11
FEATURE                   Location/Qualifiers
REGION                    1..11
                          note = humanized antibody
source                    1..11
                          mol_type = protein
                          organism = synthetic construct
SEQUENCE: 122
QASQSIYIYL S                                                                       11

SEQ ID NO: 123            moltype = AA  length = 11
FEATURE                   Location/Qualifiers
REGION                    1..11
                          note = humanized antibody
source                    1..11
                          mol_type = protein
                          organism = synthetic construct
SEQUENCE: 123
QASENIGNGL A                                                                       11

SEQ ID NO: 124            moltype = AA  length = 11
FEATURE                   Location/Qualifiers
REGION                    1..11
                          note = humanized antibody
source                    1..11
                          mol_type = protein
                          organism = synthetic construct
SEQUENCE: 124
LASEDIYSGI S                                                                       11

SEQ ID NO: 125            moltype = AA  length = 11
FEATURE                   Location/Qualifiers
REGION                    1..11
                          note = humanized antibody
source                    1..11
                          mol_type = protein
                          organism = synthetic construct
SEQUENCE: 125
QASEDIYSNL A                                                                       11

SEQ ID NO: 126            moltype = AA  length = 11
```

-continued

```
FEATURE              Location/Qualifiers
REGION               1..11
                     note = humanized antibody
source               1..11
                     mol_type = protein
                     organism = synthetic construct
SEQUENCE: 126
QASEDIYSNL A                                                      11

SEQ ID NO: 127       moltype = AA  length = 11
FEATURE              Location/Qualifiers
REGION               1..11
                     note = humanized antibody
source               1..11
                     mol_type = protein
                     organism = synthetic construct
SEQUENCE: 127
QASEDIYSNL A                                                      11

SEQ ID NO: 128       moltype = AA  length = 11
FEATURE              Location/Qualifiers
REGION               1..11
                     note = humanized antibody
source               1..11
                     mol_type = protein
                     organism = synthetic construct
SEQUENCE: 128
QASENIYSSL A                                                      11

SEQ ID NO: 129       moltype = AA  length = 13
FEATURE              Location/Qualifiers
REGION               1..13
                     note = humanized antibody
source               1..13
                     mol_type = protein
                     organism = synthetic construct
SEQUENCE: 129
QSSQSVDGNN LLS                                                    13

SEQ ID NO: 130       moltype = AA  length = 11
FEATURE              Location/Qualifiers
REGION               1..11
                     note = humanized antibody
source               1..11
                     mol_type = protein
                     organism = synthetic construct
SEQUENCE: 130
QASQSIYSFL S                                                      11

SEQ ID NO: 131       moltype = AA  length = 11
FEATURE              Location/Qualifiers
REGION               1..11
                     note = humanized antibody
source               1..11
                     mol_type = protein
                     organism = synthetic construct
SEQUENCE: 131
QASQSIGYYL A                                                      11

SEQ ID NO: 132       moltype = AA  length = 11
FEATURE              Location/Qualifiers
REGION               1..11
                     note = humanized antibody
source               1..11
                     mol_type = protein
                     organism = synthetic construct
SEQUENCE: 132
QASQTISINL A                                                      11

SEQ ID NO: 133       moltype = AA  length = 11
FEATURE              Location/Qualifiers
REGION               1..11
                     note = humanized antibody
source               1..11
                     mol_type = protein
                     organism = synthetic construct
SEQUENCE: 133
QASQNIYSNL A                                                      11
```

-continued

```
SEQ ID NO: 134          moltype = AA   length = 13
FEATURE                 Location/Qualifiers
REGION                  1..13
                        note = humanized antibody
source                  1..13
                        mol_type = protein
                        organism = synthetic construct
SEQUENCE: 134
QASQSVYNSN HLS                                                          13

SEQ ID NO: 135          moltype = AA   length = 11
FEATURE                 Location/Qualifiers
REGION                  1..11
                        note = humanized antibody
source                  1..11
                        mol_type = protein
                        organism = synthetic construct
SEQUENCE: 135
QASQSISSYL S                                                           11

SEQ ID NO: 136          moltype = AA   length = 12
FEATURE                 Location/Qualifiers
REGION                  1..12
                        note = humanized antibody
source                  1..12
                        mol_type = protein
                        organism = synthetic construct
SEQUENCE: 136
QASESISANY WS                                                          12

SEQ ID NO: 137          moltype = AA   length = 7
FEATURE                 Location/Qualifiers
REGION                  1..7
                        note = humanized antibody
source                  1..7
                        mol_type = protein
                        organism = synthetic construct
SEQUENCE: 137
LASTLAS                                                                7

SEQ ID NO: 138          moltype = AA   length = 7
FEATURE                 Location/Qualifiers
REGION                  1..7
                        note = humanized antibody
source                  1..7
                        mol_type = protein
                        organism = synthetic construct
SEQUENCE: 138
AASLLAS                                                                7

SEQ ID NO: 139          moltype = AA   length = 7
FEATURE                 Location/Qualifiers
REGION                  1..7
                        note = humanized antibody
source                  1..7
                        mol_type = protein
                        organism = synthetic construct
SEQUENCE: 139
DASKLAS                                                                7

SEQ ID NO: 140          moltype = AA   length = 7
FEATURE                 Location/Qualifiers
REGION                  1..7
                        note = humanized antibody
source                  1..7
                        mol_type = protein
                        organism = synthetic construct
SEQUENCE: 140
GASTLAS                                                                7

SEQ ID NO: 141          moltype = AA   length = 7
FEATURE                 Location/Qualifiers
REGION                  1..7
                        note = humanized antibody
source                  1..7
                        mol_type = protein
                        organism = synthetic construct
SEQUENCE: 141
AASNLES                                                                7
```

-continued

```
SEQ ID NO: 142          moltype = AA   length = 7
FEATURE                 Location/Qualifiers
REGION                  1..7
                        note = humanized antibody
source                  1..7
                        mol_type = protein
                        organism = synthetic construct
SEQUENCE: 142
GASTLAS                                                                  7

SEQ ID NO: 143          moltype = AA   length = 7
FEATURE                 Location/Qualifiers
REGION                  1..7
                        note = humanized antibody
source                  1..7
                        mol_type = protein
                        organism = synthetic construct
SEQUENCE: 143
RASTLAS                                                                  7

SEQ ID NO: 144          moltype = AA   length = 7
FEATURE                 Location/Qualifiers
REGION                  1..7
                        note = humanized antibody
source                  1..7
                        mol_type = protein
                        organism = synthetic construct
SEQUENCE: 144
DASTLAS                                                                  7

SEQ ID NO: 145          moltype = AA   length = 7
FEATURE                 Location/Qualifiers
REGION                  1..7
                        note = humanized antibody
source                  1..7
                        mol_type = protein
                        organism = synthetic construct
SEQUENCE: 145
DASDLAS                                                                  7

SEQ ID NO: 146          moltype = AA   length = 7
FEATURE                 Location/Qualifiers
REGION                  1..7
                        note = humanized antibody
source                  1..7
                        mol_type = protein
                        organism = synthetic construct
SEQUENCE: 146
DASNLAS                                                                  7

SEQ ID NO: 147          moltype = AA   length = 7
FEATURE                 Location/Qualifiers
REGION                  1..7
                        note = humanized antibody
source                  1..7
                        mol_type = protein
                        organism = synthetic construct
SEQUENCE: 147
AASDLES                                                                  7

SEQ ID NO: 148          moltype = AA   length = 7
FEATURE                 Location/Qualifiers
REGION                  1..7
                        note = humanized antibody
source                  1..7
                        mol_type = protein
                        organism = synthetic construct
SEQUENCE: 148
RASTLAS                                                                  7

SEQ ID NO: 149          moltype = AA   length = 7
FEATURE                 Location/Qualifiers
REGION                  1..7
                        note = humanized antibody
source                  1..7
                        mol_type = protein
                        organism = synthetic construct
SEQUENCE: 149
```

-continued

```
YASTLAS                                                      7

SEQ ID NO: 150          moltype = AA  length = 7
FEATURE                 Location/Qualifiers
REGION                  1..7
                        note = humanized antibody
source                  1..7
                        mol_type = protein
                        organism = synthetic construct
SEQUENCE: 150
AASLLAS                                                      7

SEQ ID NO: 151          moltype = AA  length = 7
FEATURE                 Location/Qualifiers
REGION                  1..7
                        note = humanized antibody
source                  1..7
                        mol_type = protein
                        organism = synthetic construct
SEQUENCE: 151
SASTLAS                                                      7

SEQ ID NO: 152          moltype = AA  length = 7
FEATURE                 Location/Qualifiers
REGION                  1..7
                        note = humanized antibody
source                  1..7
                        mol_type = protein
                        organism = synthetic construct
SEQUENCE: 152
GASNLAS                                                      7

SEQ ID NO: 153          moltype = AA  length = 7
FEATURE                 Location/Qualifiers
REGION                  1..7
                        note = humanized antibody
source                  1..7
                        mol_type = protein
                        organism = synthetic construct
SEQUENCE: 153
GASTLAS                                                      7

SEQ ID NO: 154          moltype = AA  length = 12
FEATURE                 Location/Qualifiers
REGION                  1..12
                        note = humanized antibody
source                  1..12
                        mol_type = protein
                        organism = synthetic construct
SEQUENCE: 154
QNWWVIEHNG AA                                               12

SEQ ID NO: 155          moltype = AA  length = 12
FEATURE                 Location/Qualifiers
REGION                  1..12
                        note = humanized antibody
source                  1..12
                        mol_type = protein
                        organism = synthetic construct
SEQUENCE: 155
QSASYSTGPD WT                                              12

SEQ ID NO: 156          moltype = AA  length = 12
FEATURE                 Location/Qualifiers
REGION                  1..12
                        note = humanized antibody
source                  1..12
                        mol_type = protein
                        organism = synthetic construct
SEQUENCE: 156
QQGATTYNVD NV                                              12

SEQ ID NO: 157          moltype = AA  length = 13
FEATURE                 Location/Qualifiers
REGION                  1..13
                        note = humanized antibody
source                  1..13
                        mol_type = protein
                        organism = synthetic construct
```

-continued

```
SEQUENCE: 157
QCTYWNPDYI GGA                                                         13

SEQ ID NO: 158        moltype = AA   length = 12
FEATURE               Location/Qualifiers
REGION                1..12
                      note = humanized antibody
source                1..12
                      mol_type = protein
                      organism = synthetic construct
SEQUENCE: 158
LGGYSYSNTG PT                                                          12

SEQ ID NO: 159        moltype = AA   length = 15
FEATURE               Location/Qualifiers
REGION                1..15
                      note = humanized antibody
source                1..15
                      mol_type = protein
                      organism = synthetic construct
SEQUENCE: 159
LGVCTDISTD DLYNA                                                       15

SEQ ID NO: 160        moltype = AA   length = 12
FEATURE               Location/Qualifiers
REGION                1..12
                      note = humanized antibody
source                1..12
                      mol_type = protein
                      organism = synthetic construct
SEQUENCE: 160
LGVYTYSTDI HA                                                          12

SEQ ID NO: 161        moltype = AA   length = 12
FEATURE               Location/Qualifiers
REGION                1..12
                      note = humanized antibody
source                1..12
                      mol_type = protein
                      organism = synthetic construct
SEQUENCE: 161
LGVYTHISAD NA                                                          12

SEQ ID NO: 162        moltype = AA   length = 13
FEATURE               Location/Qualifiers
REGION                1..13
                      note = humanized antibody
source                1..13
                      mol_type = protein
                      organism = synthetic construct
SEQUENCE: 162
QQGYYSGGTD NDV                                                         13

SEQ ID NO: 163        moltype = AA   length = 12
FEATURE               Location/Qualifiers
REGION                1..12
                      note = humanized antibody
source                1..12
                      mol_type = protein
                      organism = synthetic construct
SEQUENCE: 163
QGSYYSSSWY NV                                                          12

SEQ ID NO: 164        moltype = AA   length = 10
FEATURE               Location/Qualifiers
REGION                1..10
                      note = humanized antibody
source                1..10
                      mol_type = protein
                      organism = synthetic construct
SEQUENCE: 164
QCNYIIDYGA                                                             10

SEQ ID NO: 165        moltype = AA   length = 10
FEATURE               Location/Qualifiers
REGION                1..10
                      note = humanized antibody
source                1..10
                      mol_type = protein
```

-continued

```
                                 organism = synthetic construct
SEQUENCE: 165
QSYYNSDSDA                                                             10

SEQ ID NO: 166            moltype = AA   length = 12
FEATURE                   Location/Qualifiers
REGION                    1..12
                          note = humanized antibody
source                    1..12
                          mol_type = protein
                          organism = synthetic construct
SEQUENCE: 166
QQGYTEDNID NT                                                          12

SEQ ID NO: 167            moltype = AA   length = 12
FEATURE                   Location/Qualifiers
REGION                    1..12
                          note = humanized antibody
source                    1..12
                          mol_type = protein
                          organism = synthetic construct
SEQUENCE: 167
QGAVYSGNTE WA                                                          12

SEQ ID NO: 168            moltype = AA   length = 13
FEATURE                   Location/Qualifiers
REGION                    1..13
                          note = humanized antibody
source                    1..13
                          mol_type = protein
                          organism = synthetic construct
SEQUENCE: 168
QGEFSCVSAD CIA                                                         13

SEQ ID NO: 169            moltype = AA   length = 12
FEATURE                   Location/Qualifiers
REGION                    1..12
                          note = humanized antibody
source                    1..12
                          mol_type = protein
                          organism = synthetic construct
SEQUENCE: 169
QCTYYDNNYG GA                                                          12

SEQ ID NO: 170            moltype = AA   length = 15
FEATURE                   Location/Qualifiers
REGION                    1..15
                          note = humanized antibody
source                    1..15
                          mol_type = protein
                          organism = synthetic construct
SEQUENCE: 170
QSWYYSGSGS YHSWA                                                       15

SEQ ID NO: 171            moltype = AA   length = 107
FEATURE                   Location/Qualifiers
source                    1..107
                          mol_type = protein
                          organism = Homo sapiens
SEQUENCE: 171
RTVAAPSVFI FPPSDEQLKS GTASVVCLLN NFYPREAKVQ WKVDNALQSG NSQESVTEQD      60
SKDSTYSLSS TLTLSKADYE KHKVYACEVT HQGLSSPVTK SFNRGEC                   107

SEQ ID NO: 172            moltype = AA   length = 329
FEATURE                   Location/Qualifiers
source                    1..329
                          mol_type = protein
                          organism = Homo sapiens
SEQUENCE: 172
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPEAAGG     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSREE     240
MTKNQVSLTC LVKGFYPSDI AVEWESNGQP ENNYKTTPPV LDSDGSFFLY SKLTVDKSRW     300
QQGNVFSCSV MHEALHNHYT QKSLSLSPG                                       329

SEQ ID NO: 173            moltype = AA   length = 123
FEATURE                   Location/Qualifiers
REGION                    1..123
```

-continued

```
                         note = humanized antibody
source                   1..123
                         mol_type = protein
                         organism = synthetic construct
SEQUENCE: 173
EVQLLESGGR LVQPGTSLRL SCAVSGIDLS SYAMGWVRQA PGKGLEYVGV ITSSATTYYA    60
SWAKGRFTIS KTSSKNTLYL QMNSLRAEDT AVYFCARGGP GYSTNTHYAF DPWGQGTLVT   120
VSS                                                                  123

SEQ ID NO: 174           moltype = AA  length = 108
FEATURE                  Location/Qualifiers
REGION                   1..108
                         note = Humanized antibody
source                   1..108
                         mol_type = protein
                         organism = synthetic construct
SEQUENCE: 174
DVQMTQSPSS LSASVGDRVT ITCQASQSIY SFLSWYQQKP GQAPKLLIYA ASDLESGVPS    60
RFSGSGSGTD FTLTISSLQP EDFATYYCQS NYIIDYGAFG QGTKVVIK               108

SEQ ID NO: 175           moltype = AA  length = 10
FEATURE                  Location/Qualifiers
REGION                   1..10
                         note = Humanized antibody
source                   1..10
                         mol_type = protein
                         organism = synthetic construct
SEQUENCE: 175
QSNYIIDYGA                                                            10

SEQ ID NO: 176           moltype = AA  length = 118
FEATURE                  Location/Qualifiers
REGION                   1..118
                         note = VR
source                   1..118
                         mol_type = protein
                         organism = synthetic construct
SEQUENCE: 176
QSLEESGGGL VKPEGSLTLT CKASGIDFSQ DYYMCWVRQA PGKGLEWIAC IYTGNDITYY    60
ASWAKGRFTV SKTSSTTVTL QMTSLTAADT ATYFCARDGG ANYYFKFWGQ GTLVTVSS     118

SEQ ID NO: 177           moltype = AA  length = 110
FEATURE                  Location/Qualifiers
REGION                   1..110
                         note = VR
source                   1..110
                         mol_type = protein
                         organism = synthetic construct
SEQUENCE: 177
DIVMTQTPAS VEAAVGGTVT IKCQASQSIS NLLAWYQQKP GQPPKLLIYG ASTLESGVPS    60
RFKGSGSGTE FTLTISDLGS ADAATYYCQN YAYSSGSWYS FGGGTEVVVK             110

SEQ ID NO: 178           moltype = AA  length = 6
FEATURE                  Location/Qualifiers
REGION                   1..6
                         note = CDR
source                   1..6
                         mol_type = protein
                         organism = synthetic construct
SEQUENCE: 178
QDYYMC                                                                6

SEQ ID NO: 179           moltype = AA  length = 17
FEATURE                  Location/Qualifiers
REGION                   1..17
                         note = CDR
source                   1..17
                         mol_type = protein
                         organism = synthetic construct
SEQUENCE: 179
CIYTGNDITY YASWAKG                                                    17

SEQ ID NO: 180           moltype = AA  length = 10
FEATURE                  Location/Qualifiers
REGION                   1..10
                         note = CDR
source                   1..10
                         mol_type = protein
                         organism = synthetic construct
```

-continued

```
SEQUENCE: 180
DGGANYYFKF                                                                     10

SEQ ID NO: 181          moltype = AA  length = 11
FEATURE                 Location/Qualifiers
REGION                  1..11
                        note = CDR
source                  1..11
                        mol_type = protein
                        organism = synthetic construct
SEQUENCE: 181
QASQSISNLL A                                                                   11

SEQ ID NO: 182          moltype = AA  length = 7
FEATURE                 Location/Qualifiers
REGION                  1..7
                        note = CDR
source                  1..7
                        mol_type = protein
                        organism = synthetic construct
SEQUENCE: 182
GASTLES                                                                        7

SEQ ID NO: 183          moltype = AA  length = 12
FEATURE                 Location/Qualifiers
REGION                  1..12
                        note = CDR
source                  1..12
                        mol_type = protein
                        organism = synthetic construct
SEQUENCE: 183
QNYAYSSGSW YS                                                                  12
```